US012325839B2

(12) United States Patent
Womack et al.

(10) Patent No.: US 12,325,839 B2
(45) Date of Patent: Jun. 10, 2025

(54) PRO-PERFUME COMPOSITIONS

(71) Applicant: FIRMENICH SA, Satigny (CH)

(72) Inventors: Gary Womack, Plainsboro, NJ (US); Andreas Herrmann, Satigny (CH)

(73) Assignee: FIRMENICH SA, Satigny (CH)

( * ) Notice: Subject to any disclaimer, the term of this patent is extended or adjusted under 35 U.S.C. 154(b) by 497 days.

(21) Appl. No.: 17/755,686

(22) PCT Filed: Dec. 18, 2020

(86) PCT No.: PCT/EP2020/086995
§ 371 (c)(1),
(2) Date: May 5, 2022

(87) PCT Pub. No.: WO2021/123144
PCT Pub. Date: Jun. 24, 2021

(65) Prior Publication Data

US 2023/0024269 A1 Jan. 26, 2023

Related U.S. Application Data

(60) Provisional application No. 62/951,028, filed on Dec. 20, 2019.

(30) Foreign Application Priority Data

Feb. 3, 2020 (EP) .................................... 20155108

(51) Int. Cl.
*C11B 9/00* (2006.01)
*A61K 8/35* (2006.01)

(52) U.S. Cl.
CPC .......... *C11B 9/0034* (2013.01); *C11B 9/0015* (2013.01); *C11B 9/0019* (2013.01); *C11B 9/0061* (2013.01)

(58) Field of Classification Search
CPC ... C11B 9/0015; C11B 9/0019; C11B 9/0034; C11B 9/0061; A61Q 13/00; A61K 8/35; A61K 8/34; A61K 2800/5922; A61K 2800/591
USPC ............................................ 512/21, 20, 8, 1
See application file for complete search history.

(56) References Cited

U.S. PATENT DOCUMENTS

| | | | | |
|---|---|---|---|---|
| 2,288,211 | A | 6/1942 | Schulz | |
| 6,218,355 | B1 | 4/2001 | Herrmann | |
| 2014/0323376 | A1* | 10/2014 | Berthier | B01J 13/16 512/4 |
| 2019/0008991 | A1 | 1/2019 | Horenziak et al. | |
| 2023/0032098 | A1* | 2/2023 | Struillou | C11B 9/0019 |

FOREIGN PATENT DOCUMENTS

| | | | | |
|---|---|---|---|---|
| WO | 2008093272 A2 | 8/2008 | | |
| WO | WO-2008142591 A2 * | 11/2008 | C07D 233/32 |
| WO | 2008154765 A1 | 12/2008 | | |
| WO | 2016135193 A1 | 9/2016 | | |
| WO | 2019068511 A1 | 4/2019 | | |
| WO | 2019243501 A1 | 12/2019 | | |
| WO | 2020188079 A1 | 9/2020 | | |

OTHER PUBLICATIONS

Daniel Schwendenwein et al, “Selective Enzymatic Transformation to Aldehydes in vivo by Fungal Carboxylate Reductase from Neurospora crassa”, Advanced Synthesis & Catalysis, vol. 358, No. 21, Nov. 3, 2016 (Nov. 3, 2016), pp. 3414-3421.
Sharma B. L. et al, “Thermodynamic and lamella models relationship for the eutectic system benzoic acid-cinnamic acid”, Crystal Research and Technology, vol. 39, No. 5, May 1, 2004 (May 1, 2004), pp. 454-464.
M. Seyfried et al, “Elucidation of the upper pathway of alicyclic musk Romandolide degradation in OECD screening tests with activated sludge”, Environmental Science and Pollution Research International, vol. 21, No. 16, Nov. 26, 2013 (Nov. 26, 2013), pp. 9487-9494.
Watanabe I et al, “Ester Compounds of Bulgarian Rose Concrete (*Rosa damascena* Mill)”, Int. Congr. Essent. Oils,Dec. 31, 1979 (Dec. 31, 1979), pp. 1-13.
Nicolas Paret et al, “Developing Multi Stimuli-Responsive Core/Shell Microcapsules to Control the Release of Volatile Compounds”, Macromolecular Materials and Engineering., vol. 304, No. 3, Dec. 27, 2018 (Dec. 27, 2018), p. 1800599.
Herrmann Andreas, “Photochemistry of 2-Oxoacetates: from Mechanistic Insights to Profragrances and Bursting Capsules”, CH Feb. 1, 2020 (Feb. 1, 2020), vol. 74, No. 1, pp. 39-48.
Claudia Turek et al, “Stability of Essential Oils: A Review : Stability of essential oils . . . ”, Comprehensive Reviews in Food Science and Food Safety, vol. 12, No. 1, Jan. 1, 2013 (Jan. 1, 2013), pp. 40-53.

(Continued)

*Primary Examiner* — Jessica Whiteley
(74) *Attorney, Agent, or Firm* — Armstrong Teasdale LLP

(57) ABSTRACT

Described herein is a perfuming composition including at least two pro-perfume compounds selected from: a pro-perfume compound releasing a perfume compound upon exposure to light, a pro-perfume compound releasing a perfume compound upon exposure to air/oxygen, a pro-perfume compound releasing a perfume compound upon exposure to heat, a pro-perfume compound releasing a perfume compound upon exposure to moisture, and a pro-perfume compound releasing a perfume compound upon exposure to enzymes. Also described herein is a perfumed consumer product including such a perfuming composition, as well as the use of the perfuming composition for improving, enhancing, conferring, and/or modifying the fragrance impression and/or fragrance intensity of a consumer product.

6 Claims, No Drawings

(56) References Cited

OTHER PUBLICATIONS

International Search Report and Written Opinion for corresponding PCT/EP2020/086995 mailed Mar. 23, 2021; 24 pages.

* cited by examiner

PRO-PERFUME COMPOSITIONS

CROSS-REFERENCE TO RELATED APPLICATIONS

This application is a U.S. National Phase Application of International Patent Application No. PCT/EP2020/086995, filed Dec. 18, 2020, which claims priority to European Patent Application No. 20155108.2, filed Feb. 3, 2020, and to U.S. Provisional Patent Application No. 62/951,028, filed Dec. 20, 2019, each of which is hereby incorporated by reference herein in its entirety.

TECHNICAL FIELD

The present invention relates to a perfuming composition comprising at least two pro-perfume compounds selected from the group consisting of a pro-perfume compound releasing a perfume compound upon exposure to light, a pro-perfume compound releasing a perfume compound upon exposure to air/oxygen, a pro-perfume compound releasing a perfume compound upon exposure to heat, a pro-perfume compound releasing a perfume compound upon exposure to moisture and a pro-perfume compound releasing a perfume compound upon exposure to enzymes. The present invention further concerns a perfumed consumer product comprising the inventive perfuming composition, as well as the use of the inventive perfuming composition for improving, enhancing, conferring and/or modifying the fragrance impression and/or fragrance intensity of a consumer product.

BACKGROUND OF THE INVENTION

The perfume industry has a particular interest for compositions or additives, which are capable of prolonging or enhancing the perfuming effect of at least one perfuming ingredient for a certain period of time. It is particularly desirable to obtain long-lasting properties for standard perfumery raw materials which are too volatile or have a poor substantivity by themselves, or which are only deposited in a small amount onto the surface of the final application. Furthermore, some of the perfumery ingredients are unstable and need to be protected against slow degradation prior to their use. Long-lasting perfumes are desirable for various applications, as for example fine or functional perfumery or cosmetic preparations. The washing and softening of textiles is a particular field in which there is a constant need to enable the effect of active substances, in particular perfumes, or perfuming compositions, to be effective for a certain period of time after washing, softening and drying. Indeed, many active substances which are particularly suitable for this type of application are known to lack tenacity on laundry, or do not remain on the laundry when rinsed, with the result that their perfuming effect is experienced only briefly and not very intensely. Given the importance of this type of application in the perfume industry, research in this field has been sustained, in particular with the aim of finding new, and more effective solutions to the aforementioned problems.

It has now been surprisingly found that a perfuming composition according to the present invention solves the above-mentioned problems, and is capable of efficiently releasing fragrance compounds (perfumery raw materials) from pro-perfume compounds comprised by the perfuming composition. In particular, it has been surprisingly found that the combination of pro-perfumes results in a more efficient and prolonged release of fragrance compounds.

DETAILED DESCRIPTION

Olfaction is a complex and dynamic process, and controlling the release profile of volatile fragrance compounds may maximize the impact of fragrance formulations and enrich the sensorial experience. The combination of pro-perfumes in a perfuming composition, such as the perfuming composition according to the present invention, may add a dimension of control and long-lastingness to the release profile of highly volatile perfumery raw materials (PRMs).

The present invention relates to a perfuming composition comprising at least two pro-perfume compounds selected from the group consisting of

- a pro-perfume compound releasing a perfume compound upon exposure to light,
- a pro-perfume compound releasing a perfume compound upon exposure to air/oxygen,
- a pro-perfume compound releasing a perfume compound upon exposure to heat,
- a pro-perfume compound releasing a perfume compound upon exposure to moisture and
- a pro-perfume compound releasing a perfume compound upon exposure to enzymes.

Under a "perfuming composition" is to be understood a composition that is able to impart a hedonic effect to e.g. a consumer product. In other words, a composition to be considered as being a perfuming composition must be recognized by a skilled person in the art of perfumery as being able to impart or modify the olfactory perception in a positive or pleasant way, and not just as imparting an odor.

According to the present invention, the perfuming composition comprises at least two pro-perfume compounds.

A "pro-perfume" or "pro-fragrance" is a compound that is able to release one, two or more perfume compounds, also termed PRMs (perfumery raw materials), upon external influence in a way that prolongs the perfuming effect of the PRMs. The PRMs are released from the pro-perfume by the cleavage of a covalent bond by exposure to light, air/oxygen, heat, moisture or enzymes, or combinations thereof, as an external trigger or stimulus. Typically, the pro-perfume itself has a low volatility, and is ideally (almost) odorless. The pro-perfume may be advantageously characterized by a vapor pressure below 0.01 Pa, as obtained by calculation using the software EPIwin v. 3.10 (2000, available at the US Environmental Protection Agency). According to one embodiment, the vapor pressure is below 0.001 Pa. The pro-perfume may also be advantageously characterized by a molecular weight above 270, even above 300, even above 350. The terms "pro-perfume" or "pro-fragrance" have the normal meaning in the art as for example reported in A. Herrmann, Angew. Chem. Int. Ed., 2007, 46, 5836-5863.

In a particular embodiment, the perfuming ingredient released by the pro-perfume compounds used in the invention's composition may impart an additional benefit beyond that of modifying or imparting an odor, such as long-lasting, blooming, malodour counteraction, antimicrobial effect, antiviral effect, microbial stability, pest control.

A "fragrance compound", "perfume compound" or "perfumery raw material" (PRM) is a compound, which is used as an active ingredient in perfuming preparations or compositions in order to impart a hedonic effect. In other words, a compound to be considered as being a perfuming ingredient must be recognized by a skilled person in the art of perfumery as being able to impart or modify in a positive or pleasant way the odor of a composition, and not just as having an odor.

The perfuming composition according to the present invention can comprise pro-perfume compounds that release PRMs upon exposure to light.

By "light", any form of electromagnetic radiation is meant, which is not limited to any particular wavelength. The release of PRMs from such pro-perfumes is usually more effective at lower wavelengths (higher energy input).

The perfuming composition according to the present invention can comprise pro-perfume compounds that release PRMs upon exposure to air/oxygen.

Thereby, the PRMs may be released from such pro-perfumes by oxidation in the presence of air (ambient air) or oxygen, preferably ambient air.

For the sake of clarity, by the expression "ambient air", or the similar, it is meant the normal meaning understood by a person skilled in the art, i.e. the oxidation occurs at room temperature, under air and atmospheric pressure. In other words, the environment wherein the compound is oxidized is air. Herewith it is understood, that the pro-perfume is oxidized in ambient air. In particular, it is understood that pro-perfume does not necessarily require a pure oxygen environment, heat or catalyst to be oxidized.

The perfuming composition according to the present invention can comprise pro-perfume compounds that release PRMs upon exposure to heat.

By "heat", it is meant any energy input that is caused by increased temperature. The temperature to be applied is not limited to a particular temperature range, but rather depends on the individual pro-perfume. It lies within the knowledge of a skilled person to determine appropriate temperatures.

The perfuming composition according to the present invention can comprise pro-perfume compounds that release PRMs upon exposure to moisture.

Such pro-perfumes may show chemical bonds that are susceptible to water-induced cleavage, and may thus be cleaved in the presence of water.

The perfuming composition according to the present invention can comprise pro-perfume compounds that release PRMs upon exposure to enzymes.

Such pro-perfumes may show chemical bonds that can efficiently be cleaved in the presence of enzymes. It lies within the knowledge of a skilled person to determine which chemicals bonds can effectively be cleaved by a certain type of enzyme.

In some cases, pro-perfumes may exist that are prompted to release perfumery raw materials not only based on one type of mechanism as mentioned above, but based on one or more of the types mentioned above simultaneously or independently from each other. However, for every pro-perfume there exists one or two types of release mechanism that are particularly efficient or superior to other types that may theoretically be envisaged. If not anyway mentioned within the context of the present invention, it lies well within the knowledge of a skilled person to determine the main types of release mechanism for existing pro-perfumes.

In a particular embodiment, the at least two pro-perfume compounds release PRMs by the same release mechanism.

In a particular embodiment, the perfuming composition comprises 2 to 5 or even more pro-perfume compounds, preferably 2 to 3 pro-perfume compounds. In a particular embodiment, the pro-perfume compounds to be used in the present invention are structurally different types of pro-perfume compounds.

In a particular embodiment, the perfuming composition comprises a first pro-perfume compound releasing a perfume compound upon exposure to air/oxygen and/or moisture and a second pro-perfume compound releasing a perfume compound upon exposure to air/oxygen and/or heat and/or moisture and/or light and/or enzyme, wherein the first and second pro-perfume compounds are structurally different types of pro-perfume compounds.

In a more particular embodiment, the perfuming composition comprises a first pro-perfume compound releasing a perfume compound upon exposure to air/oxygen and/or moisture and a second pro-perfume compound releasing a perfume compound upon exposure to air/oxygen and/or moisture, wherein the first and second pro-perfume compounds are structurally different types of pro-perfume compounds.

"Structurally different types of pro-perfume compounds" means that the pro-perfume compounds do not show the same chemical structure. In a particular embodiment, by structurally different types of pro-perfume compounds it is meant that the structurally different pro-perfume compounds do not fall under a common generic formula as described below.

In a particular embodiment, one of the at least two pro-perfume compounds to be used according to the present invention, preferably the first pro-perfume compound, is a compound of formula (I)

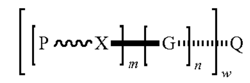

wherein:

a) w represents an integer from 1 to 10000;

b) n represents 1 or 0;

c) m represents an integer from 1 to 6;

d) P represents a hydrogen atom or a radical susceptible of generating an odoriferous α,β-unsaturated ketone, aldehyde or carboxylic ester and is represented by the formula (II)

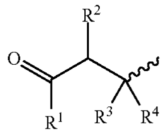

in which the wavy line indicates the location of the bond between said P and X;

$R^1$ represents a hydrogen atom, a $C_1$ to $C_6$ alkoxyl radical or a $C_1$ to $C_{15}$ linear, cyclic or branched alkyl, alkenyl or alkadienyl radical, optionally substituted by one to four $C_1$ to $C_4$ alkyl groups; and $R^2$, $R^3$ and $R^4$ represent independently of each other a hydrogen atom, an aromatic ring, or a $C_1$ to $C_{15}$ linear, cyclic or branched alkyl, alkenyl or alkadienyl radical, possibly substituted by $C_1$ to $C_4$ alkyl groups; or two, or three, of the groups $R^1$ to $R^4$ are bonded together to form a saturated or unsaturated ring having 5 to 20 carbon atoms and including the carbon atom to which said $R^1$, $R^2$, $R^3$ or $R^4$ groups are bonded, this ring being possibly substituted by $C_1$ to $C_8$ linear, branched or cyclic alkyl or alkenyl groups;

and with the proviso that at least one of the P groups is of the formula (II) as defined hereinabove;

e) X represents, independently from each other, a functional group selected from the group consisting of the formulae i) to xiv):

i)

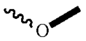

ii)

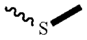

iii)

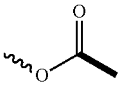

iv)

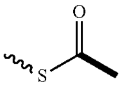

v)

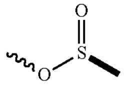

vi)

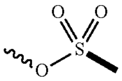

vii)

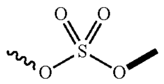

viii)

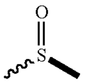

ix)

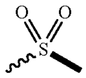

x)

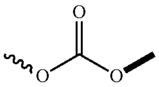

xi)

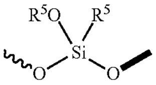

xii)

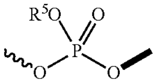

xiii)

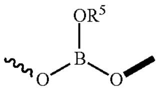

xiv)

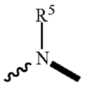

in which formulae the wavy lines are as defined previously and the bold lines indicate the location of the bond between said X and G, and $R^5$ represents a hydrogen atom, a $C_1$ to $C_{22}$, saturated or unsaturated, alkyl group or an aryl group, possibly substituted by $C_1$ to $C_6$ alkyl or alkoxyl groups or halogen atoms; and with the proviso that X may not exist when P represents a hydrogen atom;

f) G represents a multivalent radical (with a m+1 valence) derived from cyclic, linear or branched alkyl, cyclic, linear or branched alkenyl, phenyl, alkylphenyl or alkenylphenyl hydrocarbon radical having from 1 to 22 carbon atoms, said hydrocarbon radical being possibly substituted and containing from 1 to 10 functional groups selected from the group consisting of halogens, alcohols, ethers, esters, ketones, aldehydes, carboxylic acids, thiols, thioethers, amines, quaternary amines and amides; and g) Q represents a hydrogen atom (in which case w=1 and n=1), or represents a polymer or co-polymer selected from the group consisting of poly(alkylimine)s, polypeptides (e.g. polylysine) or polysaccharides selected from the group consisting of cellulose, cyclodextrins and starches, or cationic quaternized silicon polymers, or still a polymer or random co-polymer derived from monomeric units selected from the group consisting of the formulae A) to C):

A-1)

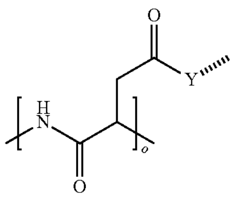

A-2)

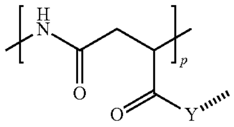

A-3)

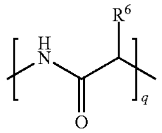

B-1)

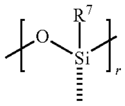

B-2)

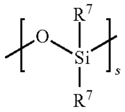

C-1)

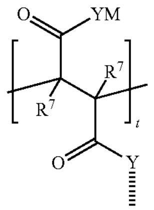

C-2)

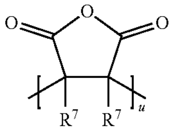

-continued

C-3)

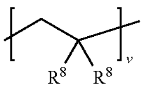

wherein the hatched lines indicate the location of the bond between said monomeric unit and G;

Y represents an oxygen or sulfur atom or a $NR^7$ group;

o, p, q, r, s, t, u and v all represent independent of each other fractions between 0 and 1, with o+p+q=1, r+s=1 and t+u+v=1 and with the proviso that either o or p, as well as r and t are not equal to 0;

$R^6$ represents a hydrogen atom or a side chain from a natural or unnatural amino acid, such as glycine, alanine, phenylalanine, arginine, histidine, lysine, aspartic acid, glutamic acid, cysteine, methionine, glutamine, asparagine, threonine, serine, leucine, isoleucine, valine, tyrosine or tryptophan;

$R^7$ represents, simultaneously or independently, a hydrogen atom or a $C_1$-$C_{16}$ hydrocarbon group;

$R^8$ represents, simultaneously or independently of each other a hydrogen or halide atom;

a $C_1$-$C_6$ hydrocarbon group optionally comprising from 1 to 4 heteroatoms selected from the group consisting of oxygen and sulfur atoms;

a carboxylic group of formula COOR*, wherein R* represents a hydrogen atom, a $C_1$-$C_{60}$ alkyl or alkenyl group optionally comprising from 1 to 30 oxygen atoms;

a $OR^7$ group or a $COR^7$ group; or a pyrrolidone unit, connected by the nitrogen atom; and M represents a hydrogen atom, an alkali or earth alkali metal ion.

In a particular embodiment, X represents a functional group selected from the group consisting of the formulae ii), iii), viii), ix) and xiv). In a particular embodiment, X represents the functional group of formula ii).

As "odoriferous α,β-unsaturated ketone, aldehyde or carboxylic ester", the expression used in the definition of P, it is understood an α,β-unsaturated ketone, aldehyde or carboxylic ester, which is recognized by a skilled person as being used in perfumery as perfuming ingredient. In general, said odoriferous α,β-unsaturated ketone, aldehyde or carboxylic ester is a compound having from 8 to 20 carbon atoms, or even more preferably between 10 and 15 carbon atoms.

Similarly, it is not possible to provide an exhaustive list of the currently known odoriferous compounds, which can be used in the synthesis of the invention compounds defined hereinabove and subsequently be released. However, the following can be named as preferred examples: alpha-damascone, beta-damascone, gamma-damascone, delta-damascone, alpha-ionone, beta-ionone, gamma-ionone, delta-ionone, beta-damascenone, 1-[6-ethyl-2,6-dimethyl-3-cyclohexen-1-yl]-2-buten-1-one, 3-methyl-5-propyl-2-cyclohexen-1-one, 2-methyl-5-(1-propen-2-yl)-2-cyclohexen-1-one, 2,5-dimethyl-5-phenyl-1-hexen-3-one, 1-(5,5-dimethyl-1-cyclohexen-1-yl)-4-penten-1-one, 3,7-dimethylocta-2,6-dienal, 8-methyl-alpha-ionone or 10-methyl-alpha-ionone, 2-octenal, 1-(2,2,3,6-tetramethylcyclohexyl)but-2-en-1-one, 4-(2,2,3,6-tetramethylcyclohexyl)but-3-en-2-one, 2-cyclopentadecen-1-one, 4,4a-dimethyl-6-(1-propen-2-yl)-4,4a,5,6,7,8-hexahydro-2(3H)-naphthalenone (nootkatone), (E)-3-phenylprop-2-enal (cinnamic aldehyde), 2,6,6-trimethylspiro[bicyclo[3.1.1]heptane-3,1'-cyclohexan]-2'-en-4'-one, ethyl 2,4-deca-dienoate, ethyl 2-octenoate, methyl 2-nonenoate, ethyl 2,4-undecadienoate, 4-methylpent-3-en-2-one, oct-2-en-4-one, and methyl 5,9-dimethyl-2,4,8-decatrienoate.

In a particular embodiment, P represents a radical selected from the group consisting of formulae (P-1) to (P-14), in the form of any one of its isomers:

(P-1)

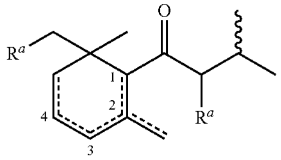

(P-2)

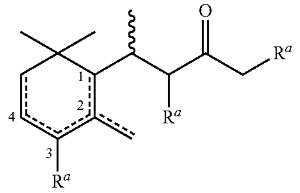

(P-3)

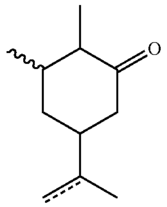

(P-4)

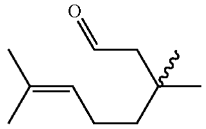

(P-5)

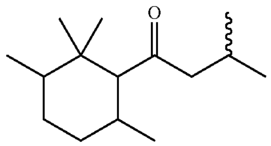

(P-6)

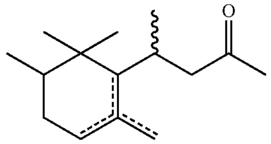

(P-7)

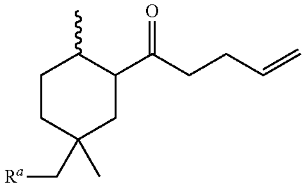

(P-8)

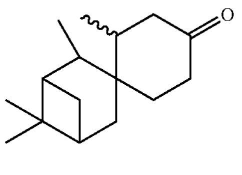

-continued (P-9)

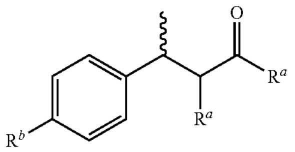

(P-10)

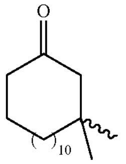

(P-11)

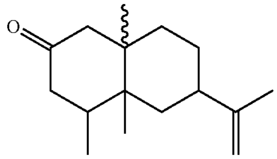

(P-12)

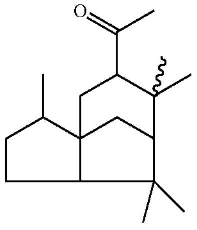

(P-13)

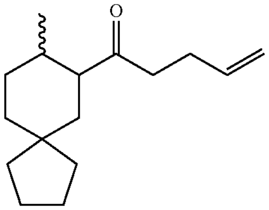

(P-14)

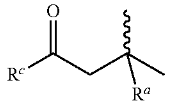

in which formulae the wavy lines have the meaning indicated above and the dotted lines represent a single or double bond, $R^a$ being a hydrogen atom or a methyl group and $R^b$ representing a hydrogen atom, a hydroxyl or methoxy group or a $C_1$-$C_4$ linear or branched alkyl group and $R^c$ representing a hydrogen atom or a $C_1$-$C_4$ linear or branched alkyl group.

In a particular embodiment, P represents a radical selected from the group consisting of formulae (P-1)'

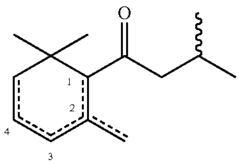

-continued (P-2)'

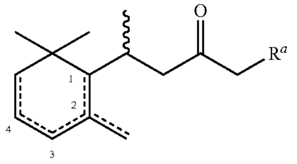

(P-3)

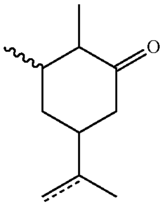

(P-5)

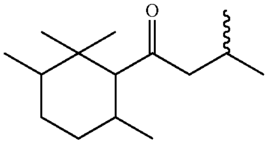

(P-6)

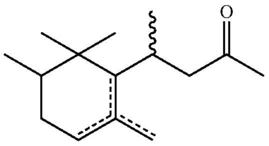

(P-7)

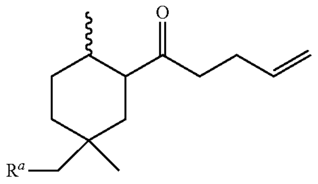

(P-13)

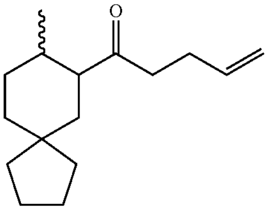

(P-14)'

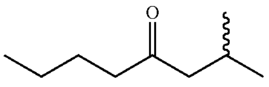

wherein the wavy lines have the meaning indicated above and the dotted lines represent a single or double bond, and $R^a$ being a hydrogen atom or a methyl group.

In a particular embodiment, P represents a radical selected from the group consisting of formulae (P-1), (P-2), (P-1)', (P-2)', (P-3), (P-7), (P-13), (P-14) or (P-14)' as defined above. Preferably, P represents a radical selected from the group consisting of formulae (P-1), (P-1)', (P-2), (P-2)', (P-3) or (P-14)' as defined above.

In a particular embodiment, G may represent a divalent cyclic, linear or branched alkyl, alkenyl, alkandienyl or alkylbenzene hydrocarbon radical having from 1 to 22 carbon atoms, said hydrocarbon radical being possibly substituted and containing from 1 to 10 functional groups selected from the group consisting of ethers, esters, ketones, aldehydes, carboxylic acids, thiols, thioethers, amines, quaternary amines and amides.

In a particular embodiment, G represents a divalent linear or branched alkyl hydrocarbon radical having from 1 to 22 carbon atoms, said hydrocarbon radical being possibly substituted and containing from 1 to 5 functional groups selected from the group consisting of ethers, esters, ketones, aldehydes, carboxylic acids, thiols, thioethers, amines, quaternary amines and amides.

In a particular embodiment, G represents a divalent linear or branched alkyl hydrocarbon radical having from 2 to 15 carbon atoms, said hydrocarbon radical being possibly substituted and containing from 1 to 2 functional groups selected from the group consisting of ethers and esters.

In a particular embodiment, G represents a divalent linear alkyl hydrocarbon radical having from 3 to 15 carbon atoms, said hydrocarbon radical being possibly substituted and containing one ester functional group.

In a particular embodiment, G represents a divalent linear alkyl hydrocarbon radical having from 3 to 14 carbon atoms.

In a particular embodiment, Q represents a hydrogen atom or a co-polymer comprising at least one repeating unit of formula B-1 as defined above.

In a particular embodiment, Q represents a hydrogen atom or a co-polymer comprising at least one repeating unit of formula B-1 and at least one repeating unit of formula B-2.

In a particular embodiment, $R^7$ represents, simultaneously or independently, a hydrogen atom or a $C_{1-3}$ alkyl group. Preferably, $R^7$ represents, simultaneously or independently, a hydrogen atom or a methyl or an ethyl group. More preferably, $R^7$ represents, simultaneously or independently, a hydrogen atom or a methyl group.

In a particular embodiment, the first pro-perfume compound is defined by formula (I) as mentioned above, wherein w=1; n=1; m=1;

P represents a radical susceptible of generating an odoriferous α,β-unsaturated ketone, aldehyde and is represented by the formula (II)

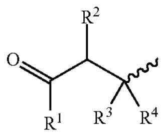

wherein $R^2$, $R^3$ and $R^4$ represent independently of each other a hydrogen atom, a $C_6$ to $C_{10}$ aromatic ring, or a $C_1$ to $C_{15}$ linear, cyclic or branched alkyl, alkenyl or alkadienyl radical, possibly substituted by $C_1$ to $C_4$ alkyl groups; or two, or three, of the groups $R^1$ to $R^4$ are bonded together to form a saturated or unsaturated ring having 5 to 20 carbon atoms and including the carbon atom to which said $R^1$, $R^2$, $R^3$ or $R^4$ groups are bonded, this ring being possibly substituted by $C_1$ to $C_8$ linear, branched or cyclic alkyl or alkenyl groups;

X represents formula ii)

G represents a divalent radical derived from cyclic, linear or branched alkyl, alkenyl, phenyl, alkylphenyl or alkenylphenyl hydrocarbon radical having from 2 to 8 carbon atoms optionally comprising 1 or 2 oxygen, sulfur and/or nitrogen atoms Q represents a polymer or random co-polymer derived from formula B-1), wherein $R^7$ represents a $C_1$-$C_{16}$ hydrocarbon group.

In a particular embodiment, the first pro-perfume compound is a compound selected from the group consisting of formulae a) to d)

a)

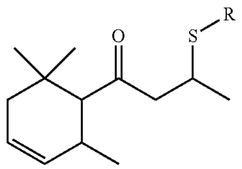

b)

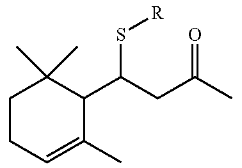

c)

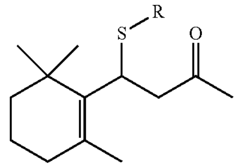

d)

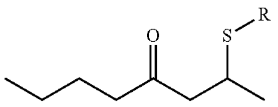

wherein R represents a $C_1$-$C_{20}$ alkyl or alkenyl group, preferably a $C_6$-$C_{16}$ alkyl or alkenyl group, more preferably a $C_{12}$ alkyl group.

The pro-perfume of formula a) releases delta-damascone as fragrance compound. Said pro-perfume may preferably be (±)-trans-3-(dodecylthio)-1-(2,6,6-trimethyl-3-cyclohexen-1-yl)-1-butanone. Delta-damascone is also known as 1-[(1RS,2SR)-2,6,6-trimethyl-3-cyclohexen-1-yl]-2-buten-1-one.

The pro-perfume of formula b) or c) releases ionone as fragrance compound. Said pro-perfume may be present as an isomeric mixture of formula b) and formula c). The isomeric mixture may have a weight ratio of formula b) and formula c) from 40:60 to 60:40.

In particular, the isomeric mixture may have a weight ratio of formula b) and formula c) of about 55:45. In particular, said pro-perfume releases two isomers of ionone as fragrance compound.

In particular, the pro-perfume of formula b) releases alpha-ionone as fragrance compound. Said pro-perfume of formula b) may preferably be (±)-4-(dodecylthio)-4-(2,6,6-trimethyl-2-cyclohexen-1-yl)-2-butanone. Alpha-ionone is also known as (±)-(3E)-4-(2,6,6-trimethyl-2-cyclohexen-1-yl)-3-buten-2-one.

In particular, the pro-perfume of formula c) releases beta-ionone as fragrance compound. Said pro-perfume of formula c) may preferably be (±)-4-(dodecylthio)-4-(2,6,6-trimethyl-1-cyclohexen-1-yl)-2-butanone. Beta-ionone is also known as (3E)-4-(2,6,6-trimethyl-1-cyclohexen-1-yl)-3-buten-2-one.

The pro-perfume of formula d) releases oct-2-en-4-one as fragrance compound. Said pro-perfume may preferably be (±)-2-(dodecylthio)octan-4-one. Oct-2-en-4-one may be released as its (E)- or (Z)-isomers, or as mixtures thereof, with the (E)-isomer being preferred.

In a particular embodiment, one of the at least two pro-perfume compounds, preferably the first pro-perfume compound, is selected from the group consisting of 3-(dodecylthio)-1-(2,6,6-trimethylcyclohex-3-en-1-yl)butan-1-one (Haloscent® D), 3-(dodecylthio)-1-(2,6,6-trimethylcyclohex-2-en-1-yl)butan-1-one, 4-(dodecylthio)-4-(2,6,6-trimethylcyclohex-2-en-1-yl)butan-2-one (Haloscent® I) and 4-(dodecylthio)-4-(2,6,6-trimethylcyclohex-1-en-1-yl) butan-2-one (Haloscent® I), 2-(dodecylthio)-4-octanone, 2-(dodecylsulfonyl)octan-4-one, 4-(dodecylthio)-4-methylpentan-2-one, methyl or ethyl N,S-bis(4-oxo-4-(2,6,6-trimethylcyclohex-3-en-1-yl)butan-2-yl)-L-cysteinate, methyl or ethyl S-(4-oxo-4-(2,6,6-trimethylcyclohex-3-en-1-yl)butan-2-yl)-L-cysteinate and 4-oxooctan-2-yl dodecanoate, or any mixtures thereof.

In a particular embodiment, one of the at least two pro-perfume compounds to be used in the present invention, preferably the first pro-perfume compound, is a linear polysiloxane co-polymer comprising at least one repeating unit of formula (III)

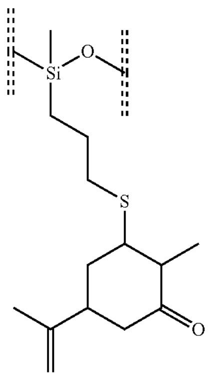

wherein the double hatched lines indicate the bonding to another repeating unit.

The pro-perfume of formula (III) releases 2-methyl-5-(prop-1-en-2-yl)cyclohex-2-en-1-one as fragrance compound, which is also known as carvone. Carvone exists in the form of two enantiomers, namely (R)-(−)-2-methyl-5-(1-propen-2-yl)-2-cyclohexen-1-one (L-carvone or carvone laevo) and (S)-(+)-2-methyl-5-(1-propen-2-yl)-2-cyclohexen-1-one (D-carvone or carvone dextro). The two enantiomers have been reported to have slightly different mint odor tonalities. Nevertheless, according to the invention, both enantiomers are expected to have a similar effect in view of the preparation of the co-polymer and the release efficiency. According to the invention, carvone can either be used as a racemate or as a mixture enriched in either one of the two enantiomers. Preferably, a mixture enriched in carvone laevo is used.

In a particular embodiment, one of the at least two pro-perfume compounds to be used in the present invention, preferably the second pro-perfume compound, is a compound of formula (IV)

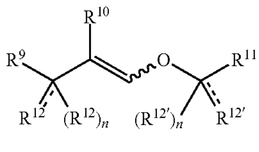

wherein, $R^9$ represents a $C_{1-15}$ alkyl, $C_{2-15}$ alkenyl, $C_{3-15}$ cycloalkyl or $C_{5-15}$ cycloalkenyl group, each optionally substituted with one or more of a $C_{1-15}$ alkyl, $C_{1-15}$ alkoxy, $C_{3-15}$ cycloalkyl, $C_{5-15}$ cycloalkenyl, $C_{6-10}$ aryl and/or $C_{6-10}$ aryloxy group, each optionally substituted with one or more of a $C_{1-8}$ alkyl, $C_{1-8}$ alkoxy, hydroxy, carboxylic acid and/or $C_{1-4}$ carboxylic ester group;

$R^{10}$ represents a hydrogen atom, a $C_{1-15}$ alkyl group or a $OR^{10'}$ wherein $R^{10'}$ represents a $C_{1-12}$ alkyl group, a $C_{3-12}$ alkenyl group, a phenethyl group or a benzyl group;

$R^9$ and $R^{10}$, when taken together, form a $C_{5-15}$ cycloalkyl, $C_{5-15}$ cycloalkenyl, $C_{4-14}$ heterocycloalkyl or $C_{4-14}$ heterocycloalkenyl group, each optionally substituted with one or more of a $C_{1-15}$ alkyl, $C_{1-15}$ alkoxy, $C_{3-15}$ cycloalkyl, $C_{5-15}$ cycloalkenyl, $C_{6-10}$ aryl group, each optionally substituted with one or more of a $C_{1-8}$ alkyl, $C_{1-8}$ alkoxy, carboxylic acid and/or $C_{1-4}$ carboxylic ester group, wherein the heteroatom represents one or more of an oxygen;

$R^{11}$ represents a hydrogen, a $C_{1-15}$ alkyl, $C_{2-15}$ alkenyl, $C_{3-15}$ cycloalkyl, $C_{5-15}$ cycloalkenyl or $C_{6-10}$ aryloxy group, each optionally substituted with one or more a $C_{1-15}$ alkyl, $C_{1-15}$ alkoxy, $C_{3-15}$ cycloalkyl, $C_{5-15}$ cycloalkenyl, $C_{6-10}$ aryl and/or $C_{6-10}$ aryloxy group, each optionally substituted with one or more of a $C_{1-8}$ alkyl, $C_{1-8}$ alkoxy, carboxylic acid and/or $C_{1-4}$ carboxylic ester group; and $R^{12}$ and $R^{12'}$, each independently, represent a hydrogen or a $C_{1-5}$ alkyl group; and $R^{11}$ and $R^{12'}$, when taken together, form a $C_{3-15}$ cycloalkyl, $C_{5-15}$ cycloalkenyl group or $C_{6-10}$ aryl group, each optionally substituted with one or more of a $C_{1-15}$ alkyl, $C_{2-10}$ alkenyl, $C_{1-15}$ alkoxy, $C_{3-15}$ cycloalkyl, $C_{5-15}$ cycloalkenyl, $C_{6-10}$ aryl and/or $C_{6-10}$ aryloxy group, each optionally substituted with one or more of a $C_{1-8}$ alkyl, $C_{1-8}$ alkoxy, carboxylic acid and/or $C_{1-4}$ carboxylic ester group;

$R^9$ and $R^{12}$, when taken together, form a $C_{3-15}$ cycloalkyl, $C_{5-15}$ cycloalkenyl or $C_{6-10}$ aryl group, each optionally substituted with one or more of a $C_{1-15}$ alkyl, $C_{2-10}$ alkenyl, $C_{1-15}$ alkoxy, $C_{3-15}$ cycloalkyl, $C_{5-15}$ cycloalkenyl, $C_{6-10}$ aryl and/or $C_{6-10}$ aryloxy group, each optionally substituted with one or more of a $C_{1-8}$ alkyl, $C_{1-8}$ alkoxy, carboxylic acid and/or $C_{1-4}$ carboxylic ester group;

the dotted line represent a single bond when n is 1 or the dotted line represent a double bond when n is 0 provided that the dotted line is a double bond when $R^9$ and $R^{12}$ and/or $R^{11}$ and $R^{12'}$ are taken together to form $C_{6-10}$ aryl.

For the sake of clarity, in case $R^{11}$ and $R^{12'}$, when taken together form a $C_{6-10}$ aryl group, one $R^{12}$ given in the formula above is to be omitted.

For the sake of clarity, in case $R^9$ and $R^{12}$, when taken together form a $C_{6-10}$ aryl group, one $R^{12}$ given in the formula above is to be omitted.

The term "optionally" is understood that a certain group to be optionally substituted can or cannot be substituted with a certain functional group. The term "one or more" is understood as being substituted with 1 to 7, preferably 1 to 5, and more preferably 1 to 3 of a certain functional group.

The terms "alkyl" and "alkenyl" are understood as comprising branched and linear alkyl and alkenyl groups. The terms "alkenyl", "cycloalkenyl" and "heterocycloalkenyl" is understood as comprising 1, 2 or 3 olefinic double bonds, preferably 1 or 2 olefinic double bonds. The terms “cycloalkyl”, “cycloalkenyl”, “heterocycloalkyl” and “heterocycloalkenyl” are understood as comprising a monocyclic or fused, spiro and/or bridged bicyclic or tricyclic cycloalkyl, cycloalkenyl, heterocycloalkyl and heterocycloalkenyl groups, preferably monocyclic cycloalkyl, cycloalkenyl, heterocycloalkyl and heterocycloalkenyl groups.

In a particular embodiment, in case, “$R^9$ and $R^{12}$, when taken together” and/or “$R^{11}$ and $R^{12'}$, when taken together” form a cycloalkenyl group, it is understood that the olefinic double bond is not adjacent to the carbon connecting $R^9$ and $R^{12}$ or $R^{11}$ and $R^{12}$, respectively. Preferably, in case an alkenyl group is substituted with an alkoxy group, the alkoxy group cannot be adjacent to the olefinic double bond of the alkenyl group to form an enol ether.

For the sake of clarity, in case $R^9$ and $R^{12}$ or $R^{11}$ and $R^{12'}$, when taken together form a $C_{6-10}$ aryl, one $R^{12}$ given in the formula above is to be omitted.

In a particular embodiment, $R^9$ represents a $C_{1-10}$ alkyl, $C_{2-10}$ alkenyl, $C_{3-11}$ cycloalkyl or $C_{5-11}$ cycloalkenyl group, each optionally substituted with one or more of a $C_{1-4}$ alkyl, $C_{1-4}$ alkoxy, $C_{3-8}$ cycloalkyl, $C_{5-8}$ cycloalkenyl, $C_6$ aryl and/or $C_6$ aryloxy group, each optionally substituted with one or more of a $C_{1-4}$ alkyl or a $C_{1-4}$ alkoxy, carboxylic acid and/or $C_{1-4}$ carboxylic ester group.

In a particular embodiment, $R^9$ represents a $C_{1-10}$ alkyl, $C_{2-10}$ alkenyl or $C_{3-11}$ cycloalkyl group, each optionally substituted with one or more of a $C_{1-4}$ alkyl, $C_{1-4}$ alkoxy, $C_{3-8}$ cycloalkyl, $C_{5-8}$ cycloalkenyl, $C_6$ aryl and/or $C_6$ aryloxy group, each optionally substituted with one or more of a $C_{1-4}$ alkyl or a $C_{1-4}$ alkoxy group.

In a particular embodiment, $R^9$ represents a $C_{1-10}$ alkyl group, optionally substituted with a $C_{5-7}$ cycloalkyl, $C_{5-7}$ cycloalkenyl and/or $C_6$ aryl group, each optionally substituted with one or more of a $C_{1-4}$ alkyl and/or $C_{1-4}$ alkoxy group. Preferably, $R^9$ represents a $C_{1-10}$ alkyl group, optionally substituted with a $C_{5-7}$ cycloalkyl, $C_{5-7}$ cycloalkenyl and/or $C_6$ aryl group, each optionally substituted with one or more of methyl and/or methoxy group.

In a particular embodiment, when $R^{10}$ represents a $OR^{10'}$ wherein $R^{10'}$ represents a $C_{1-12}$ alkyl group, a $C_{3-12}$ alkenyl group, a phenethyl group or a benzyl group, then $R^9$ and $R^{12}$, when taken together, form a $C_{6-10}$ aryl group, each optionally substituted with one or more of a $C_{1-15}$ alkyl, $C_{2-10}$ alkenyl, $C_{1-15}$ alkoxy, $C_{3-15}$ cycloalkyl, $C_{5-15}$ cycloalkenyl, $C_{6-10}$ aryl and/or $C_{6-10}$ aryloxy group, each optionally substituted with one or more of a $C_{1-8}$ alkyl, $C_{1-8}$ alkoxy, carboxylic acid and/or $C_{1-4}$ carboxylic ester group.

In a particular embodiment, $R^{10}$ represents a hydrogen atom, a $C_{1-15}$ alkyl group or a $C_{1-6}$ alkoxy group. In a particular embodiment, $R^{10}$ represents a hydrogen atom, a $C_{1-10}$ alkyl group. Preferably, $R^{10}$ represents a hydrogen atom, a $C_{1-5}$ alkyl or a $C_{1-3}$ alkyl group, more preferably a methyl group.

In a particular embodiment, $R^9$ and $R^{10}$, when taken together, form a $C_{5-11}$ cycloalkyl, $C_{5-11}$ cycloalkenyl, $C_{4-11}$ heterocycloalkyl, or $C_{4-11}$ heterocycloalkenyl group, each optionally substituted with one or more of a $C_{1-5}$ alkyl, $C_{1-5}$ alkoxy, $C_{3-8}$ cycloalkyl, $C_{5-8}$ cycloalkenyl or $C_6$ aryl group, each optionally substituted with one or more of a $C_{1-5}$ alkyl, $C_{1-5}$ alkoxy, carboxylic acid and/or $C_{1-4}$ carboxylic ester group, wherein the heteroatom represents one or more of an oxygen.

In a particular embodiment, $R^9$ and $R^{10}$, when taken together, form a $C_{5-7}$ cycloalkyl, $C_{5-7}$ cycloalkenyl, $C_{5-7}$ heterocycloalkyl, or $C_{5-8}$ heterocycloalkenyl group, each optionally substituted with one or more of a $C_{1-4}$ alkyl, $C_{1-4}$ alkoxy, $C_{5-7}$ cycloalkyl, $C_{5-7}$ cycloalkenyl or $C_6$ aryl group, each optionally substituted with one or more of a $C_{1-3}$ alkyl, $C_{1-3}$ alkoxy, carboxylic acid and/or $C_{1-3}$ carboxylic ester group, wherein the heteroatom represents one or more of an oxygen.

In a particular embodiment, $R^9$ and $R^{10}$, when taken together, form a $C_{5-7}$ cycloalkyl or $C_{5-7}$ cycloalkenyl group, each optionally substituted with one or more of a $C_{1-4}$ alkyl or $C_{1-4}$ alkoxy group.

In a particular embodiment, $R^{12}$ and $R^{12'}$, each independently, represents a hydrogen or a $C_{1-5}$ alkyl group. Preferably, $R^{12}$ and $R^{12'}$, each independently, represents a hydrogen or a $C_{1-3}$ alkyl group. Preferably, $R^{12}$ and $R^{12'}$, each independently, represents hydrogen and only one $R^{12}$ or $R^{12'}$ represents a $C_{1-3}$ alkyl group. Preferably, $R^{12}$ and $R^{12'}$, each independently represents hydrogen and only one $R^{12}$ or $R^{12'}$ represents a $C_{1-2}$ alkyl group. Preferably, $R^{12}$ and $R^{12'}$ represents hydrogen.

In a particular embodiment, $R^9$ and $R^{12}$, being adjacent to $R^9$, when taken together, form a $C_{3-11}$ cycloalkyl, $C_{5-11}$ cycloalkenyl or $C_{6-10}$ aryl group, each optionally substituted with one or more of a $C_{1-5}$ alkyl, $C_{1-5}$ alkoxy, $C_{3-7}$ cycloalkyl, $C_{5-7}$ cycloalkenyl and/or $C_6$ aryl group, each optionally substituted with one or more of a $C_{1-4}$ alkyl or $C_{1-4}$ alkoxy group.

In a particular embodiment, $R^9$ and $R^{12}$, when taken together, form a $C_{3-11}$ cycloalkyl, $C_{5-11}$ cycloalkenyl or $C_{6-10}$ aryl group, each optionally substituted with one or more of a $C_{1-3}$ alkyl or $C_{1-3}$ alkoxy group.

In a particular embodiment, $R^9$ and $R^{12}$, when taken together, form a $C_{3-11}$ cycloalkyl or $C_{6-10}$ aryl group, optionally substituted with one or more of a $C_{1-3}$ alkyl or $C_{1-3}$ alkoxy group.

In a particular embodiment, $R^{11}$ represents a $C_{1-10}$ alkyl, $C_{2-10}$ alkenyl, $C_{3-15}$ cycloalkyl or $C_{5-11}$ cycloalkenyl group, each optionally substituted with one or more of a $C_{1-5}$ alkyl, $C_{1-5}$ alkoxy, $C_{3-8}$ cycloalkyl, $C_{5-8}$ cycloalkenyl, $C_6$ aryl and/or $C_6$ aryloxy group, each optionally substituted with one or more of a $C_{1-5}$ alkyl or $C_{1-5}$ alkoxy group.

In a particular embodiment, $R^{11}$ represents a $C_{1-10}$ alkyl, $C_{3-10}$ alkenyl, $C_{4-15}$ cycloalkyl or $C_{5-11}$ cycloalkenyl group, each optionally substituted with one or more of a $C_{1-4}$ alkyl, $C_{1-4}$ alkoxy, $C_{5-6}$ cycloalkyl, $C_{5-6}$ cycloalkenyl $C_6$ aryl and/or $C_6$ aryloxy group, each optionally substituted with one or more of a $C_{1-3}$ alkyl or $C_{1-3}$ alkoxy group.

In a particular embodiment, $R^{11}$ represents a $C_{1-10}$ alkyl, $C_{3-10}$ alkenyl or $C_{5-15}$ cycloalkyl group, each optionally substituted with one or more of a $C_{1-4}$ alkyl, $C_6$ aryl and/or $C_6$ aryloxy group.

In a particular embodiment, $R^{11}$ and $R^{12'}$, being adjacent to $R^{11}$, when taken together, form a $C_{3-12}$ cycloalkyl, $C_{5-11}$ cycloalkenyl or $C_{6-10}$ aryl group, each optionally substituted with one or more of a $C_{1-5}$ alkyl, $C_{1-5}$ alkoxy, $C_{3-7}$ cycloalkyl, $C_{5-7}$ cycloalkenyl and/or $C_6$ aryl group, each optionally substituted with one or more of a $C_{1-4}$ alkyl or $C_{1-4}$ alkoxy group.

In a particular embodiment, $R^{11}$ and $R^{12'}$, when taken together, form a $C_{3-12}$ cycloalkyl, $C_{5-11}$ cycloalkenyl group or $C_{6-10}$ aryl group, each optionally substituted with one or more of a $C_{1-3}$ alkyl or $C_{1-3}$ alkoxy group.

In a particular embodiment, $R^{11}$ and $R^{12'}$, when taken together, form a $C_{3-12}$ cycloalkyl group or $C_{6-10}$ aryl group, optionally substituted with one or more of a $C_{1-3}$ alkyl or $C_{1-3}$ alkoxy group.

In a particular embodiment, one of the at least two pro-perfume compounds, preferably the second pro-perfume compound, is selected from the group consisting of (2-((2-methylundec-1-en-1-yl)oxy)ethyl)benzene, 1-methoxy-4-(3-methyl-4-phenethoxybut-3-en-1-yl)benzene, (3-methyl-4-phenethoxybut-3-en-1-yl)benzene, 1-(((Z)-hex-3-en-1-yl)oxy)-2-methylundec-1-ene, (2-((2-methylundec-1-en-1-yl)oxy)ethoxy)benzene, 2-methyl-1-(octan-3-yloxy)undec-1-ene, 1-methoxy-4-(1-phenethoxyprop-1-en-2-yl)benzene, 1-methyl-4-(1-phenethoxyprop-1-en-2-yl)benzene, 2-(1-phenethoxyprop-1-en-2-yl)naphthalene, (2-phenethoxyvinyl)benzene, 2-(1-((3,7-dimethyloct-6-en-1-yl)oxy)prop-1-en-2-yl)naphthalene, 1-(4-(((Z)-hex-3-en-1-yl)oxy)-3-methylbut-3-en-1-yl)-4-methoxybenzene, (2-((2-pentylcyclopentylidene)methoxy)ethyl)benzene, (2-((2-heptylcyclopentylidene)methoxy)ethyl)benzene, (2-((2-methyl-4-(2,6,6-trimethylcyclohex-1-en-1-yl)but-1-en-1-yl)oxy)ethyl)benzene, 1-methoxy-4-(2-methyl-3-phenethoxyallyl)benzene, (2-((2-isopropyl-5-methylcyclohexylidene)methoxy)ethyl)benzene, 1-isopropyl-4-methyl-2-((2-pentylcyclopentylidene)methoxy)benzene, 2-methoxy-1-((2-methoxy-2-phenylvinyl)oxy)-4-propylbenzene, 2-ethoxy-1-((2-methoxy-2-phenylvinyl)oxy)-4-methylbenzene, 2-ethoxy-1-((2-ethoxy-2-phenylvinyl)oxy)-4-methylbenzene, 3-methoxy-4-((2-methoxy-2-phenylvinyl)oxy)benzaldehyde, 1-isopropyl-2-((2-methoxy-2-phenylvinyl)oxy)-4-methylbenzene, 4-allyl-2-methoxy-1-((2-methoxy-2-phenylvinyl)oxy)benzene, (1E,5E)-9-(phenethoxymethylene)cyclododeca-1,5-diene, 1-((2,6-dimethyloct-7-en-2-yl)oxy)-2-methylundec-1-ene, (3-methyl-4-(octyloxy)but-3-en-1-yl)benzene, 4-(4-((2-phenylprop-1-en-1-yl)oxy)phenyl)butan-2-one, 4-allyl-2-methoxy-1-((2-methylundec-1-en-1-yl)oxy)benzene, 1-((2-ethyl-4,4-dimethylcyclohexylidene)methoxy)-2-methoxy-4-propylbenzene, 2-methoxy-1-((2-pentylcyclopentylidene)methoxy)-4-propylbenzene, 4-allyl-2-methoxy-1-((4-(tert-pentyl)cyclohexylidene)methoxy)benzene, methyl 2-((2-methoxy-2-phenylvinyl)oxy)benzoate, methyl 3-methoxy-4-((2-methoxy-2-phenylvinyl)oxy)benzoate, 2-ethoxy-1-((2-methoxy-2-phenylvinyl)oxy)-4-(methoxymethyl)benzene, (Z)-hex-3-en-1-yl 2-((2-methoxy-2-phenylvinyl)oxy)benzoate, 1-((2-butoxy-2-phenylvinyl)oxy)-2-methoxy-4-propylbenzene, 2-methoxy-1-((2-methoxy-2-(4-methoxyphenyl)vinyl)oxy)-4-propylbenzene, 4-((2-(hexyloxy)-2-phenylvinyl)oxy)-3-methoxybenzaldehyde, methyl 4-((2-(hexyloxy)-2-phenylvinyl)oxy)-3-methoxybenzoate, (Z)-hex-3-en-1-yl 2-((2-(((Z)-hex-3-en-1-yl)oxy)-2-phenylvinyl)oxy)benzoate and a mixture thereof.

In a particular embodiment, the invention's composition comprises at least two, even at least three pro-perfume compounds of formula (IV).

In an alternative embodiment, one of the at least two pro-perfume compounds to be used in the present invention, preferably the second pro-perfume compound, is a compound of formula (V)

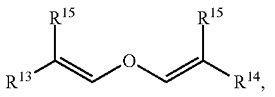

wherein $R^{13}$ and $R^{14}$ are identical or different and represent each a $C_2$ to $C_{15}$ hydrocarbon group optionally comprising an oxygen atom and both $R^{15}$ represent, independently from each other, a hydrogen atom or a methyl group.

In a particular embodiment, one of the at least two pro-perfume compounds, preferably the second pro-perfume compound, is selected from the group consisting of 1-(dodec-1-en-1-yloxy)dodec-1-ene, 1-(undec-1-en-1-yloxy)undec-1-ene, 2-methyl-1-((2-methylundec-1-en-1-yl)oxy)undec-1-ene, 2-methyl-1-((2-methyldec-1-en-1-yl)oxy)dec-1-ene, 1-(undeca-1,9-dien-1-yloxy)undeca-1,9-diene, and 1-(undeca-1,10-dien-1-yloxy)undeca-1,10-diene.

In an alternative embodiment, one of the at least two pro-perfume compounds to be used in the present invention, preferably the second pro-perfume compound, is a compound of formula (VI)

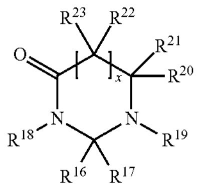

characterized in that:

x represents an integer varying between 0 and 3;

$R^{16}$ and $R^{17}$ are the residues of an aldehyde of formula $R^{16}CHO$ (with $R^{17}$ being a hydrogen atom) or of a ketone of formula $R^{16}R^{17}CO$ (with both $R^{16}$ and $R^{17}$ not being a hydrogen atom), respectively, said aldehyde or ketone having a molecular weight comprised between 80 and 230 g/mol and having a perfuming, flavoring, masking, pharmaceutical, agrochemical, insect repellent or attractant, bactericide, insecticide and/or fungicide effect;

$R^{18}$ represents a hydrogen atom or a $C_1$-$C_4$ alkyl or alkenyl group optionally substituted by one group of formula $COOR^{24}$, $R^{24}$ representing a hydrogen atom or a $C_1$-$C_4$ alkyl or alkenyl group;

$R^{19}$ represents a hydrogen atom, or a $C_1$-$C_{12}$ alkyl, alkenyl or aryl group optionally comprising from 1 to 5 oxygen atoms;

$R^{20}$, $R^{21}$, $R^{22}$, $R^{23}$ represent, simultaneously or independently from each other, a hydrogen atom, or a $C_1$-$C_{12}$ alkyl, alkenyl or aryl group, optionally comprising from 1 to 5 oxygen atoms and/or one sulphur atom and/or one, two or three nitrogen atoms; $R^{19}$ and $R^{20}$, or $R^{22}$ and $R^{23}$, taken together, may form a $C_2$-$C_6$ alkanediyl or alkenediyl group optionally comprising one oxygen atom; if n is not 0, $R^{20}$ and $R^{21}$, taken together with the carbon atom to which they are bonded, may form a carbonyl group.

In a particular embodiment, the compound of formula (VI) is characterized in that x is equal to 0, $R^{18}$, $R^{19}$ and $R^{20}$ are hydrogen atoms and $R^{21}$ is a residue derived from an amino acid of formula $NH_2$—$CHR^{21}$—COOH, and in particular of a natural α-amino acid such as alanine, arginine, asparagine, cysteine, glutamate, glutamine, glycine, histidine, isoleucine, leucine, lysine, methionine, phenylalanine, proline, serine, threonine, tryptophane, tyrosine, valine, aspartic acid, glutamic acid or of an artificial α-amino acid selected from the group of norleucine, 2-phenylglycine, isoasparagine and isoglutamine.

In one embodiment, the aldehydes of formula $R^{16}CHO$ may be selected from the group consisting of benzaldehyde, 1,3-benzodioxol-5-carboxaldehyde (heliotropine), 3-(1,3-benzodioxol-5-yl)-2-methylpropanal, 3-butoxybenzaldehyde, decanal, 2,4-decadienal, 2-decenal, 4-decenal, 8-decenal, 9-decenal, 3-(6,6-dimethyl-bicyclo[3.1.1]hept-2-en- 2-yl)propanal, 2,4-dimethyl-3-cyclohexene-1-carbaldehyde (Triplal®, origin: International Flavors & Fragrances, New York, USA), 3,5-dimethyl-3-cyclohexene-1-carbaldehyde, 1-(3,3-dimethyl-1-cyclohexyl)-1-ethanone, 5,9-dimethyl-4, 8-decadienal, 4,8-dimethyl-4,9-decadienal, 2,6-dimethyl-5-heptenal (melonal), 3,7-dimethyl-2,6-octadienal (citral), 3,7-dimethyloctanal, 3,7-dimethyl-6-octenal (citronellal), (3,7-dimethyl-6-octenyl)acetaldehyde, 2-dodecenal, 3-dodecenal, 4-dodecenal, 3-ethoxy-4-hydroxybenzaldehyde (ethyl vanillin), 4-ethyl benzaldehyde, 3-(2- and 4-ethylphenyl)-2,2-dimethylpropanal, 2-furancarbaldehyde (furfural), 2,4-heptadienal, 4-heptenal, 2-hexenal, 3-hexenal, 2-hexyl-3-phenyl-2-propenal (hexylcinnamic aldehyde), 2-hydroxybenzaldehyde, 7-hydroxy-3,7-dimethyloctanal (hydroxycitronellal), 4-hydroxy-3-methoxybenzaldehyde (vanillin), 4- and 3-(4-hydroxy-4-methylpentyl)-3-cyclohexene-1-carbaldehyde (Lyral®, origin: International Flavors and Fragrances, New York, USA), 3-(4-isobutyl-2-methylphenyl)propanal, 3-(4-isobutylphenyl)propanal, 4-isopropylbenzaldehyde (cuminaldehyde), 3-(4-isopropylcyclohex-1-en-1-yl)propanal, 3-(3-isopropylphenyl)butanal, 3-(4-isopropylphenyl)-2-methylpropanal, 2-(4-isopropylphenyl)propanal, (4R)-1-p-menthene-9-carbaldehyde (Liminal®, origin: Firmenich SA, Geneva, Switzerland), 6-methoxy-2,6-dimethylheptanal (methoxymelonal), 8(9)-methoxy-tricyclo[5.2.1.0.(2,6)]decane-3(4)-carbaldehyde (Scentenal®, origin: Firmenich SA, Geneva, Switzerland), 4-methylbenzaldehyde (anisaldehyde), 2-methyldecanal, 2-(4-methylenecyclohexyl)propanal, 1-methyl-4-(4-methyl-3-pentenyl)-3-cyclohexen-1-carbaldehyde (Precyclemone® B, origin: International Flavors & Fragrances, New York, USA), 4-(4-methyl-3-pentenyl)-3-cyclohexene-1-carbaldehyde (Empetal, origin: Givaudan-Roure SA., Vernier, Switzerland), (4-methylphenoxy)acetaldehyde, (4-methylphenyl)acetaldehyde, 3-methyl-5-phenylpentanal (Phenexal®, origin: Firmenich SA, Geneva, Switzerland), 3-methyl-3-phenylpropanal, 2-(1-methylpropyl)-1-cyclohexanone, 2-methylundecanal, 2,4-nonadienal, 2,6-nonadienal, 2-nonenal, 3-nonenal, 6-nonenal, 8-nonenal, 4-(octahydro-5H-4, 7-methanoinden-5-ylidene)butanaloctanal, 2-octenal, phenoxyacetaldehyde, phenylacetaldehyde, 3-phenylbutanal, 2-phenylpropanal (hydratropaldehyde), 3-phenyl-2-propenal (cinnamic aldehyde), 3-(4-tert-butylphenyl)-2-methylpropanal (Lilial®, origin: Givaudan-Roure SA, Vernier, Switzerland), 3-(4-tert-butylphenyl)propanal (Bourgeonal®, origin: Quest International, Naarden, Netherlands), tricyclo[5.2.1.0(2,6)]decane-4-carbaldehyde, exo-tricyclo[5.2.1.0(2,6)]decane-8exo-carbaldehyde (Vertral®, origin: Symrise, Holzminden, Germany), 2,6,6-trimethyl-bicyclo[3.1.1]heptane-3-carbaldehyde (formyl pinane), 2,6, 6-trimethylcyclohexa-1,3-diene-1-carbaldehyde (safranal), 2,4,6- and 3,5,6-trimethyl-3-cyclohexene-1-carbaldehyde, 2,2,3-trimethyl-3-cyclopentene-1-acetaldehyde (campholenic aldehyde), 2,6,10-trimethyl-2,6,9,11-dodecatetraenal, 2,5,6-trimethyl-4-heptenal, 3,5,5-trimethylhexanal, 2,6,10-trimethyl-9-undecenal, 2-undecenal, 10-undecenal or 9-undecenal and their mixtures such as Intreleven aldehyde (origin: International Flavors & Fragrances, New York, USA) and Aldehyde Supra (origin: Firmenich SA, Geneva, Switzerland) and 4-vinylcyclohex-1-ene-1-carbaldehyde.

In one embodiment, the ketones of formula $R^{16}R^{11}CO$ may be selected from the group consisting of 4-(1,3-benzodioxol-5-yl)-2-butanone, 2-butanone, (4E/Z,8E/Z)-cyclododeca-4,8-dien-1-one, 2-cyclohexyl-4-methyl-2-pentanone, cyclopentadecanone, (Z)-cyclopentadec-4-en-1-one, (Z)-cycloheptadec-9-en-1-one, 1-(3,3-dimethylcyclohexyl)ethan-1-one, 2,5-dimethyl-2-octen-6-one, 4,7-dimethyl-6-octen-3-one, 2,6-dimethyl-7-octen-4-one (dihydrotagetone), 4-(1,1-dimethylpropyl)cyclohexan-1-one, (5-E/Z)-6,10-dimethylundeca-5,9-dien-2-one, 2-ethyl-4,4-dimethylcyclohexan-1-one, 4-ethyl-8-methyloctahydronaphthalen-1(2H)-one, 2-heptanone, 3-heptanone, 2-heptylcyclopentan-1-one, 4,4a,6,7,8,8a-hexahydro-1,4-methanonaphthalen-5(1H)-one, 2-hexanone, 2-(hex-5-en-1-yl) ndecane din-1-one, 4-(4-hydroxy-3-methoxyphenyl)-2-butanone (zingerone), 4-(4-hydroxyphenyl)-2-butanone, 1-isopropyl-4-methylbicyclo[3.1.0]hexan-3-one, 5-isopropyl-2-methylcyclohexan-1-one, 2-isopropyl-5-methylcyclohexan-1-one (menthone), 1-(5-isopropyl-2-methylcyclohex-2-en-1-yl)propan-1-one, 4-(4-methoxyphenyl)-2-butanone, 7-methyl-2H-benzo[b][1,4]dioxepin-3(4H)-one, 2-(2-(4-methylcyclohex-3-en-1-yl)propyl) ndecane din-1-one, 3-methylcyclopentadecan-1-one, 3-methylcyclopentadec-4-en-1-one, 3-methylcyclopentadec-5-en-1-one, 5-methyl-3-heptanone, 6-methyl-5-hepten-2-one, 7-methyloctahydro-1,4-methanonaphthalen-6(2H)-one, methyl (Z)-2-(3-oxo-2-(pent-2-en-1-yl)cyclopentyl)acetate (methyl jasmonate), methyl 2-(3-oxo-2-pentylcyclopentyl)acetate, 1-(4-methyl-1-phenoxy)-2-propanone, 2-(1-methylpropyl)cyclohexan-1-one, 2-nonanone, 4-nonanone, 1-(octahydro-2,3,8,8-tetramethyl-2-naphthalenyl)-1-ethanone (isomeric mixture, Iso E Super®, origin: International Flavors & Fragrances, New York, USA), 2-octanone, 3-octanone, oct-2-en-4-one, 2-pentadecanone, 2-pentanone, 2-pentylcyclopentan-1-one, 4-phenyl-2-butanone, 7-propyl-2H-benzo[b][1,4]dioxepin-3(4H)-one, 1-(5-propylbenzo[d][1,3]dioxol-2-yl)ethan-1-one, 2-(tert-butyl)cyclohexan-1-one, 4-(tert-butyl)cyclohexan-1-one, 2-undecanone, 5-undecanone, 3,6,8,8-tetramethylhexahydro-1H-3a,7-methanoazulen-5(4H)-one, 1,1,5,5-tetramethylhexahydro-2H-2,4a-methanonaphthalen-8(5H)-one (iso-longifolanone), 2,4a,8,8-tetramethyloctahydrocyclopropa[d]naphthalen-3(1H)-one (thujopsan-4-one), 2,2,7,9-tetramethylspiro[5.5]undec-7-en-1-one, 2-tridecanone, 1,3,3-trimethylbicyclo[2.2.1]heptan-2-one, 1,7,7-trimethylbicyclo[2.2.1]heptan-2-one, 2,2,4-trimethylbicyclo[3.1.1]heptan-3-one, 2,6,6-trimethylcycloheptan-1-one, 2,2,6-trimethylcyclohexan-1-one, 4-(2,6,6-trimethylcyclohex-2-en-1-yl)butan-2-one (dihydro-alpha-ionone), 4-(2,6,6-trimethylcyclohex-1-en-1-yl)butan-2-one (dihydro-beta-ionone) and 2,2,5-trimethyl-5-pentylcyclopentan-1-one.

In a particular embodiment, the second pro-perfume compound is a compound of formula (VI), wherein $R^{16}$ and $R^{17}$ are the residues of a ketone of formula $R^{16}R^{17}CO$. In a preferred embodiment, the ketone of formula $R^{16}R^{17}CO$ is selected from the group of 4-(4-hydroxyphenyl)-2-butanone, 5-methyl-3-heptanone and 2-isopropyl-5-methylcyclohexan-1-one.

In a particular embodiment, one of the at least two pro-perfume compounds, preferably the second pro-perfume compound, is selected from the group consisting of 2-(6-hydroxy-2,6-dimethylheptyl)imidazolidin-4-one, 5-benzyl-2-nonylimidazolidin-4-one, 3-benzyl-6-isopropyl-9-methyl-1,4-diazaspiro[4.5]decan-2-one, 2-isopropyl-5-methyltetrahydrospiro[cyclohexane-1,3'-pyrrolo[1,2-c]imidazol]-1'(2'H)-one, 6-isopropyl-9-methyl-1,4-diazaspiro[4.5]decan-2-one and 2-ethyl-2-(2-methylbutyl)imidazolidine-4-one.

In an alternative embodiment, one of the at least two pro-perfume compounds to be used in the present invention, preferably second pro-perfume compound, is a compound of formula (VII)

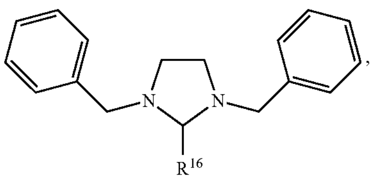

wherein $R^{16}$ is the residue of an aldehyde formula $R^{16}CHO$ as defined above.

In a particular embodiment, the second pro-perfume compound is a compound of formula (VII), wherein $R^{16}$ is the residue of an aldehyde $R^{16}CHO$ selected from the group of benzaldehyde, 2,6-dimethyl-5-heptenal, 2-methylundecanal, 3-methyl-3-phenylpropanal, 3-(4-isopropylphenyl)-2-methylpropanal and 2,4-dimethyl-3-cyclohexene-1-carbaldehyde.

In a particular embodiment, one of the at least two pro-perfume compounds, preferably the second pro-perfume compound, is selected from the group consisting of 1,3-dibenzyl-2-phenylimidazolidine, 1,3-dibenzyl-2-(undecane-2-yl)imidazolidine and 1,3-dibenzyl-2-(phenylpropyl)imidazolidine.

In an alternative embodiment, one of the at least two pro-perfume compounds to be used in the present invention, preferably second pro-perfume compound is a compound of formula (VIII)

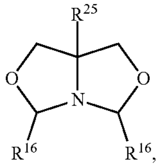

wherein $R^{16}$ is the residue of an aldehyde formula $R^{16}CHO$ as defined above and; $R^{25}$ is a hydrogen atom or a methyl or ethyl group.

In a particular embodiment, the second pro-perfume compound is a compound of formula (VIII), wherein $R^{16}$ is the residue of an aldehyde $R^{16}CHO$ selected from the group of 2,6-dimethyl-5-heptenal, octanal, decanal, 4,8-dimethyl-4,9-decadienal, 3-methyl-3-phenylpropanal, 3-(4-isobutyl-2-methylphenyl)propanal, 3-(4-isopropylphenyl)-2-methylpropanal, 2-methylundecanal and 2,4-dimethyl-3-cyclohexene-1-carbaldehyde, and wherein $R^{25}$ is a hydrogen atom.

In a particular embodiment, one of the at least two pro-perfume compounds, preferably the second pro-perfume compound, is selected from the group consisting of 3,5-bis(1-(4-isopropylphenyl)propan-2-yl)dihydro-1H,3H,5H-oxazolo[3,4-c]oxazole, 3,5-bis(2,4-dimethylcyclohex-3-en-1-yl)dihydro-1H,3H,5H-oxazolo[3,4-c]oxazole and 3,5-di(undecane-2-yl)dihydro-1H,3H,5H-oxazolo[3,4-c]oxazole.

In an alternative embodiment, one of the at least two pro-perfume compounds to be used in the present invention, preferably the second pro-perfume compound, is a compound of formula (IX)

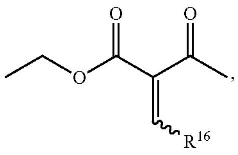

wherein $R^{16}$ is the residue of an aldehyde formula $R^{16}CHO$ as defined above.

In a particular embodiment, the pro-perfume compound of formula (IX) is characterized in that $R^{16}$ is the residue of an aldehyde $R^{16}CHO$, with the aldehyde being selected from the group consisting of decanal, 8-decenal, 2,6-dimethyl-5-heptenal, 2-dodecenal, 3-(4-isobutyl-2-methylphenyl)propanal, 3-(4-isobutylphenyl)propanal, 3-(4-isopropylcyclohex-1-en-1-yl)propanal, 3-(3-isopropylphenyl)butanal, 2-methyldecanal, 2-methylundecanal, 2,6-nonadienal and 3-(4-tert-butylphenyl)propanal.

In a particular embodiment, one of the at least two pro-perfume compounds, preferably the second pro-perfume compound, is ethyl 2-acetyl-4-methyltridec-2-enoate.

In an alternative embodiment, the perfuming composition comprises a pro-perfume compound releasing a perfume compound upon exposure to light.

In a particular embodiment, the perfuming composition comprises a first pro-perfume compound releasing a perfume compound upon exposure to air/oxygen and/or moisture and a second pro-perfume compound releasing a perfume compound upon exposure to light, wherein the first and second pro-perfume compounds are structurally different types of pro-perfume compounds.

In a particular embodiment, one of the at least two pro-perfume compounds to be used in the present invention, preferably the second pro-perfume compound, is a pro-perfume compound according to formula (X)

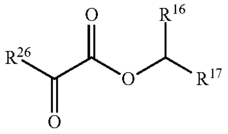

wherein, $R^{26}$ represents a linear, branched or cyclic, saturated or unsaturated $C_1$-$C_{16}$ hydrocarbon group, and $R^{16}$ and $R^{17}$ are the residues of an aldehyde of formula $R^{16}CHO$ or of a ketone of formula $R^{16}R^{17}CO$ as defined before.

In a particular embodiment, the pro-perfume compound is of formula (X), wherein $R^{26}$ represents a linear or branched $C_1$ to $C_4$ alkyl or alkenyl group, or a cyclic $C_3$ to $C_7$ alkyl or alkenyl group, or a phenyl group, optionally substituted with a $C_1$ to $C_4$ alkyl group, even more preferably $R^{26}$ represents a methyl group or a phenyl group, most preferably $R^{26}$ represents a phenyl group, and wherein $R^{16}$ in formula (X) is derived from a $C_6$ to $C_{12}$ perfumery aldehyde of formula $R^{16}CHO$, preferably the perfumery aldehyde of formula $R^{16}CHO$ is selected from the group consisting of benzaldehyde, 2,4-dimethyl-3-cyclohexene-1-carbaldehyde, 2,6-dimethyl-5-heptenal (melonal), 3,7-dimethyl-2,6-octadienal (citral), 3,7-dimethyl-6-octenal (citronellal), decanal, 4-dodecenal, 2-hexenal, 3-hexenal, 7-hydroxy-3,7-dimethyloctanal, 2-methylundecanal and 2-phenylacetaldehyde.

In a particular embodiment, one of the at least two pro-perfume compounds, preferably the second pro-perfume compound, is selected from the group consisting of 2-phenylethyl 2-oxo-2-phenylacetate, decyl 2-oxo-2-phenylacetate, (Z)-3-hexenyl 2-oxo-2-phenylacetate, 2,6-dimethyl-5-heptenyl 2-oxo-2-phenylacetate, 3,7-dimethylocta-2,6-dienyl 2-oxo-2-phenylacetate, (Z)-dodec-4-en-1-yl 2-oxo-2-phenylacetate, (2,4-dimethylcyclohex-3-en-1-yl)methyl 2-oxo-2-phenylacetate and 2-isopropyl-5-methylcyclohexyl 2-oxo-2-phenylacetate.

In a particular embodiment, the compound of formula (X) may be encapsulated. The compound of formula (X) can be encapsulated in a microcapsule. Preferably, it is encapsulated in a core-shell microcapsule wherein the compound of formula (X) is contained in the core surrounded by the shell. The shell of the microcapsule protects the encapsulated compound of formula (X) from the environment. The shell is made of material, which is able to release the perfuming composition according to the invention. Preferably, the shell is made of material, which is able to release the perfuming composition according to the invention upon breakage of the shell and/or by diffusion through the shell. A person skilled in the art is well aware of processes to prepare said microcapsules.

Optionally, the compound of formula (X) is encapsulated together with a suitable solvent, a perfume or an essential oil.

In an alternative embodiment, one of the at least two pro-perfume compounds to be used in the present invention, preferably the second pro-perfume compound, is a pro-perfume compound according to formula (XI)

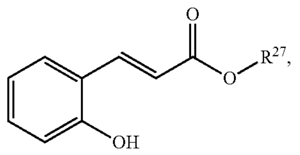

wherein $R^{27}$ is derived from a $C_{6-20}$ alcohol of formula $R^{27}OH$, said alcohol having a molecular weight comprised between 80 and 230 g/mol and having a perfuming, flavoring, masking, pharmaceutical, agrochemical, insect repellent or attractant, bactericide, insecticide and/or fungicide effect.

In one embodiment, the alcohols of formula $R^{27}OH$ may be selected from the group consisting of 4-allyl-2-methoxyphenol (eugenol), 3-benzyl-3-pentanol, butanol, 4-cyclohexyl-2-methylbutan-2-ol (origin: Firmenich SA, Geneve, Switzerland), 2-cyclohexylpropanol, decanol, 9-decen-1-ol (Rosalva, origin: International Flavors and Fragrances, New York, USA), (2,4-dimethylcyclohex-3-enyl)methanol, (2,4-dimethylcyclohexyl)methanol, 2-(1,1-dimethylethyl)-4-methylcyclohexanol, 2,6-dimethylheptan-2-ol, 3,7-dimethyl-7-hydroxyoctanal, 3,7-dimethyl-1,6-nonadien-3-ol, 6,8-dimethylnonan-2-ol, 4,8-dimethyl-7-nonen-2-ol, (E)-3,7-dimethyl-2,6-octadienol (geraniol), (Z)-3,7-dimethyl-2,6-octadienol (nerol), 3,7-dimethyl-3,6-octadienol, 3,7-dimethyl-1,6-octadien-3-ol (linalool), 3,7-dimethyloctane-1,7-diol (hydroxycitronellol), 3,7-dimethyloctanol, 2,6-dimethyloctan-2-ol (tetrahydromyrcenol), 3,7-dimethyloctan-3-ol, 3,7-dimethyl-6-octenol (citronellol), 3,7-dimethyloct-7-enol, 2,6-dimethyloct-7-en-2-ol (dihydromyrcenol), (E)-3,3-dimethyl-5-(2,2,3-trimethyl-3-cyclopenten-1-yl)-4-penten-2-ok (Polysantol®, origin: Firmenich SA, Geneve, Switzerland), dodecanol, 1,8-epoxy-p-menthane (eucalyptol), 3-ethoxy-4-hydroxybenzaldehyde (ethyl vanillin), 2-ethyl-1-hexanol, ethyl 3-hydroxyhexanoate, 2-ethyl-3-hydroxy-4H-pyran-4-one, 6-ethyl-3-methyl-5-octenol, 5-ethylnonan-2-ol, 2-ethyl-4-(2,2,3-trimethylcyclopent-3-enyl)but-2-enol, 1 heptanol, hexanol, hexan-2-ol, 2-hexenol, 3-hexenol, 4-hexenol, 3-hydroxybutan-2-one, 4-hydroxy-3-ethoxybenzaldehyde (ethylvanillin), 4-hydroxy-3-methoxybenzaldehyde (vanillin), 4-(4-hydroxy-3-methoxyphenyl)butan-2-one, 2-(hydroxymethyl)nonan-2-one, 4-(4-hydroxyphenyl)butan-2-one (raspberry ketone), 4-isopropylcyclohexanol, 1-(4-isopropyl-1-cyclohexyl) ethanol, (4-isopropyl-1-cyclohexyl)methanol, (4-isopropylphenyl)methanol, 7 p-menthanol (Mayol®, origin: Firmenich SA, Geneve, Switzerland), p-menthan-3-ol, p menthan-8-ol, p-menthen-4-ol, p-menthen-8-ol, p-menth-8-enol, p-menth-8-en-2-ol, p-menth-8-en-3-ol, 7-methoxy-3,7-dimethyloctan-2-ol, 2-methoxyphenol, 2-methoxy-2-phenylethanol, (4-methoxyphenyl)methanol (anisyl alcohol), 2-methoxy-4-(1-propenyl)phenol (isoeugenol), 2-methoxy-4-propyl-1-cyclohexanol (Tarragol®, origin: Firmenich SA, Geneve, Switzerland), 2-methoxy-4-propylphenol, 3-(4-methylcyclohex-3-enyl)butanol, 4-methyl-3-decenol, 4-methyl-3-decen-5-ol (origin: Givaudan SA, Genève, Switzerland), 4-(1-methylethyl)cyclohexylmethanol, 2-methyl-4-phenylbutan-2-ol, 3-methyl-4-phenylbutan-2-ol, 1-(4-methylphenyl)ethanol, 2-(2-methylphenyl)ethanol, 2 methyl-4-phenylpentanol, 2-methyl-5-phenylpentanol, 3-methyl-5-phenylpentanol (phenylhexanol, origin: Firmenich SA, Geneve, Switzerland), 4-methyl-1-phenylpentan-2-ol, 2-methyl-1-phenylpropan-2-ol, 2-(4-methylphenyl)propan-2-ol, 3-methyl-5-(2,2,3-trimethyl-3-cyclopenten-1-yl)-4-penten-2-ol (Ebanol®, origin: Givaudan SA, Geneve, Switzerland), 2-(2-methylpropyl)-4-hydroxy-4-methyl-tetrahydropyrane, 2-methyl-4-(2,3,3-trimethyl-2-cyclopenten-1-yl)-2-butenol (Santaliff®, origin: International Flavors and Fragrances, New York, USA), 3-methyl-5-(2,2,3-trimethylcyclopentyl-3-enyl)pent-4-en-2-ol, 2,6-nonadienol, 1-nonanol, 6-nonenol, 1,2,3,4,4a,5,8,8a-octahydro-2,2,6,8-tetramethyl-1-naphthalenol, octanol, octan-2-ol, octan-3-ol, 1-octen-3-ol, 3,4,5,6,6-pentamethylheptan-2-ol (Kohinool®, origin: International Flavors and Fragrances, New York, USA), 2-pentyl-1-cyclopentanol, perhydro-4,8a-dimethyl-4a-naphthalenol, 2 phenoxyethanol, 4-phenylbutan-2-ol, 4-phenyl-3-buten-2-ol, 1-phenylethanol, 2 phenylethanol, 1-phenylhexan-2-ol, 1-phenylpentan-2-ol, 2-phenylpropanol, 2 phenylpropanol, 3-phenylpropanol, 1-phenylpropan-2-ol, 3-phenyl-2-propenol, 2-tert-butylcyclohexanol (Verdol, origin International Flavors and Fragrances, New York, USA), 4-tert-butylcyclohexanol, 1-(2-tert-butyl-cyclohexyloxy)butan-2-ol, 2-tert-butyl-4-methyl-1-cyclohexanol, tetrahydro-2-isobutyl-4-methyl(2H)pyran-4-ol (Florol®, origin: Firmenich SA, Geneve, Switzerland), 2-(tetrahydro-5-methyl-5-vinyl-2-furyl)propan-2-ol, 1-(2,2,3,6-tetramethylcyclohex-1-yl)hexan-3-ol (Limbanol®, origin: Firmenich SA, Geneve, Switzerland), 2,6,10,10-tetramethyl-1-oxaspiro[4.5]decan-6-ol, 2,6,6,8-tetramethyltricyclo [5.3.1.0(1,5)]undecan-8-ol (cedrenol), (+)-(1R,2R)-1,3,3-trimethylbicyclo[2.2.1]heptan-2endo-ol (fenchol), (+)-(1R,2S)-1,7,7-trimethylbicyclo[2.2.1]heptan-2-ol (borneol), 2,6, 6-trimethylbicyclo[3.1.1]heptan-3-ol, 3-(5,5,6-trimethylbicyclo[2.2.1]hept-2-yl)cyclohexanol (Sandela®, origin: Givaudan SA, Geneve, Switzerland), 4-(5,5,6-trimethylbicyclo[2.2.1]hept-2-yl)cyclohexanol, 3,3,5-trimethylcyclohexanol, 4-(2,6,6-trimethyl-2-cyclohexen-1-yl)butan-2-ol, 4-(2,6,6-trimethyl-1-cyclohexen-1-yl)-3-buten-2-ol (beta-ionol), (E)-4-(2,6,6-trimethyl-2-cyclohexen-1-yl)-3-buten-2-ol (alpha-ionol), (2,4,6-trimethylcyclohex-3-enyl) methanol, 1 (2,2,6-trimethyl-1-cyclohexyl)hexan-3-ol, 5-(2,2,3-trimethyl-3-cyclopentenyl)-3-methylpentan-2-ol, 3,7,11-trimethyl-2,6,10-dodecatrienol (farnesol), 3,7,11-trimethyl-1,6,10-dodecatrien-3-ol (nerolidol), 3,3,5-trimethylhexanol, undecanol, undecan-2-ol and 10-undecenol.

In a particular embodiment, the pro-perfume compound is a compound of formula (XI), wherein $R^{27}$ is the residue of a perfuming alcohol of formula $R^{27}OH$, with the alcohol being selected from the group consisting of 9-decen-1-ol, 3,7-dimethyl-1,6-octadien-3-ol, 3,7-dimethyl-6-octenol, 3-hexenol and 3-methyl-5-phenylpentanol.

In a particular embodiment, one of the at least two pro-perfume compounds, preferably the second pro-perfume compound, is dec-9-en-1-yl (E)-3-(2-hydroxyphenyl)acrylate.

In an alternative embodiment, the perfuming composition comprises a pro-perfume compound releasing a perfume compound upon exposure to heat.

In a particular embodiment, the perfuming composition comprises a first pro-perfume compound releasing a perfume compound upon exposure to light, air/oxygen and/or moisture and a second pro-perfume compound releasing a perfume compound upon exposure to heat, wherein the first and second pro-perfume compounds are structurally different types of pro-perfume compounds.

In a particular embodiment, one of the at least two pro-perfume compounds to be used in the present invention, preferably the second pro-perfume compound, is a pro-perfume compound according to formula (XII)

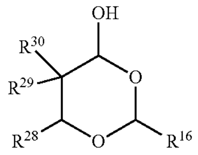

wherein $R^{16}$ represents the residue of an aldehyde of formula $R^{16}CHO$ as defined before; $R^{28}$ represents a $R^{16}$ group, a Z group or a $C_5$ to $C_{10}$ aromatic ring, said ring possibly comprising up to three oxygen or nitrogen atoms and being possibly substituted, and Z being a hydrogen atom, a $C_1$ to $C_{20}$ linear, branched, cyclic or poly-cyclic saturated, unsaturated, aromatic or alkylaryl hydrocarbon radical, said hydrocarbon radical possibly comprising up to three oxygen or nitrogen atoms and being possibly substituted; two Z being possibly bonded together to form a saturated, unsaturated or aromatic ring having 5 to 20 carbon atoms, said ring being possibly substituted; and $R^{29}$ and $R^{30}$ represent each a Z group or are bonded together to form a saturated or unsaturated ring having 5 to 20 carbon atoms, said ring being possibly substituted; and a perfume or flavor base; provided that muscat wine extracts are excluded.

In a particular embodiment, the pro-perfume compound is a compound of formula (XII), wherein $R^{16}$ is the residue of a perfuming or flavoring aldehyde of formula $R^{16}CHO$ selected from the group consisting of octanal, decanal, dodecanal, 3-phenylbutanal, 2-phenylacetaldehyde and 3-(4-tert-butylphenyl)propanal.

In a particular embodiment, one of the at least two pro-perfume compounds, preferably the second pro-perfume compound, is selected from the group consisting of 5-butyl-2-heptyl-6-pentyl-1,3-dioxan-4-ol, 5-butyl-2-nonyl-6-pentyl-1,3-dioxan-4-ol, 5-butyl-6-pentyl-2-undecyl-1,3-dioxan-4-ol, 5-butyl-6-pentyl-2-(2-phenylpropyl)-1,3-dioxan-4-ol, 2-benzyl-5-butyl-6-pentyl-1,3-dioxan-4-ol and 5-butyl-2-(4-(tert-butyl)phenethyl)-6-pentyl-1,3-dioxan-4-ol.

In an alternative embodiment, the perfuming composition comprises a pro-perfume compound releasing a perfume compound upon hydrolysis, in particular upon exposure to enzymes (enzyme-catalyzed hydrolysis).

In a particular embodiment, the perfuming composition comprises a first pro-perfume compound releasing a perfume compound upon exposure to light, air/oxygen and/or moisture and a second pro-perfume compound releasing a perfume compound upon exposure to enzymes, wherein the first and second pro-perfume compounds are structurally different types of pro-perfume compounds.

In a particular embodiment, one of the at least two pro-perfume compounds to be used in the present invention, preferably the second pro-perfume compound, is a pro-perfume compound according to formula (XIII)

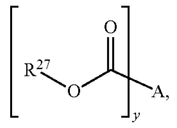

wherein y is either 1 or 2,

A is an y-valent $C_{1-22}$ hydrocarbon group, and $R^{27}$ is derived from a $C_{6-20}$ perfuming alcohol of formula $R^{27}OH$ as defined above.

In a particular embodiment, the y-valent $C_{1-22}$ hydrocarbon group A in formula (XIII) is preferably derived from lauric acid, myristic acid, palmitic acid, stearic acid and oleic acid (for y=1) or from malonic acid, succinic acid, glutaric acid, adipic acid or sebacic acid (for y=2).

In a particular embodiment, preferred perfuming alcohols of formula $R^{27}OH$ comprise 2-hexenol, 3-hexenol, 3,7-dimethyl-6-octenol, 3,7-dimethyl-2,6-octadienol, 9-decen-1-ol, 3-methyl-5-phenylpentanol, 3,7,11-trimethyl-2,6,10-dodecatrienol, 2-ethyl-4-(2,2,3-trimethylcyclopent-3-enyl) but-2-enol, 4-(4-hydroxyphenyl)butan-2-one, 4-hydroxy-3-methoxybenzaldehyde, 3-ethoxy-4-hydroxybenzaldehyde or 2-ethyl-3-hydroxy-4H-pyran-4-one.

In a particular embodiment, one of the at least two pro-perfume compounds, preferably the second pro-perfume compound, is selected from the group consisting of 3-methyl-5-phenylpentyl palmitate, (2E)-3,7-dimethyl-2,6-octadien-1-yl-hexadecanoate (geranyl palmitate) and bis ((2E)-3,7-dimethylocta-2,6-dien-1-yl) succinate (digeranyl succinate).

In an alternative embodiment, the perfuming composition comprises a pro-perfume compound releasing a perfume compound upon exposure to air/oxygen.

In a particular embodiment, the perfuming composition comprises a first pro-perfume compound releasing a perfume compound upon exposure to light, air/oxygen, enzymes and/or moisture and a second pro-perfume compound releasing a perfume compound upon exposure to air/oxygen, wherein the first and second pro-perfume compounds are structurally different types of pro-perfume compounds.

In a particular embodiment, one of the at least two pro-perfume compounds to be used in the present invention, preferably the second pro-perfume compound, is a pro-perfume compound according to formula (XIV)

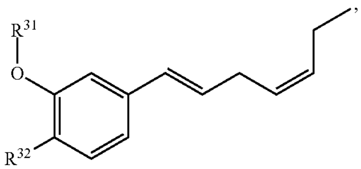

, wherein $R^{31}$ is a hydrogen atom or a $C_{1-6}$ hydrocarbon group, preferably a $C_{1-6}$ alkyl group, even more preferably a $C_{1-4}$ alkyl group, and $R^{32}$ is a hydrogen atom, a hydroxy group or a methoxy group.

In a particular embodiment, one of the at least two pro-perfume compounds, preferably the second pro-perfume compound, is selected from the group consisting of 1-butoxy-3-((1E,4Z)-hepta-1,4-dien-1-yl)benzene, 2-methoxy-4-((1E,4Z)-hepta-1,4-dien-1-yl)phenol or 2-ethoxy-4-((1E,4Z)-hepta-1,4-dien-1-yl)phenol.

In a particular embodiment, one of the at least two pro-perfume compounds to be used in the present invention, preferably the second pro-perfume compound, is a pro-perfume compound according to formula (XV)

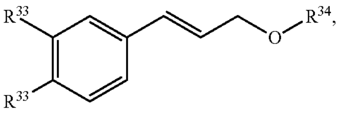

, wherein $R^{33}$ is, independently, a hydrogen atom, hydroxyl group, a $C_1$-$C_6$ hydrocarbon group, a $C_1$-$C_6$ alkoxy group, $—O(C{=}O)CH_3$ and $—O(C{=}O)CH(CH_3)_2$; the two $R^{33}$ groups when taken together may form a $—OCH_2O—$ group, and $R^{34}$ represents a $C_3$-$C_{20}$ hydrocarbon group.

In a particular embodiment, one of the at least two pro-perfume compounds, preferably the second pro-perfume compound, is selected from the group consisting of (3-((2,6-dimethyloct-7-en-2-yl)oxy)prop-1-en-1-yl)benzene, 1-(3-(2,6-dimethyloct-7-en-2-yloxy)prop-1-enyl)-4-methoxybenzene, 1-(3-(2,6-dimethyloctan-2-yloxy)prop-1-enyl)-4-methoxybenzene, 1-(3-(3,7-dimethylocta-1,6-dien-3-yloxy)prop-1-enyl)-4-methoxybenzene, 1-(3-(3,7-dimethyloct-1-en-3-yloxy)prop-1-enyl)-4-methoxybenzene, 1-(3-((3,7-dimethyloctan-3-yl)oxy)prop-1-en-1-yl)-4-methoxybenzene, 1-(3-((3,7-dimethyloctan-3-yl)oxy)prop-1-en-1-yl)-4-methoxybenzene, 1-(3-((2,6-dimethyloct-7-en-2-yl)oxy)prop-1-en-1-yl)-4-ethylbenzene, 4-(3-((2,6-dimethyloct-7-en-2-yl)oxy)prop-1-en-1-yl)-1,2-dimethoxybenzene, 4-(3-(((Z)-hex-3-en-1-yl)oxy)prop-1-en-1-yl)-2-methoxyphenol, 4-(3-((3,7-dimethyloct-6-en-1-yl)oxy)prop-1-en-1-yl)-2-methoxyphenol, 2-methoxy-4-(3-(undecan-2-yloxy)prop-1-en-1-yl)phenol, 2-methoxy-4-(3-(tert-pentyloxy)prop-1-en-1yl)phenol, 4-(3-((2,6,dimethyloct-7-en-2-yl)oxy)prop-1-en-1-yl)-2-methoxyphenol and 4-(3-((2,6-dimethyloctan-2-yl)oxy)prop-1-en-1-yl)-2-methoxyphenol.

According to any of the embodiments, the invention's perfuming composition comprises at least two structurally different types of pro-perfume compounds selected from the group consisting of pro-perfumes of formulae (I) and of formulae (III) to (XV). Preferably, the invention's perfuming composition comprises at least two structurally different types of pro-perfume compounds selected from the group consisting of pro-perfumes of formulae (I), (III) to (XIII) and (XV). Preferably, the invention's perfuming composition comprises at least two structurally different types of pro-perfume compounds selected from the group consisting of pro-perfumes of formulae (I), (III) to (VIII), (X) to (XV). Preferably, the invention's perfuming composition comprises at least two structurally different types of pro-perfume compounds selected from the group consisting of pro-perfumes of formulae (I), (III) to (VIII), (X) to (XIII) and (XV). Preferably, the invention's perfuming composition comprises at least two structurally different types of pro-perfume compounds selected from the group consisting of pro-perfumes of formulae a), b), c) or d) and of formulae (III) to (XV). Even more preferably, the invention's perfuming composition comprises at least two structurally different pro-perfume compounds selected from the group consisting of a pro-perfume compound of formula a), b), c) or d), a pro-perfume compound of formula (III), a pro-perfume compound of formula (IV), a pro-perfume compound of formula (VI), a pro-perfume compound of formula (VIII), a pro-perfume compound of formula (IX), a pro-perfume compound of formula (X), a pro-perfume compound of formula (XI) and a pro-perfume compound of formula (XIII). Most preferably, the invention's perfuming composition comprises at least two structurally different pro-perfume compounds selected from the group consisting of a pro-perfume compound of formula a), b), c) or d), a pro-perfume compound of formula (III), a pro-perfume compound of formula (IV), a pro-perfume compound of formula (VI), pro-perfume compound of formula (X) and pro-perfume compound of formula (XIII).

In another particular embodiment, the invention's perfuming composition comprises at least two structurally different types of pro-perfume compounds selected from the group consisting of pro-perfumes of formulas (III) to (XV). Preferably, the invention's perfuming composition comprises at least two structurally different types of pro-perfume compounds selected from the group consisting of pro-perfumes of formulas (III), (IV), (VIII), (IX), (X), (X), (XIII), (XIV) and (XV). Particularly, the invention's perfuming composition comprises at least one pro-perfume compound of formula (IV) and at least one pro-perfume compound selected from the group consisting of pro-perfumes of formulas (III) and (V) to (XV).

In a particular embodiment, the invention's perfuming composition does not comprise a mixture of ethyl (Z)-2-acetyl-4-methyltridec-2-enoate, ethyl N,S-bis(4-oxo-4-(2,6,6-trimethylcyclohex-3-en-1-yl)butan-2-yl)cysteinate and 4-(dodecylthio)-4-methylpentan-2-one and, optionally, 1-butoxy-3-((1E,4Z)-hepta-1,4-dien-1-yl)benzene and 2-ethoxy-4-((1E,4Z)-hepta-1,4-dien-1-yl)phenol.

In a particular embodiment, the perfuming composition according to the invention is partly or totally encapsulated. The perfuming composition according to the invention can be encapsulated in a microcapsule. Preferably, the perfuming composition according to the invention is encapsulated in a core-shell microcapsule wherein the perfuming composition according to the invention is contained in the core surrounded by the shell. The shell of the microcapsule protects the perfuming composition according to the invention from the environment. The shell is made of material, which is able to release the perfuming composition according to the invention. Preferably, the shell is made of material, which is able to release the perfuming composition according to the invention upon breakage of the shell and/or by diffusion through the shell. A person skilled in the art is well aware of processes to prepare said microcapsules.

In a particular embodiment, the perfuming composition according to the invention comprises a perfumery carrier.

By "perfumery carrier" it is meant here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples, solvents such as butylene or propylene glycol, glycerol, dipropyleneglycol and its monoether, 1,2,3-propanetriyl triacetate, dimethyl glutarate, dimethyl adipate 1,3-diacetyloxypropan-2-yl acetate, diethyl phthalate, isopropyl myristate, benzyl benzoate, benzyl alcohol, 2-(2-ethoxyethoxy)-1-ethano, tri-ethyl citrate or mixtures thereof, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company), or hydrogenated castors oils such as those known under the trademark Cremophor® RH 40 (origin: BASF).

Solid carrier is meant to designate a material to which the perfuming composition or some element of the perfuming composition can be chemically or physically bound. In general, such solid carriers are employed either to stabilize the composition, or to control the rate of evaporation of the compositions or of some ingredients. The use of solid carrier is of current use in the art and a person skilled in the art knows how to reach the desired effect. However, by way of non-limiting example of solid carriers, one may cite absorbing gums or polymers or inorganic material, such as porous polymers, cyclodextrins, wood based materials, organic or inorganic gels, clays, gypsum talc or zeolites.

As other non-limiting examples of solid carriers, one may cite encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs-und Geliermittel in Lebensmitteln, Band 2 der Schriftenreihe Lebensmittelchemie, Lebensmittelqualitst, Behr's Verlag GmbH & Co., Hamburg, 1996. The encapsulation is a well-known process to a person skilled in the art, and may be performed, for instance, by using techniques such as spray-drying, agglomeration or yet extrusion; or consists of a coating encapsulation, including coacervation and complex coacervation technique.

As non-limiting examples of solid carriers, one may cite in particular the core-shell capsules with resins of aminoplast, polyamide, polyester, polyurea or polyurethane type or a mixture thereof (all of said resins are well known to a person skilled in the art) using techniques like phase separation process induced by polymerization, interfacial polymerization, coacervation or altogether (all of said techniques have been described in the prior art), optionally in the presence of a polymeric stabilizer or of a cationic copolymer.

Resins may be produced by the polycondensation of an aldehyde (e.g. formaldehyde, 2,2-dimethoxyethanal, glyoxal, glyoxylic acid or glycolaldehyde and mixtures thereof) with an amine such as urea, benzoguanamine, glycoluryl, melamine, methylol melamine, methylated methylol melamine, guanazole and the like, as well as mixtures thereof. Alternatively one may use preformed resins alkylolated polyamines such as those commercially available under the trademark Urac© (origin: Cytec Technology Corp.), Cymel® (origin: Cytec Technology Corp.), Urecoll® or Luracoll® (origin: BASF).

Others resins one are the ones produced by the polycondensation of an a polyol, like glycerol, and a polyisocyanate, like a trimer of hexamethylene diisocyanate, a trimer of isophorone diisocyanate or xylene diisocyanate or a Biuret of hexamethylene diisocyanate or a trimer of xylene diisocyanate with trimethylolpropane (known with the tradename of Takenate®, origin: Mitsui Chemicals), among which a trimer of xylene diisocyanate with trimethylolpropane and a Biuret of hexamethylene diisocyanate.

Some of the seminal literature related to the encapsulation of perfumes by polycondensation of amino resins, namely melamine based resins with aldehydes includes represented by articles such as those published by K. Dietrich et al. Acta Polymerica, 1989, vol. 40, pages 243, 325 and 683, as well as 1990, vol. 41, page 91.

Such articles already describe the various parameters affecting the preparation of such core-shell microcapsules following prior art methods that are also further detailed and exemplified in the patent literature. U.S. Pat. No. 4,396,670, to the Wiggins Teape Group Limited, is a pertinent early example of the latter. Since then, many other authors have enriched the literature in this field and it would be impossible to cover all published developments here, but the general knowledge in encapsulation technology is very significant. More recent publications of pertinence, which disclose suitable uses of such microcapsules, are represented for example by the article of K. Bruyninckx and M. Dusselier, ACS Sustainable Chemistry & Engineering, 2019, vol. 7, pages 8041-8054.

In a particular embodiment, the perfuming composition according to the invention comprises a perfuming co-ingredient.

The perfuming co-ingredient is not a compound according to the invention. Moreover, the term "perfuming co-ingredient" is understood as a compound, which is used in a perfuming preparation or composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpene hydrocarbons, nitrogenous or sulphurous heterocyclic compounds and essential oils, and the perfuming co-ingredients can be of natural or synthetic origin. In particular, one may cite perfuming co-ingredients which are commonly used in perfume formulations, such as:

- Aldehydic ingredients: decanal, dodecanal, 2-methyl-undecanal, 10-undecenal, octanal, nonanal and/or nonenal;
- Aromatic-herbal ingredients: eucalyptus oil, camphor, eucalyptol, 5-methyltricyclo[6.2.1.0~2,7~]undecan-4-one, 1-methoxy-3-hexanethiol, 2-ethyl-4,4-dimethyl-1,3-oxathiane, 2,2,7/8,9/10-Tetramethylspiro[5.5]undec-8-en-1-one, menthol and/or alpha-pinene;
- Balsamic ingredients: coumarin, ethylvanillin and/or vanillin;
- Citrus ingredients: dihydromyrcenol, citral, orange oil, linalyl acetate, citronellyl nitrile, orange terpenes, limonene, 1-p-menthen-8-yl acetate and/or 1,4(8)-p-menthadiene;
- Floral ingredients: methyl dihydrojasmonate, linalool, citronellol, phenylethanol, 3-(4-tert-butylphenyl)-2-methylpropanal, hexylcinnamic aldehyde, benzyl acetate, benzyl salicylate, tetrahydro-2-isobutyl-4-methyl-4(2H)-pyranol, beta ionone, methyl 2-(methylamino)benzoate, (E)-3-methyl-4-(2,6,6-trimethyl-2-cyclohexen-1-yl)-3-buten-2-one, (1E)-1-(2,6,6-trimethyl-2-cyclohexen-1-yl)-1-penten-3-one, 1-(2,6,6-trimethyl-1,3-cyclohexadien-1-yl)-2-buten-1-one, (2E)-1-(2,6,6-trimethyl-2-cyclohexen-1-yl)-2-buten-1-one, (2E)-1-[2,6,6-trimethyl-3-cyclohexen-1-yl]-2-buten-1-one, (2E)-1-(2,6,6-trimethyl-1-cyclohexen-1-yl)-2-buten-1-one, 2,5-dimethyl-2-indanmethanol, 2,6,6-trimethyl-3-cyclohexene-1-carboxylate, 3-(4,4-dimethyl-1-cyclohexen-1-yl)propanal, hexyl salicylate, 3,7-dimethyl-1,6-nonadien-3-ol, 3-(4-isopropylphenyl)-2-methylpropanal, verdyl acetate, geraniol, p-menth-1-en-8-ol, 4-(1,1-dimethylethyl)-1-cyclohexyle acetate, 1,1-dimethyl-2-phenylethyl acetate, 4-cyclohexyl-2-methyl-2-butanol, amyl salicylate, high cis methyl dihydrojasmonate, 3-methyl-5-phenyl-1-pentanol, verdyl proprionate, geranyl acetate, tetrahydro linalool, cis-7-p-menthanol, propyl (S)-2-(1,1-dimethylpropoxy)propanoate, 2-methoxynaphthalene, 2,2,2-trichloro-1-phenylethyl acetate, 4/3-(4-hydroxy-4-methylpentyl)-3-cyclohexene-1-carbaldehyde, amylcinnamic aldehyde, 8-decen-5-olide, 4-phenyl-2-butanone, isononyle acetate, 4-(1,1-dimethylethyl)-1-cyclohexyl acetate, verdyl isobutyrate and/or mixture of methylionones isomers;
- Fruity ingredients: gamma-undecalactone, 2,2,5-trimethyl-5-pentylcyclopentanone, 2-methyl-4-propyl-1,3-oxathiane, 4-decanolide, ethyl 2-methyl-pentanoate, hexyl acetate, ethyl 2-methylbutanoate, gamma-nonalactone, allyl heptanoate, 2-phenoxyethyl isobutyrate, ethyl 2-methyl-1,3-dioxolane-2-acetate, 3-(3,3/1,1-dimethyl-5-indanyl)propanal, diethyl 1,4-cyclohexanedicarboxylate, 3-methyl-2-hexen-1-yl acetate, 1-[3,3-dimethylcyclohexyl]ethyl [3-ethyl-2-oxiranyl]acetate and/or diethyl 1,4-cyclohexane dicarboxylate;
- Green ingredients: 2-methyl-3-hexanone (E)-oxime, 2,4-dimethyl-3-cyclohexene-1-carbaldehyde, 2-tert-butyl-1-cyclohexyl acetate, styrallyl acetate, allyl (2-methylbutoxy)acetate, 4-methyl-3-decen-5-ol, diphenyl ether, (Z)-3-hexen-1-ol and/or 1-(5,5-dimethyl-1-cyclohexen-1-yl)-4-penten-1-one;
- Musk ingredients: 1,4-dioxa-5,17-cycloheptadecanedione, (Z)-4-cyclopentadecen-1-one, 3-methylcyclopentadecanone, 1-oxa-12-cyclohexadecen-2-one, 1-oxa-13-cyclohexadecen-2-one, (9Z)-9-cycloheptadecen-1-one, 2-{1S)-1-[(1R)-3,3-dimethylcyclohexyl]ethoxy}-2-oxoethyl propionate 3-methyl-5-cyclopentadecen-1-one, 1,3,4,6,7,8-hexahydro-4,6,6,7,8,8-hexamethyl-cyclopenta-g-2-benzopyrane, (1S,1'R)-2-[1-(3',3'-dimethyl-1'-cyclohexyl)ethoxy]-2-methylpropyl propanoate, oxacyclohexadecan-2-one and/or (1S,1'R)-[1-(3',3'-dimethyl-1'-cyclohexyl)ethoxycarbonyl]methyl propanoate;
- Woody ingredients: 1-[(1RS,6SR)-2,2,6-trimethylcyclohexyl]-3-hexanol, 3,3-dimethyl-5-[(1R)-2,2,3-trimethyl-3-cyclopenten-1-yl]-4-penten-2-ol, 3,4'-dimethylspiro[oxirane-2,9'-tricyclo[6.2.1.0$^{2,7}$]undec[4]ene, (1-ethoxyethoxy)cyclododecane, 2,2,9,11-tetramethylspiro[5.5]undec-8-en-1-yl acetate, 1-(octahydro-2,3,8,8-tetramethyl-2-naphtalenyl)-1-ethanone, patchouli oil, terpenes fractions of patchouli oil, Clearwood®, (1'R,E)-2-ethyl-4-(2',2',3'-trimethyl-3'-cyclopenten-1'-yl)-2-buten-1-ol, 2-ethyl-4-(2,2,3-trimethyl-3-cyclopenten-1-yl)-2-buten-1-ol, methyl cedryl ketone, 5-(2,2,3-trimethyl-3-cyclopentenyl)-3-methylpentan-2-ol, 1-(2,3,8,8-tetramethyl-1,2,3,4,6,7,8,8a-octahydronaphthalen-2-yl)ethan-1-one and/or isobornyl acetate;
- Other ingredients (e.g. amber, powdery spicy or watery): dodecahydro-3a,6,6,9a-tetramethyl-naphtho[2,1-b]furan and any of its stereoisomers, heliotropin, anisic aldehyde, eugenol, cinnamic aldehyde, clove oil, 3-(1,3-benzodioxol-5-yl)-2-methylpropanal, 7-methyl-2H-1,5-benzodioxepin-3(4H)-one, 2,5,5-trimethyl-1,2,3,4,4a,5,6,7-octahydro-2-naphthalenol, 1-phenylvinyl acetate, 6-methyl-7-oxa-1-thia-4-azaspiro[4.4]nonan and/or 3-(3-isopropyl-1-phenyl)butanal.

A composition according to the invention may not be limited to the above mentioned perfuming co-ingredients, and many other of these co-ingredients are in any case listed in reference texts such as the book by S. Arctander, Perfume and Flavor Chemicals, 1969, Montclair, New Jersey, USA, or its more recent versions, or in other works of a similar nature, as well as in the abundant patent literature in the field of perfumery.

In a particular embodiment, the perfuming composition according to the invention comprises a perfumery adjuvant.

The term "perfumery adjuvant" is understood as an ingredient capable of imparting additional added benefit such as a color, a particular light resistance, chemical stability and etc. A detailed description of the nature and type of adjuvant commonly used in perfuming bases cannot be exhaustive, but it has to be mentioned that the ingredients are well known to a person skilled in the art. However, one may cite as specific non-limiting examples the following: viscosity agents (e.g. surfactants, thickeners, gelling and/or rheology modifiers), stabilizing agents (e.g. preservatives, antioxidants, heat/light and or buffers or chelating agents, such as BHT), coloring agents (e.g. dyes and/or pigments), preservatives (e.g. antibacterial or antimicrobial or antifungal or anti-irritant agents), abrasives, skin cooling agents, fixatives, insect repellants, ointments, vitamins and mixture thereof.

It is understood that a person skilled in the art is perfectly able to design optimal formulations for the desired effect by admixing the above-mentioned components of a perfuming composition, simply by applying the standard knowledge of the art as well as by trial and error methodologies.

Another aspect of the invention concerns a perfumed consumer product comprising the perfuming composition according to the invention.

For the sake of clarity, it has to be mentioned that, the term “perfumed consumer product” is understood as a consumer product, which is expected to deliver at least a pleasant perfuming effect to the surface to which it is applied (e.g. skin, hair, textile, or hard surface). In other words, a perfumed consumer product according to the invention is a perfumed consumer product, which comprises the inventive perfuming composition, as well as optionally additional benefit agents, corresponding to the desired consumer product, e.g. a conditioner, a detergent or an air freshener, and an olfactorily effective amount of the perfuming composition according to the invention. For the sake of clarity, the perfuming consumer product is a non-edible product.

The nature and type of the constituents of the perfuming consumer product do not warrant a more detailed description here, which in any case would not be exhaustive, the skilled person being able to select them on the basis of his general knowledge and according to the nature and the desired effect of the product.

Non-limiting examples of suitable perfumed consumer products include a perfume, such as a fine perfume, a splash or eau de parfum, a cologne or a shave or after-shave lotion; a fabric care product, such as a liquid or solid detergent, a fabric softener, a liquid or solid scent booster, a fabric refresher, an ironing water, a paper, a bleach, a carpet cleaner, a curtain-care product; a body-care product, such as a hair care product (e.g. a shampoo, a coloring preparation or a hair spray, a color-care product, a hair shaping product, a dental care product), a disinfectant, an intimate care product; a cosmetic preparation (e.g. a skin cream or lotion, a vanishing cream or a deodorant or antiperspirant (e.g. a spray or roll on), a hair remover, a tanning or sun or after sun product, a nail product, a skin cleansing, a makeup); or a skin-care product (e.g. a soap, a shower or bath mousse, oil or gel, or a hygiene product or a foot/hand care products); an air care product, such as an air freshener or a “ready to use” powdered air freshener which can be used in the home space (rooms, refrigerators, cupboards, shoes or car) and/or in a public space (halls, hotels, malls, etc.); or a home care product, such as a mold remover, a furniture care product, a wipe, a dish detergent or a hard-surface (e.g. a floor, bath, sanitary or a window-cleaning) detergent; a leather care product; a car care product, such as a polish, a wax or a plastic cleaner.

Typical examples of fabric detergents or softener compositions into which the compounds of the invention can be incorporated are described in WO 97/34986 or in U.S. Pat. Nos. 4,137,180 and 5,236,615 or EP 799 885. Other typical detergent and softening compositions which can be used are described in works such as Ullmann's Encyclopedia of Industrial Chemistry, Vol. 20, Wiley-VCH, Weinheim, p. 355-540 (2012); Flick, Advanced Cleaning Product Formulations, Noye Publication, Park Ridge, New Jersey (1989); Showell, in Surfactant Science Series, vol. 71: Powdered Detergents, Marcel Dekker, New York (1988); Proceedings of the World Conference on Detergents (4th, 1998, Montreux, Switzerland), AOCS print.

The proportions in which the perfuming composition according to the invention can be incorporated into the various aforementioned articles or compositions vary within a wide range of values. These values are dependent upon the nature of the article or product to be perfumed and on the desired olfactory effect as well as the nature of the co-ingredients in a given composition when the compounds according to the invention are mixed with perfuming co-ingredients, solvents or additives commonly used in the art.

In the case of perfumed consumer product, typical concentrations are in the order of 0.001% to 10% by weight, or even more, preferably 0.01% to 5% by weight of the perfuming composition of the invention based on the weight of the consumer product into which the perfuming composition is incorporated.

In a particular embodiment, the perfumed consumer product is a perfume, a fabric care product, a body-care product, a cosmetic preparation, a skin-care product, an air care product or a home care product.

In a particular embodiment, the perfumed consumer product is a fine perfume, a splash or eau de perfume, a cologne, a shave or after-shave lotion, a liquid or solid detergent, a fabric softener, a fabric refresher, an ironing water, a paper, a bleach, a carpet cleaners, curtain-care products, a shampoo, a coloring preparation, a color care product, a hair shaping product, a dental care product, a disinfectant, an intimate care product, a hair spray, a hair conditioning product, a vanishing cream, a deodorant or antiperspirant, hair remover, tanning or sun product, nail products, skin cleansing, a makeup, a perfumed soap, shower or bath mousse, oil or gel, or a foot/hand care products, a hygiene product, an air freshener, a “ready to use” powdered air freshener, a mold remover, furnisher care, wipe, a dish detergent or hard-surface detergent, a leather care product, a car care product.

Another aspect of the invention concerns the use of a perfuming composition according to the invention for improving, enhancing, conferring and/or modifying the fragrance impression and/or fragrance intensity of consumer product.

Another aspect of the invention concerns a method for improving, enhancing, conferring and/or modifying the fragrance impression and/or fragrance intensity of a consumer product, comprising the step of adding the perfuming composition according to the invention to a consumer product.

In view of the above, by the combination of two or more pro-perfumes, the inventive perfuming composition shows an improved release profile of highly volatile perfumery raw materials (PRMs), and thus a more prolonged release of volatile perfumery raw materials (PRMs).

EXAMPLES

The invention is hereafter described in a more detailed manner by way of the following examples, wherein the abbreviations have the usual meaning in the art; temperatures are indicated in degrees centigrade (° C.), bp=boiling point. NMR spectral data were recorded on a Bruker AMX 500 spectrometer in $CDCl_3$ at 500 MHz for $^1H$ and at 125.8 MHz for $^{13}C$ if not indicated otherwise, the chemical displacements 6 are indicated in ppm with respect to $Si(CH_3)_4$ as the standard, the coupling constants J are expressed in Hz (br.=broad peak). Reactions were carried out in standard glassware under $N_2$. Commercially available reagents and solvents were used without further purification if not stated otherwise.

Although specific conformations or configurations are indicated for some of the compounds, this is not meant to limit the use of these compounds to the isomers described. According to the invention, all possible conformation or configuration isomers are expected to have a similar effect.

Example 1

Synthesis of Pro-Perfumes According to Formula (I) and According to Formulae (III) to (XV)

(a) Synthesis of (±)-3-(dodecylthio)-1-((1SR,2RS)-2,6,6-trimethylcyclohex-3-en-1-yl)butan-1-one [Compound 1, HaloScent® D, Pro-Perfume According to Formula (I)]

1,8-Diazabicyclo[5.4.0]undec-7-ene (DBU, 0.75 g, 4.5 mmol) was slowly added to a solution of (E)-1-((1SR,2RS)-2,6,6-trimethylcyclohex-3-en-1-yl)but-2-en-1-one (trans-delta-damascone, 1.14 g, 5.9 mmol) and dodecane-1-thiol (1.00 g, 4.9 mmol) in tetrahydrofuran (THF, 6 mL). After stirring at room temperature for 1 d, n-heptane (15 mL) was added and the mixture treated with an aqueous solution of HCl (10%, 10 mL) and washed with a saturated aqueous solution of NaCl (2×10 mL). The organic layer was dried ($Na_2SO_4$), filtered and concentrated. Bulb-to-bulb distillation (100° C., 0.05 mbar, 4 h) to remove remaining volatiles afforded 1.95 g (90%) of the title compound as a mixture of two diastereoisomers in a ratio of ca. 1.8:1. This pro-perfume compound releases trans-delta-damascone upon exposure to moisture and/or to air/oxygen.

$^1$H-NMR: 5.58-5.49 (m, 1H), 5.49-5.42 (m, 1H), 3.35-3.25 (m, 1H), 2.94-2.87 (m, 0.5H), 2.76-2.65 (m, 1H), 2.57-2.46 (m, 3.5H), 2.22 and 2.21 (d, J=10.6, 1H), 2.01-1.92 (m, 1H), 1.73-1.66 (m, 1H), 1.65-1.52 (m, 2H), 1.41-1.31 (m, 2H), 1.31-1.23 (m, 19H), 0.99, 0.97, 0.96 and 0.95 (s, 6H), 0.93-0.84 (m, 6H).

$^{13}$C-NMR (major isomer): 212.41, 131.85, 124.10, 62.84, 55.25, 41.74, 34.13, 33.18, 31.92, 31.56, 30.87, 29.79, 29.74, 29.66, 29.64, 29.61, 29.53, 29.36, 29.25, 29.04, 22.70, 21.58, 20.73, 19.94, 14.13.

$^{13}$C-NMR (minor isomer): 212.54, 131.80, 124.24, 62.96, 55.34, 41.76, 34.10, 33.04, 31.92, 31.80, 30.95, 29.79, 29.73, 29.66, 29.64, 29.61, 29.53, 29.36, 29.25, 29.04, 22.70, 21.76, 20.73, 19.88, 14.13.

(b) Synthesis of (±)-4-(dodecylthio)-4-(2,6,6-trimethylcyclohex-1-en-1-yl)butan-2-one [Compound 2a, HaloScent® I, Pro-Perfume According to Formula (I)]

DBU (0.75 g, 4.5 mmol) was slowly added to a solution of (E)-4-(2,6,6-trimethylcyclohex-1-en-1-yl)but-3-en-2-one (beta-ionone, 1.14 g, 5.9 mmol) and dodecane-1-thiol (1.00 g, 4.9 mmol) in tetrahydrofuran (THF, 6 mL). The reaction mixture was stirred at room temperature for 1 d. Column chromatography ($SiO_2$, n-heptane/ethyl acetate 97:3) afforded 1.57 g (80%) of the title compound. This pro-perfume compound releases beta-ionone upon exposure to moisture and/or to air/oxygen.

$^1$H-NMR: 3.98 (dd, J=8.4, 3.2, 1H), 3.28 (dd, J=18.0, 8.4, 1H), 2.87 (dd, J=18.0, 3.2, 1H), 2.63-2.49 (m, 2H), 2.17 (s, 3H), 2.01-1.83 (m, 2H), 1.80 (s, 3H), 1.62-1.18 (m, 24H), 1.15 (s, 3H), 0.94 (s, 3H), 0.88 (t, J=7.0, 3H).

$^{13}$C-NMR: 206.72, 140.02, 131.45, 53.11, 39.75, 38.25, 35.82, 34.09, 33.71, 31.93, 30.79, 29.67, 29.64, 29.61, 29.54, 29.48, 29.36, 29.27, 29.03, 28.32, 27.86, 22.70, 22.37, 19.27, 14.13.

Similarly, (±)-4-(dodecylthio)-4-(2,6,6-trimethylcyclohex-2-en-1-yl)butan-2-one [Compound 2b, HaloScent® 1] was obtained from (E)-4-(2,6,6-trimethylcyclohex-2-en-1-yl)but-3-en-2-one (alpha-ionone) after stirring for 5 h. Column chromatography ($SiO_2$, n-heptane/ethyl acetate 98:2) afforded 1.08 g (55%) of the title compound.

This pro-perfume compound releases alpha-ionone upon exposure to moisture and/or to air/oxygen.

$^1$H-NMR: 5.48-5.41 (m, 1H), 3.64-3.57 (m, 1H), 2.72-2.49 (m, 4H), 2.15 (s, 3H), 2.03-1.92 (m, 3H), 1.81 (s, 3H), 1.62-1.53 (m, 2H), 1.40-1.20 (m, 19H), 1.19-1.11 (m, 1H), 1.02 (s, 3H), 0.91 (s, 3H), 0.88 (t, J=6.7, 3H).

$^{13}$C-NMR: 207.17, 134.06, 123.08, 55.35, 48.68, 38.38, 33.45, 33.28, 31.93, 31.57, 30.98, 29.67, 29.65, 29.61, 29.55, 29.49, 29.36, 29.25, 29.00, 28.55, 27.64, 25.34, 22.94, 22.70, 14.13.

Pro-perfume compounds 2a and 2b can either be used individually or as a mixture of both compounds, preferably in a weight ratio from 40:60 to 60:40.

(c) Synthesis of (±)-2-(dodecylthio)octan-4-one [Compound 3, Pro-Perfume According to Formula (I)]

(E)-2-Octen-4-one (16.6 g, 100 mmol) and dodecane-1-thiol (20.2 g, 7.8 mmol) were stirred at room temperature for 2 weeks. Bulb-to-bulb distillation (to remove remaining volatiles) afforded 28.4 g of the crude compound. Column chromatography ($SiO_2$, n-heptane then n-heptane/ethyl acetate 98:2 and 95:5) gave 12.0 g (37%) of the title compound. This pro-perfume compound releases 2-octen-4-one upon exposure to moisture and/or to air/oxygen.

$^1$H-NMR: 3.29-3.20 (m, 1H), 2.70 (dd, J=16.6, 5.9 Hz, 1H), 2.52 (dd, J=16.3, 8.0 Hz, 1H), 2.52 (t, J=7.5 Hz, 2H), 2.47-2.35 (m, 2H), 1.61-1.52 (m, 4H), 1.42-1.20 (m, 23H), 0.91 (t, J=7.4 Hz, 3H), 0.88 (t, J=7.1 Hz, 3H).

$^{13}$C-NMR: 209.15, 50.15, 43.40, 35.11, 31.94, 30.89, 29.75, 29.67, 29.65, 29.62, 29.55, 29.37, 29.26, 29.03, 25.78, 22.71, 22.33, 21.74, 14.13, 13.86.

(d) Synthesis of 4-(dodecylthio)-4-methylpentan-2-one [Compound 4, Pro-Perfume According to Formula (I)]

DBU (0.74 g, 4.5 mmol) was slowly added to a solution of 4-methyl-3-penten-2-one (mesityl oxide, 5.70 g, 58.1 mmol) and dodecane-1-thiol (9.80 g, 48.4 mmol) in tetrahydrofuran (THF, 50 mL). After stirring at room temperature for 3 d, n-heptane (50 mL) was added and the mixture treated with an aqueous solution of HCl (10%, 50 mL) and washed with a saturated aqueous solution of NaCl (2×50 mL). The organic layer was dried ($Na_2SO_4$), filtered and concentrated. Bulb-to-bulb distillation (90° C., 0.05 mbar, 2 h) to remove remaining volatiles afforded 12.80 g (88%) of the title compound. This pro-perfume compound releases mesityl oxide upon exposure to moisture and/or to air/oxygen.

$^1$H-NMR: 2.69 (s, 2H), 2.53 (t, J=7.5, 2H), 2.19 (s, 3H), 1.60-1.51 (m, 2H), 1.46-1.34 (m, 2H), 1.42 (s, 6H), 1.34-1.20 (m, 16H), 0.88 (t, J=6.9, 3H).

$^{13}$C-NMR: 206.98, 54.72, 43.31, 32.37, 31.93, 29.66, 29.64, 29.60, 29.54, 29.36, 29.29 (2×), 28.52, 28.16, 22.70, 14.13.

(e) Synthesis of (±)-ethyl N,S-bis(4-oxo-4-(2,6,6-trimethylcyclohex-3-en-1-yl)butan-2-yl)-L-cysteinate [Compound 5, Pro-Perfume According to Formula (I)]

A solution of ethyl L-cysteine hydrochloride (4.8 g, 26 mmol), N-ethyl-N-isopropylpropan-2-amine (26 mmol, 3.36 g) and trans-delta-damascone (10.0 g, 52 mmol) in ethanol (70 mL) was heated under reflux for 6 days. After cooling to room temperature, the solvent was removed under reduced pressure and the residue taken up in ethyl acetate (70 mL) and washed with a saturated aqueous solution of NaCl (2×50 mL). The organic phase was dried ($Na_2SO_4$), filtered and concentrated to give the crude compound. Column chromatography ($SiO_2$, n-heptane/ethyl acetate 7:3) afforded 6.5 g (47%) of the title compound as a complex mixture of diastereoisomers. This pro-perfume compound releases trans-delta-damascone upon exposure to moisture and/or to air/oxygen.

HR-LCMS (Q-Exactive): calculated for $C_{31}H_{52}NO_4S^+$ $[M+H]^+$ 534.36116, found 534.36102.

Depending on the stoichiometry of the reagents and on the reaction conditions, ethyl S-(4-oxo-4-(2,6,6-trimethylcyclohex-3-en-1-yl)butan-2-yl)-L-cysteinate, which is also a pro-perfume according to formula (I), is also be formed. Both pro-perfume compounds can be used as pure compounds or as a compound mixture.

(f) Synthesis of (±)-4-oxooctan-2-yl dodecanoate [Compound 6, Pro-Perfume According to Formula (I)]

Dodecanoyl chloride (33.4 g, 153 mmol) was added dropwise to a stirred solution of (±)-2-hydroxyoctan-4-one (20.0 g, 139 mmol), 4-dimethylaminopyridine (DMAP, 22.4 g, 183 mmol) triethylamine (18.2 g, 180 mmol) in dichloromethane (200 mL). After stirring at room temperature for 22 h, the reaction mixture was poured onto an aqueous solution of HCl (10%, 250 mL) and ice (200 g) and extracted with ethyl acetate (350 mL). The organic phase was washed with a saturated aqueous solution of NaCl (250 mL), a saturated aqueous solution of $NaHCO_3$ (250 mL) and again with a saturated aqueous solution of NaCl (2×250 mL). The aqueous phases were each re-extracted with ethyl acetate (200 mL). The combined organic phases were dried ($Na_2SO_4$), filtered and concentrated. Column chromatography in two batches ($SiO_2$, n-heptane/ethyl acetate 95:5, then 90:10) and drying under high vacuum (0.09 mbar) for 4 h afforded a total of 36.72 g (78%) of the title compound. This pro-perfume compound releases 2-octen-4-one upon exposure to moisture.

$^1$H-NMR: 5.33-5.24 (m, 1H), 2.77 (dd, J=16.0, 7.4 Hz, 1H), 2.52 (dd, J=16.0, 5.8 Hz, 1H), 2.41 (t, J=7.4 Hz, 2H), 2.24 (t, J=7.5 Hz, 2H), 1.63-1.50 (m, 4H), 1.37-1.19 (m, 21H), 0.90 (t, J=7.4 Hz, 3H), 0.88 (t, J=6.9 Hz, 3H).

$^{13}$C-NMR: 207.88, 173.07, 66.94, 48.59, 43.10, 34.55, 31.92, 29.62, 29.47, 29.35, 29.28, 29.12, 25.68, 24.98, 22.70, 22.29, 20.11, 14.12, 13.85.

(q) Synthesis of (±)-2-(dodecylsulfonyl)octan-4-one [Compound 7, Pro-Perfume According to Formula (I)]

Under mechanical stirring, a solution of oxone (2 $KHSO_5$/$KHSO_4$/$K_2SO_4$, 83.3 g, 547 mmol) in water (400 mL) was added dropwise to a solution of (±)-2-(dodecylthio)octan-4-one (Compound 3) in methanol (850 mL), which was cooled to 1° C. After the introduction, the cooling was stopped, and the suspension continued stirring for 18 h. The reaction mixture was extracted with ethyl acetate (800 mL), washed with a saturated aqueous solution of NaCl (500 mL), demineralized water (500 mL), a saturated aqueous solution of $NaHCO_3$ (500 mL) and a saturated aqueous solution of NaCl (500 mL). The aqueous phases were each re-extracted with ethyl acetate (500 mL). The combined organic phases were dried ($Na_2SO_4$), filtered and concentrated. Drying under high vacuum for 15 h afforded 40.0 g (99%) of the title compound. This pro-perfume compound releases 2-octen-4-one upon exposure to moisture and/or to air/oxygen.

$^1$H-NMR: 3.69-3.57 (m, 1H), 3.18 (dd, J=18.1, 3.9 Hz, 1H), 2.93 (t, J=8.2 Hz, 2H), 2.60 (dd, J=18.3, 8.7 Hz, 1H), 2.54-2.40 (m, 2H), 1.95-1.75 (m, 2H), 1.63-1.54 (m, 2H), 1.50-1.39 (m, 2H), 1.39-1.19 (m, 18H), 1.36 (d, J=6.8 Hz, 3H), 0.91 (t, J=7.4 Hz, 3H), 0.88 (t, J=7.1 Hz, 3H).

$^{13}$C-NMR: 206.86, 52.42, 50.40, 43.10, 41.00, 31.91, 29.60, 29.59, 29.50, 29.33, 29.27, 29.07, 28.59, 25.81, 22.69, 22.26, 21.52, 14.49, 14.12, 13.80.

(h) Synthesis of a Linear Polysiloxane Co-Polymer of (3-Mercaptopropyl)(Methyl)Dimethoxysilane [Compound 8, Pro-Perfume According to Formula (III)]

In a 50 mL round-bottomed flask, (3-mercaptopropyl)(methyl)dimethoxysilane (25 mmol), dimethyl)diethoxysilane (5 mmol), and (trimethyl)ethoxysilane (15 mmol) were dissolved altogether in water (75 mmol) and sodium hydroxide (1.3 wt % with respect to the amount of water) to give an emulsion. The reaction mixture was stirred at room temperature for 3 h. Ethanol, methanol and possible residual water were removed by evaporation under reduced pressure. 2-methyl-5-(prop-1-en-2-yl)cyclohex-2-en-1-one (25 mmol) and DBU (1.25 mmol) were added and the reaction mixture was stirred at room temperature for 3 h to give a viscous oil. This oil was diluted in ethyl acetate (10 mL) and washed with aq. NaCl (5 M, 2×10 mL). The aqueous layer was re-extracted with ethyl acetate (1×10 mL). The organic layers were combined and dried with $MgSO_4$, filtered and dried under vacuum at 50° C. overnight to give a co-polymer with a molecular weight of 2100 Da. This pro-perfume compound releases carvone upon exposure to moisture and/or to air/oxygen.

$^1$H-NMR (400 MHz): 4.78 (m, 1.9H), 2.89 (m, 0.7H), 2.57 (m, 4H), 2.32 (m, 2H), 2.20 (m, 0.7H), 1.99 (m, 0.5H), 1.82 (m, 1H), 1.75 (m, 3H), 1.62 (m, 2H), 1.23 (m, 3H), 0.63 (m, 2H), 0.09 (m, 6H).

$^{13}$C-NMR (100 MHz): 209.8, 147.1, 146.7, 146.4, 144.6, 111.1, 110.5, 110.3, 110.2, 50.2, 50.1, 48.8, 46.4, 46.0, 44.4, 43.3, 43.2, 41.7, 40.7, 40.2, 39.6, 36.0, 35.6, 34.3, 34.2, 34.0, 32.8, 32.0, 31.2, 27.9, 23.8, 23.6, 23.4, 21.5, 21.1, 20.9, 20.5, 20.3, 17.3, 16.5, 15.7, 14.2, 12.6, 1.9, 1.3, −0.3, −1.0.

(i) Synthesis of (2-((2-methylundec-1-en-1-yl)oxy)ethyl)benzene [Compound 9, Pro-Perfume According to Formula (IV)]

A mixture of the dimethyl acetal of 2-methylundecanal (8.0 g, 34.7 mmol), 2-phenylethanol (8.5 g, 69.4 mmol), and $KHSO_4$ (48 mg, 0.35 mmol) was heated with a 150° C. oil bath for 1 h while allowing liberated methanol to distill from the reaction flask. The mixture was placed under vacuum (40 Pa) and heated with a 190° C. oil bath for 2 h while allowing liberated 2-phenylethanol to distill from the reaction flask. The reaction mixture was allowed to cool and $Na_2CO_3$ (0.5 g) was added. The title compound (9.1 g, 91%) then was isolated by distillation from the reaction flask (bp 130° C., 4 Pa) as a mixture of isomers (E/Z ca. 59:41). This pro-perfume compound releases 2-undecanone, 2-phenylethyl formate and 2-phenylethanol upon exposure to air/oxygen and to moisture.

$^1$H-NMR (E-isomer): 7.30-7.17 (m, 5H), 5.81 (s, 1H), 3.86 (t, J=7.3, 2H), 2.91 (t, J=7.3, 2H), 1.85 (t, J=7.5, 2H), 1.57 (s, 3H), 1.39-1.19 (m, 14H), 0.88 (t, J=7.0, 3H).

$^{13}$C-NMR (isomer mixture): 140.07, 139.91, 138.60, 138.52, 129.00, 128.36, 128.33, 126.27, 126.24, 115.21, 114.90, 72.45, 72.41, 36.39, 36.36, 33.94, 31.96, 31.93, 29.67, 29.63, 29.61, 29.55, 29.50, 29.40, 29.37, 29.22, 28.96, 28.04, 27.42, 22.71, 22.70, 17.25, 14.14, 14.13, 12.94.

(j) Synthesis of 1-methoxy-4-(3-methyl-4-phenethoxybut-3-en-1-yl)benzene [Compound 10, Pro-Perfume According to Formula (IV)]

Methoxymethyltriphenylphosphonium chloride (17.7 g, 51.7 mmol) and 4-(4-methoxyphenyl)butan-2-one (6.12 g, 34.3 mmol) were added to toluene (150 mL). Potassium tert-butoxide (6.18 g, 55.1 mmol) was added to the stirring slurry in 4 portions every 15 min. The mixture was stirred for another 4 h. It then was poured into water (200 mL) and extracted with diethyl ether (3×100 mL). The organic phases were combined, dried over $MgSO_4$, filtered and concentrated. The residue was subjected to flash chromatography ($SiO_2$, hexane/$CH_2Cl_2$ 100:0 to 75:25) affording 4.06 g of the methyl enol ether product. This material (3.8 g, 18.4 mmol) was combined with 2-phenylethanol (4.5 g, 36.8 mmol) and $KHSO_4$ (0.027 g, 0.198 mmol) and heated for 1 h at 150° C. Liberated methanol was distilled from the mixture, which was then placed under vacuum (40 Pa) and heated at 190° C. for 2 h while allowing the excess 2-phenylethanol to distill from the flask. $Na_2CO_3$ (0.3 g) was added to the flask and the title compound (4.46 g, 82%) was isolated by distillation (bp 170° C., 4 Pa) as a mixture of isomers (E/Z ca. 57:43). This pro-perfume compound releases 4-(4-methoxyphenyl)butan-2-one, 2-phenylethyl formate and 2-phenylethanol upon exposure to air/oxygen and to moisture.

$^1$H-NMR (600 MHz, E-isomer): 7.31-7.17 (m, 5H), 7.07 (d, J=8.6, 2H), 6.80 (d, J=8.6, 2H), 5.77 (q, J=1.2, 1H), 3.84 (t, J=7.2, 2H), 3.76 (s, 3H), 2.86 (t, J=7.2, 2H), 2.61 (m, 2H), 2.13 (br. t, J=7.9, 2H), 1.63 (d, J=1.2, 3H).

$^{13}$C-NMR (151.0 MHz, isomer mixture): 157.69, 157.61, 140.80, 140.46, 138.59, 138.45, 134.68, 134.39, 129.29, 128.99, 128.35, 126.27, 126.26, 114.20, 113.87, 113.65, 113.53, 72.48, 72.35, 55.23, 36.36, 36.33, 36.32, 33.91, 32.83, 31.15, 17.35, 13.09.

(k) Synthesis of (3-methyl-4-phenethoxybut-3-en-1-yl)benzene [Compound 11, Pro-Perfume According to Formula (IV)]

Using the dimethyl acetal of 2-methyl-4-phenylbutanal and 2-phenylethanol, the title compound was prepared following the procedure described for Compound 9. It was isolated by distillation (bp 130° C., 4 Pa) as a mixture of isomers in 83% yield (E/Z ca. 52:48). This pro-perfume compound releases 4-phenylbutan-2-one, 2-phenylethyl formate and 2-phenylethanol upon exposure to air/oxygen and to moisture.

$^1$H-NMR (600 MHz, E-isomer): 7.30-7.11 (m, 10H), 5.76 (q, J=1.2, 1H), 3.81 (t, J=7.2, 2H), 2.83 (t, J=7.2, 2H), 2.66 (t, J=7.9, 2H), 2.16 (t, J=7.9, 2H), 1.64 (d, J=1.2, 3H).

$^{13}$C-NMR (151.0 MHz, isomer mixture): 142.52, 142.23, 140.83, 140.52, 138.54, 138.41, 128.96, 128.43, 128.40, 128.32, 128.21, 128.08, 126.25, 126.24, 125.68, 125.55, 113.97, 113.67, 72.44, 72.31, 36.30, 36.29, 36.12, 34.84, 33.76, 30.97, 17.34, 13.07.

(l) Synthesis of 1-(((Z)-hex-3-en-1-yl)oxy)-2-methylundec-1-ene [Compound 12, Pro-Perfume According to Formula (IV)]

A mixture of the dimethyl acetal of 2-methylundecanal (20 g, 87 mmol), cis-3-hexen-1-ol (26.1 g, 260 mmol), and $KHSO_4$ (0.118 g, 0.87 mmol) was heated at 150° C. for 1 h while distilling out liberated methanol. The heating was continued at 190° C. for 1 h while allowing liberated cis-3-hexen-1-ol to distill from the reaction flask. The mixture was allowed to cool, placed under vacuum (667 Pa) and heated at 130° C. for 3 h to remove remaining 3-hexen-1-ol. The enol ether then was isolated by vacuum distillation from the reaction flask (bp 120-130° C., 3.3 Pa) followed by a bulb-to-bulb distillation (115° C., 3.3 Pa) to afford the title compound (17.0 g, 73%) as a mixture of isomers (E/Z ca. 56:44). This pro-perfume compound releases 2-undecanone, (Z)-hex-3-en-1-yl formate and (Z)-hex-3-en-1-ol upon exposure to air/oxygen and to moisture.

$^1$H-NMR (600 MHz, E-isomer): 5.81 (s, 1H), 5.51-5.44 (m, 1H), 5.37-5.30 (m, 1H), 3.65 (t, J=7.0, 2H), 2.38-2.31 (m, 2H), 2.09-2.03 (m, 2H), 1.85 (t, J=7.5, 2H), 1.58 (s, 3H), 1.40-1.20 (m, 14H), 0.96 (t, J=7.5, 3H), 0.88 (t, J=7.0, 3H).

$^{13}$C-NMR (151.0 MHz, isomer mixture): 140.23, 140.09, 133.98, 133.89, 124.40, 124.35, 114.87, 114.58, 71.27, 71.25, 33.98, 31.97, 31.95, 29.69, 29.66, 29.62, 29.58, 29.49, 29.42, 29.39, 29.24, 28.90, 28.07, 27.97, 27.96, 27.42, 22.73, 22.72, 20.64, 17.27, 14.28, 14.13, 12.88.

(m) Synthesis of (2-((2-methylundec-1-en-1-yl)oxy)ethoxy)benzene [Compound 13, Pro-Perfume According to Formula (IV)]

Using the dimethyl acetal of 2-methylundecanal and 2-phenoxyethanol, the title compound was prepared following the procedure described for Compound 9. It was isolated by distillation (bp 128-130° C., 3.3 Pa) as a mixture of isomers (E/Z ca. 60:40) in 90% yield. This pro-perfume compound releases 2-undecanone, 2-phenoxyethyl formate and 2-phenoxyethan-1-ol upon exposure to air/oxygen and to moisture.

$^1$H-NMR (600 MHz, E-isomer): 7.30-7.24 (m, 2H), 6.96-6.89 (m, 3H), 5.89 (s, 1H), 4.12 (t, J=5.0, 2H), 4.00 (t, J=5.0, 2H), 1.85 (t, J=7.4, 2H), 1.58 (s, 3H), 1.39-1.19 (m, 14H), 0.88 (t, J=7.0, 3H).

$^{13}$C-NMR (151.0 MHz, isomer mixture): 158.76, 158.75, 140.16, 139.96, 129.42, 129.41, 120.92, 120.90, 116.04, 115.65, 114.68, 114.66, 69.95, 69.93, 67.01, 66.91, 33.90, 31.95, 31.94, 29.66, 29.64, 29.61, 29.57, 29.47, 29.41, 29.39, 29.23, 28.86, 27.98, 27.36, 22.71, 17.20, 14.14, 12.91.

(n) Synthesis of 2-methyl-1-(octan-3-yloxy)undec-1-ene [Compound 14, Pro-Perfume According to Formula (IV)]

A solution of 2-methylundecanal (4.34 g, 23.5 mmol), 3-octanol (7.42 g, 57 mmol) and para-toluenesulphonic acid monohydrate (0.09 g, 0.46 mmol) in toluene (100 mL) was heated at reflux for 3 h. The water of reaction was removed with a Dean-Stark trap. The reaction mixture was diluted with ethyl acetate and then washed with a saturated aqueous solution of $NaHCO_3$ and water. The organic phase was dried ($Na_2SO_4$), filtered and concentrated. The residue was subjected to bulb-to-bulb distillation (160-170° C., 6.7 Pa) affording the title compound (3.24 g, 46%) as a mixture of isomers (E/Z ca. 61:39). This pro-perfume compound releases 2-undecanone, octan-3-yl formate and octan-3-ol upon exposure to air/oxygen and to moisture.

$^1$H-NMR (E-isomer): 5.81 (s, 1H), 3.42 (quint, J=5.7, 1H), 1.85 (t, J=7.4, 2H), 1.58 (s, 3H), 1.56-1.20 (m, 24H), 0.90 (t, J=7.3, 3H), 0.89 (t, J=7.1, 3H), 0.88 (t, J=7.1, 3H).

$^{13}$C-NMR (isomer mixture): 139.97, 139.90, 113.68, 113.44, 82.45, 82.44, 34.08, 33.89, 32.07, 32.06, 32.03, 32.00, 29.73, 29.70, 29.62, 29.55, 29.47, 29.43, 29.22, 28.96, 28.11, 27.47, 27.14, 27.12, 25.08, 25.07, 22.76, 22.71, 22.69, 17.37, 14.14, 14.07, 12.95, 9.57.

(o) Synthesis of 1-methoxy-4-(1-phenethoxyprop-1-en-2-yl)benzene [Compound 15, Pro-Perfume According to Formula (IV)]

General Procedure:

Methoxymethyltriphenylphosphonium chloride (15.1 g, 44.1 mmol) and the aryl ketone (29.4 mmol) were added to toluene (120 mL). Potassium tert-butoxide (5.27 g, 47 mmol) was added to the stirring slurry in 4 portions every 15 min. The mixture was stirred for 4 h; it then was poured into water (500 mL) and extracted with ethyl acetate (3×250 mL). The organic phases were combined, dried ($Na_2SO_4$), filtered and concentrated. The resulting methyl enol ether product was isolated by flash chromatography ($SiO_2$, hexane) followed by bulb-to-bulb distillation. The methyl enol ether (30 mmol) then was combined with 2-phenylethanol (2 equivalents) and $KHSO_4$ (1 mol-%). The mixture was heated (oil bath at 150° C.) while distilling out the liberated methanol (vapor temperature 64° C.) until the vapor temperature dropped. The mixture then was placed under vacuum (40 Pa) and heated at 190° C. while allowing the excess 2-phenylethanol to distill from the flask. The resulting enol ethers were isolated by vacuum distillation from the reaction flask after adding $Na_2CO_3$ (0.4 g) or by flash chromatography ($SiO_2$) followed by bulb-to-bulb distillation.

Following this general procedure, the title compound was isolated by short-path distillation of the crude reaction mixture (bp 156-158° C., 4 Pa) as a mixture of isomers (E/Z ca. 78:23) in 84% yield from the methyl enol ether. This pro-perfume compound releases 1-(4-methoxyphenyl) ethan-1-one, 2-phenylethyl formate and 2-phenylethanol upon exposure to air/oxygen and to moisture.

$^1$H-NMR (600 MHz, E-isomer): 7.32-7.18 (m, 7H), 6.85-6.81 (m, 2H), 6.36 (q, J=1.2, 1H), 4.03 (t, J=7.1, 2H), 3.78 (s, 3H), 2.98 (t, J=7.1, 2H), 1.96 (d, J=1.2, 3H).

$^{13}$C-NMR (151.0 MHz, isomer mixture): 158.00, 157.61, 142.56, 142.03, 138.25, 133.24, 130.86, 129.05, 129.03, 128.62, 128.43, 128.42, 126.40, 126.06, 114.46, 113.75, 113.19, 110.35, 73.56, 73.11, 55.27, 55.19, 36.52, 36.42, 18.33, 12.96.

(p) Synthesis of 1-methyl-4-(1-phenethoxyprop-1-en-2-yl)benzene [Compound 16, Pro-Perfume According to Formula (IV)]

The title compound was prepared according to the general procedure described for the synthesis of Compound 15 and isolated by short-path distillation of the crude reaction mixture (bp 143-145° C., 4 Pa) as a mixture of isomers (E/Z ca. 82:18) in 73% yield from the methyl enol ether. This pro-perfume compound releases 1-(4-tolyl)ethan-1-one, 2-phenylethyl formate and 2-phenylethanol upon exposure to air/oxygen and to moisture.

$^1$H-NMR (600 MHz, E-isomer): 7.32-7.07 (m, 9H), 6.42 (q, J=1.2, 1H), 4.03 (t, J=7.1, 2H), 2.97 (t, J=7.1, 2H), 2.31 (s, 3H), 1.97 (d, J=1.2, 3H).

$^{13}$C-NMR (151.0 MHz, isomer mixture): 143.12, 142.66, 138.23, 138.21, 137.74, 135.46, 135.44, 135.33, 129.05, 129.03, 129.00, 128.51, 128.44, 128.41, 127.38, 126.41, 126.39, 124.89, 114.68, 110.71, 73.62, 73.15, 36.52, 36.43, 21.13, 20.97, 18.30, 12.79.

(q) Synthesis of 2-(1-phenethoxyprop-1-en-2-yl) naphthalene [Compound 17, Pro-Perfume According to Formula (IV)]

The title compound was prepared according to the general procedure described for the synthesis of Compound 15 and isolated by flash chromatography followed by bulb-to-bulb distillation affording a mixture of isomers (E/Z ca. 80:20) in 89% yield from the methyl enol ether. This pro-perfume compound releases 1-(naphthalen-2-yl)ethan-1-one, 2-phenylethyl formate and 2-phenylethanol upon exposure to air/oxygen and to moisture.

$^1$H-NMR (600 MHz, E-isomer): 7.78-7.74 (m, 2H), 7.72 (d, J=8.7, 1H), 7.64 (s, 1H), 7.48-7.19 (m, 8H), 6.62 (q, J=1.2, 1H), 4.10 (t, J=7.0, 2H), 3.00 (t, J=7.0, 2H), 2.09 (d, J=1.2, 3H).

$^{13}$C-NMR (151.0 MHz, isomer mixture): 138.21, 138.17, 137.90, 135.90, 133.72, 133.37, 131.99, 131.95, 129.05, 128.47, 128.46, 128.10, 127.68, 127.65, 127.47, 127.34, 126.95, 126.50, 126.45, 126.44, 126.02, 125.70, 125.59, 125.25, 125.03, 123.61, 122.92, 114.54, 110.74, 73.79, 73.36, 36.58, 36.44, 18.45, 12.64.

(r) Synthesis of 4-allyl-2-methoxy-1-((2-methoxy-2-phenylvinyl)oxy)benzene [Compound 18, Pro-Perfume According to Formula (IV)]

A mixture of 2-bromoacetophenone (11.1 g, 55.9 mmol), 4-allyl-2-methoxyphenol (11.9 g, 72.7 mmol), $K_2CO_3$ (12.1 g, 88 mmol) and acetone (100 mL) was heated at reflux for 3 h. The solution was filtered through Celite® and then concentrated. The resulting 2-(4-allyl-2-methoxyphenoxy)-1-phenylethanone (13.2 g, 84%) was isolated by bulb-to-bulb distillation (115° C., 4 Pa). This ketone (10 g, 35.4 mmol) was converted to the corresponding dimethyl acetal by mixing with trimethyl orthoformate (26.3 g, 248 mmol), methanol (70 mL) and para-toluenesulfonic acid (0.34 g, 1.8 mmol) and heating the solution at 70° C. for 8 h and then stirring at room temperature for 1 d. Solid $Na_2CO_3$ (0.5 g) was added and the mixture was concentrated under vacuum. The remaining residue was dissolved in diethyl ether and washed with water, a saturated aqueous solution of $NH_3Cl$ and water. The organic phase was dried ($Na_2SO_4$), filtered and concentrated under vacuum to afford the dimethyl acetal (10.5 g) which was used without further purification. The dimethyl acetal (5.5 g, 16.7 mmol) was combined with $KHSO_4$ (0.023 g, 0.17 mmol), placed under vacuum (1500 Pa) and then heated with an oil bath at 140° C. for 2 h. The mixture was removed from the oil bath and $Na_2CO_3$ (0.2 g) was added. The reaction mixture was dissolved in diethyl ether and washed with a saturated aqueous solution of $Na_2CO_3$ and water. The organic phase was dried ($Na_2SO_4$), filtered and concentrated under vacuum. The resulting enol ether (3.9 g, 15.1 mmol) was isolated by bulb-to-bulb distillation (195° C., 2.7 Pa) as a mixture of isomers (ca. 64:36) in 79% yield from the acetal. This pro-perfume compound releases methyl benzoate, 4-allyl-2-methoxyphenyl formate and 4-allyl-2-methoxyphenol upon exposure to air/oxygen and to moisture.

$^{1}$H-NMR (major isomer): 7.48-7.44 (m, 2H), 7.36-7.30 (m, 2H), 7.29-7.24 (m, 1H), 7.00 (d, J=8.1, 1H), 6.77 (d, J=1.9, 1H), 6.72 (dd, J=8.1, 1.9, 1H), 6.47 (s, 1H), 5.96 (ddt, J=16.9, 10.2, 6.7, 1H), 5.09 (dq, J=16.9, 1.7, 1H), 5.07 (dq, J=10.2, 1.7, 1H), 3.88 (s, 3H), 3.83 (s, 3H), 3.35 (d, J=6.7, 2H).

$^{13}$C-NMR (isomer mixture): 149.64, 149.55, 146.80, 145.72, 145.50, 143.89, 137.42, 137.37, 135.49, 135.02, 134.36, 133.37, 128.86, 128.43, 127.97, 127.92, 127.74, 127.24, 127.06, 125.13, 120.58, 116.64, 115.89, 115.84, 115.83, 112.95, 112.84, 59.46, 57.60, 56.10, 55.99, 39.88, 39.87.

(s) Synthesis of 1-(dodec-1-en-1-yloxy)dodec-1-ene [Compound 19, Pro-Perfume According to Formula (V)]

General procedure: Concentrated $H_2SO_4$ (2-4 mmol) was added to a mixture of the aldehyde (147 mmol), acetic acid (441 mmol), and pentane (75 mL) cooled in an ice-water bath. Acetic anhydride (97 mmol) was added dropwise over 10-30 min and the mixture stirred for an additional 2-4 h. $Na_2CO_3$ (4.2 mmol) was added, and the pentane and acetic acid were removed on a rotary evaporator. The resulting slurry was subjected to bulb-to-bulb distillation (200-230° C., 2.7 Pa) and the distillate, composed mostly of the ether dicarboxylate, was heated in a 250° C. oil bath for 0.5-2 h, and acetic acid was distilled from the system. The resulting pro-perfume compounds were isolated after flash chromatography ($SiO_2$, hexane/$CH_2Cl_2$ 100:0 to 97.5:2.5) followed by bulb-to-bulb distillation as mixtures of the Z,Z; E,Z and E,E isomers.

Following this general procedure, the title compound was prepared from dodecanal and obtained in 58% yield as a mixture of isomers (Z,Z/E,Z/E,E=37:47:16). The reaction mixture solidified during addition of acetic anhydride, so it was allowed to warm to room temperature during formation of the ether dicarboxylate intermediate. This pro-perfume compound releases undecanal and dodecanal upon exposure to air/oxygen.

$^{1}$H-NMR (400 MHz, isomer mixture): 6.26 and 6.21 (d, J=12.3, 1H), 6.13 and 6.09 (d, J=6.1, 1H), 5.06 and 5.04 (dt, J=12.3, 7.7, 1H), 4.52 and 4.47 (q, J=6.1, 1H), 2.16-2.05 and 1.96-1.88 (m, 4H), 1.40-1.20 (m, 32H), 0.88 (t, J=6.7, 6H).

$^{13}$C-NMR (100.6 MHz, isomer mixture): 144.23, 143.13, 142.87, 141.46, 110.08, 109.69, 108.80, 108.47, 31.95, 31.93, 30.29, 30.21, 29.70, 29.65, 29.62, 29.56, 29.52, 29.49, 29.40, 29.38, 29.36, 29.25, 29.06, 27.35, 27.33, 23.99, 23.95, 22.71, 14.1.

(t) Synthesis of 2-methyl-1-((2-methylundec-1-en-1-yl)oxy)undec-1-ene [Compound 20, Pro-Perfume According to Formula (V)]

The title compound was prepared from 2-methylundecanal according to the general procedure described for the synthesis of Compound 19 and obtained in 61% yield as a mixture of isomers. This pro-perfume compound releases 2-methylundecanal and 2-undecanone upon exposure to air/oxygen.

$^{1}$H-NMR (400 MHz, isomer mixture): 6.01, 5.98 and 5.96 (s, 2H), 2.12, 2.10 and 1.87 (t, J=7.2, 4H), 1.64, 1.63, 1.53, 1.53 (d, J=1.4, 6H), 1.45-1.19 (m, 28H), 0.88 (t, J=6.9, 6H).

$^{13}$C-NMR (100.6 MHz, isomer mixture): 138.77, 138.72, 138.56, 138.52, 115.81, 115.73, 115.51, 33.79, 31.96, 29.74, 29.69, 29.66, 29.59, 29.48, 29.40, 29.26, 29.09, 28.97, 27.96, 27.35, 27.26, 22.73, 17.14, 14.14, 13.02.

(u) Synthesis of (±)-2-(6-hydroxy-2,6-dimethylheptyl)imidazolidin-4-one [Compound 21, Pro-Perfume According to Formula (VI)]

TEA (4.5 mL, 32.1 mmol) and glycinamide hydrochloride (3.38 g, 30.0 mmol) were added to a solution of (±)-7-hydroxy-3,7-dimethyloctanal (5.17 g, 30.0 mmol) in methanol (250 mL). The mixture was heated to reflux overnight. After cooling to room temperature, the solvent was removed under reduced pressure. Then demineralized water (50 mL) was added to the residue, and the mixture extracted with ethyl acetate (2×100 mL). The combined organic phases were washed with a saturated aqueous solution of NaCl (2×50 mL), dried ($Na_2SO_4$) and concentrated. Bulb-to-bulb distillation (100° C., 0.005 mbar) to reduce remaining volatiles afforded the crude compound. Column chromatography ($SiO_2$, ethyl acetate/ethanol 4:1) and drying under high vacuum gave 0.92 g (13%) of the title compound as a mixture of diastereoisomers (ca. 1.2:1). This pro-perfume compound releases 7-hydroxy-3,7-dimethyloctanal upon exposure to moisture.

$^{1}$H-NMR: 7.64 and 7.55 (br. s, 1H), 7.73-4.64 (m, 1H), 3.49-3.35 (m, 2H), 2.03 (br. s, 2H), 1.71-1.56 (m, 2H), 1.51-1.29 (m, 6H), 1.26-1.15 (m, 1H), 1.21 and 1.21 (s, 6H), 0.96 and 0.95 (d, J=6.4 and 6.5, 3H).

$^{13}$C-NMR: 177.70 and 177.64, 70.86 and 70.84, 70.50 and 70.29, 49.20 and 49.11, 44.08 and 44.00, 43.75 and 43.67, 37.59 and 37.26, 29.49 and 29.45, 29.48 and 29.13, 29.23 and 29.16, 21.38 and 21.34, 19.97 and 19.88.

(v) Synthesis of (5S)-5-benzyl-2-nonylimidazolidin-4-one [Compound 22, Pro-Perfume According to Formula (VI)]

A mixture of decanal (0.78 g, 5.0 mmol), L-phenylalaninamide hydrochloride (1.00 g, 5.0 mmol), triethylamine (TEA, 0.51 g, 5.0 mmol) and $K_2CO_3$ (1.00 g) in ethanol (8 mL) was heated to 60° C. for 24 h. Then the solvent was removed. The residue was taken up in ether, filtered and concentrated to yield 1.67 g (quant.) of the title compound as a mixture of diastereoisomers (ca. 1.2:1). This pro-perfume compound releases decanal upon exposure to moisture.

$^{1}$H-NMR (400 MHz): 7.36-7.19 (m, 5H), 7.09 and 7.06 (s, 1H), 4.52-4.45 and 4.34-4.27 (m, 1H), 3.82-3.67 (m, 1H), 3.19-3.03 (m, 1H), 3.01-2.88 (m, 1H), 1.77 (br. s, 1H), 1.57-1.44 (m, 1H), 1.44-1.12 (m, 15H), 0.88 and 0.87 (t, J=7.0, 3H).

$^{13}$C-NMR (100.6 MHz): 177.59, 137.50 and 137.37, 129.56 and 129.51, 128.62 and 128.57, 126.79 and 126.75, 69.75 and 69.46, 60.38 and 59.45, 37.49 and 37.41, 37.22 and 36.61, 31.87, 29.47, 29.44 and 29.41, 29.39, 29.26, 24.68 and 24.24, 22.67, 14.09.

(w) Synthesis of (3S,6S,9R)-3-benzyl-6-isopropyl-9-methyl-1,4-diazaspiro[4.5]decan-2-one [Compound 23, Pro-Perfume According to Formula (VI)]

(−)-Menthone (0.69 g, 4.5 mmol) and TEA (0.46 g, 5.0 mmol) were added to a suspension of L-phenylalaninamide hydrochloride (0.90 g, 4.5 mmol) in methanol (puriss, 6 mL). The mixture was heated to reflux for 18 h. After cooling to room temperature, the solvent was removed under reduced pressure. Then demineralized water (25 mL) was added to the residue, and the mixture extracted with ethyl acetate (3×25 mL). The combined organic phases were dried ($Na_2SO_4$), concentrated and dried under high vacuum (0.3 mbar, 1 h) to give 0.74 g (55%) of the title compound as a mixture of two diastereoisomers. This pro-perfume compound can be used as such and releases (−)-menthone upon exposure to moisture. Recrystallisation (ethyl acetate/heptane 4:1), filtration and drying under high vacuum (0.3 mbar, 1 h) afforded 0.15 g of the (5R)-isomer. Repetitive plug filtration of the filtrate ($SiO_2$, ethyl acetate, ethyl acetate/heptane 7:3 and 1:1) gave 0.05 g of the (5S)-isomer.

$^1$H-NMR (5R-isomer): 7.47 (br. s, 1H), 7.33-7.19 (m, 5H), 3.80 (t, J=7.5, 1H), 3.10 (dd, J=14.1, 5.4, 1H), 2.99 (dd, J=14.1, 4.9, 1H), 1.97-1.87 (m, 1H), 1.71-1.59 (m, 2H), 1.59-1.52 (m, 1H), 1.46-1.34 (m, 1H), 1.31 (dq, J=13.1, 3.6, 1H), 1.15-1.09 (m, 1H), 1.09 (d, J=12.8, 1H), 0.89 (d, J=6.9, 3H), 0.87 (d, J=6.9, 3H), 0.84-0.63 (m, 2H), 0.74 (d, J=6.2, 3H).

$^{13}$C-NMR (5R-isomer): 176.57, 137.13, 129.78, 128.60, 126.82, 77.38, 60.78, 50.76, 50.69, 38.01, 34.35, 29.14, 25.19, 23.97, 22.51, 21.97, 18.36.

$^1$H-NMR (5S-isomer): 8.54 (br. s, 1H), 7.33-7.19 (m, 5H), 3.92 (t, J=5.4, 1H), 3.12-3.05 (m, 2H), 1.93-1.85 (m, 1H), 1.85-1.77 (m, 1H), 1.70-1.48 (m, 2H), 1.38-1.22 (m, 2H), 1.14-1.05 (m, 1H), 1.08 (d, J=12.6, 1H), 0.94-0.84 (m, 1H), 0.88 (d, J=6.4, 3H), 0.75 (d, J=6.9, 3H), 0.58 (d, J=6.9, 3H), 1H (NH) not assigned.

$^{13}$C-NMR (5S-isomer): 176.66, 137.41, 129.84, 128.61, 126.70, 77.26, 58.67, 50.18, 48.79, 36.69, 34.48, 29.71, 24.16, 23.84, 22.94, 22.11, 17.94.

(x) Synthesis of 6-isopropyl-9-methyl-1,4-diazaspiro[4.5]decan-2-one [Compound 24, Pro-Perfume According to Formula (VI)]

TEA (76.6 mL, 550 mmol) was added to a solution of glycinamide hydrochloride (56.40 g, 500 mmol) in methanol (580 mL). The reaction mixture was stirred for 15 min and then heated under reflux. 2-Isopropyl-5-methylcyclohexan-1-one (menthone, 33.25 g, 216 mmol) was added and the reaction mixture heated under reflux for 24 h. After cooling to room temperature, the solvent was evaporated under reduced pressure. n-Pentane (50 mL) and water (200 mL) were added and the mixture extracted. After phase separation, the aqueous phase was re-extracted with n-pentane (2×, 50 mL). The combined organic phases were washed with water (100 mL), dried ($Na_2SO_4$), filtered and concentrated under reduced pressure to afford 31.41 g of the crude product. Bulb-to-bulb distillation of 2.80 g (100° C., 0.1 mbar) to remove remaining menthone afforded 2.13 g (53%) of the title compound as a mixture of diastereoisomers (ca. 1:1). This pro-perfume compound releases menthone upon exposure to moisture.

$^1$H-NMR: 8.39 and 7.42 (br. s, 1H), 3.56 and 3.49 (dd, J=54.2, 16.3, 2H), 2.16-2.03 and 2.03-1.94 (m, 1H), 1.88 (br s, 1H), 1.92-1.70 (m, 2H), 1.70-1.52 (m, 2H), 1.41-1.31 (m, 0.5H), 1.31-1.18 (m, 2.5H), 1.04-0.75 (m, 1H), 0.95 and 0.92 (d, J=7.1, 3H), 0.91 and 0.90 (d, J=7.1, 3H), 0.91 and 0.81 (d, J=6.7, 3H).

$^{13}$C-NMR: 176.28 and 176.22, 79.78 and 79.55, 51.93 and 50.46, 50.56 and 49.71, 49.50 and 49.44, 34.51 and 34.47, 30.26 and 29.50, 25.40 and 25.10, 24.21 and 23.96, 22.74 and 22.70, 22.15 and 22.00, 18.66 and 17.91.

(y) Synthesis of 2-ethyl-2-(2-methylbutyl)imidazolidin-4-one [Compound 25, Pro-Perfume According to Formula (VI)]

5-Methyl-3-heptanone (1.74 g, 13.6 mmol) and TEA (2 mL) were added to a suspension of glycinamide hydrochloride (1.50 g, 13.6 mmol) in dry methanol (15 mL). The mixture was heated to reflux for 18 h. After cooling to room temperature, the solvent was removed under reduced pressure. Then demineralized water (20 mL) was added to the residue, and the mixture extracted with ethyl acetate (3×20 mL). The combined organic phases were dried ($Na_2SO_4$) and concentrated to give, after removal of remaining volatile compounds by bulb-to-bulb distillation and drying under high vacuum, 0.26 g (10%) of the title compound as a mixture of diastereoisomers. This pro-perfume compound releases 5-methyl-3-heptanone upon exposure to moisture.

$^1$H-NMR (400 MHz): 7.77 and 7.62 (s, 1H), 3.49 and 3.48 (d, J=1.4 and 2.0, 2H), 1.97 (br. s, 1H), 1.74-1.57 (m, 3H), 1.56-1.29 (m, 3H), 1.29-1.14 (m, 1H), 0.98 and 0.96 (d, J=3.2 and 3.8, 3H), 0.94 (t, J=7.6, 3H), 0.88 and 0.87 (t, J=7.4 and 7.6, 3H).

$^{13}$C-NMR (100.6 MHz): 176.90 and 176.86, 79.80 and 79.73, 49.67 and 49.41, 46.04 and 45.87, 33.41 and 33.19, 31.24 and 30.87, 30.27 and 30.13, 21.11 and 21.05, 11.35 and 11.26, 7.98.

(z) Synthesis of 1,3-dibenzyl-2-phenylimidazolidine [Compound 26, Pro-Perfume According to Formula (VII)]

Under vigorous stirring, benzaldehyde (0.53 g, 5.0 mmol) was slowly added to a solution of N,N'-dibenzylethane-1,2-diamine (1.20 g, 5.0 mmol) in water (7.5 mL). The reaction mixture was stirred for 3 h, then the residue was filtered and dried under reduced pressure to give 1.60 g (97%) of the title compound. This pro-perfume compound releases benzaldehyde upon exposure to moisture.

$^1$H-NMR (400 MHz, DMSO-d6): 7.63 (d, J=6.7, 2H), 7.41 (t, J=7.4, 2H), 7.38-7.30 (m, 1H), 7.30-7.14 (m, 10H), 3.87 (s, 1H), 3.63 (d, J=12.8, 2H), 3.23 (d, J=13.3, 2H), 3.02 (dt, J=4.6, 8.7, 2H), 2.46 (dt, J=4.6, 8.2, 2H).

$^{13}$C-NMR (100.6 MHz, DMSO-d6): 140.47, 138.90, 129.10, 128.40, 128.04, 128.01, 126.65, 87.95, 55.98, 50.12.

(aa) Synthesis of (±)-1,3-dibenzyl-2-(undecan-2-yl)imidazolidine [Compound 27, Pro-Perfume According to Formula (VII)]

A mixture of (±)-2-methylundecanal (200 μL) and N,N'-dibenzylethane-1,2-diamine (200 μL) in methanol (2 mL) was stirred at room temperature for 24 h to give a biphasic system. Centrifugation and pipetting of the lower phase afforded 0.13 g of the title compound. This pro-perfume compound releases 2-methylundecanal upon exposure to moisture.

$^1$H-NMR: 7.40-7.34 (m, 4H), 7.34-7.25 (m, 4H), 7.26-7.20 (m, 2H), 3.95 (dd, J=18.0, 13.8, 2H), 3.56 (dd, J=19.2, 13.5, 2H), 3.23 (d, J=3.2, 1H), 2.90-2.81 (m, 2H), 2.55-2.45 (m, 2H), 1.71-1.57 (m, 2H), 1.45-1.34 (m, 1H), 1.34-1.18 (m, 14H), 1.02 (d, J=6.7, 3H), 0.88 (t, J=6.9, 3H).

$^{13}$C-NMR: 140.59, 140.43, 128.49, 128.46, 128.19 (2×), 126.76, 126.75, 90.69, 61.02, 60.43, 51.17, 50.81, 37.77, 32.97, 31.94, 30.08, 29.75, 29.68, 29.39, 27.83, 22.71, 15.38, 14.13.

(ab) Synthesis of (±)-1,3-dibenzyl-2-(phenylpropyl) imidazolidine [Compound 28, Pro-Perfume According to Formula (VII)]

A mixture of (±)-3-phenylbutanal (0.62 g, 4.2 mmol), N,N'-dibenzyl-1,2-ethanediamine (1.00 g, 4.2 mmol, 1 eq.) and $K_2CO_3$ in ethanol (6.2 mL) was heated to 60° C. for 24 h. Then the solvent was removed under vacuum at 40° C. The residue was taken up in diethyl ether and the solvent evaporated to yield 1.28 g (83%) of the title compound as a mixture of diastereoisomers. This pro-perfume compound releases 3-phenylbutanal upon exposure to moisture.

$^{1}$H-NMR (400 MHz, DMSO-ds): 7.37-7.19 (m, 12H), 7.17-7.07 (m, 3H), 3.85 (d, J=13.3, 1H), 3.72 (d, J=13.3, 1H), 3.43 (d, J=4.6, 1H), 3.40 (d, J=4.6, 1H), 3.21-3.16 (m, 1H), 3.06-2.95 (m, 1H), 2.84-2.71 (m, 2H), 2.54-2.42 (m, 2H), 1.92-1.82 (m, 2H), 1.80-1.69 (m, 2H), 1.15 (d, J=7.2, 3H).

$^{13}$C-NMR (100.6 MHz, DMSO-ds): 147.97, 139.69, 139.53, 128.37, 128.33, 128.18, 128.05, 128.03, 126.70, 126.64, 126.62, 125.48, 83.23, 58.39, 57.92, 49.92, 40.85, 35.59, 23.47.

(ac) Synthesis of (±)-3,5-bis(1-(4-isopropylphenyl) propan-2-yl)dihydro-1H,3H,5H-oxazolo[3,4-c]oxazole [Compound 29, Pro-Perfume According to Formula (VIII)]

A solution of 2-amino-1,3-propanediol (2.32 g, 25 mmol) and (±)-3-(4-isopropylphenyl)-2-methylpropanal (9.51 g, 50 mmol) in toluene (50 mL) was heated under reflux for 20 h with a Dean-Stark apparatus to remove water. After cooling to room temperature, the reaction mixture was concentrated and dried under high vacuum (1 h) to give 11.20 g (quant.) of the title compound as a mixture of four diastereoisomers (ca. 1:1:1:1). This pro-perfume compound releases 3-(4-isopropylphenyl)-2-methylpropanal upon exposure to moisture.

$^{1}$H-NMR: 7.19-7.03 (m, 8H), 4.36-4.28 (m, 2H), 4.15-4.05 (m, 2H), 3.86-3.77 (m, 1H), 3.61-3.69 (m, 2H), 3.06 and 3.01 (dd, J=13.5, 3.5, 1H), 2.97-2.82 (m, 3H), 2.37-2.20 (m, 2H), 1.93-1.80 (m, 2H), 1.24 and 1.23 (t, J=3.4, 12H), 0.92 and 0.90 (d, J=6.7, 3H), 0.88 and 0.86 (d, J=7.1, 3H).

$^{13}$C-NMR: 146.28 (2×) and 146.17 (2×), 138.30, 138.23, 138.19 and 138.18; 129.14, 129.10 and 128.98 (2×); 126.29, 126.27, 126.21 (2×); 101.42, 101.23, 100.68 and 100.65; 70.11, 69.79, 69.76 and 69.50; 62.88 (3×) and 62.80; 40.35, 40.28, 39.98 and 39.94; 38.99, 38.84, 37.11 and 36.72; 33.68 (2×) and 33.66 (2×); 24.07 (4×), 15.52, 15.30, 13.64 and 13.42.

(ad) Synthesis of (±)-3,5-di(undecan-2-yl)dihydro-1H,3H,5H-oxazolo[3,4-c]oxazole [Compound 30, Pro-Perfume According to Formula (VIII)]

The compound was prepared as described for Compound 29 with (±)-2-methylundecanal (9.22 g, 50 mmol) to give 10.73 g (quant.) of a mixture of four diastereoisomers (ca. 1:1:1:1). This pro-perfume compound releases 2-methylundecanal upon exposure to moisture.

$^{1}$H-NMR: 4.25-4.19 (m, 2H), 4.07-3.97 (m, 2H), 3.75-3.68 (m, 1H), 3.63-3.55 (m, 2H), 1.72-1.45 (m, 4H), 1.45-1.15 (m, 28H), 1.15-1.99 (m, 2H), 0.93, 0.92 and 0.91 (2×) (d, J=6.4, 6H), 0.88 (t, J=6.9, 6H).

$^{13}$C-NMR: 101.91, 101.72, 101.27 and 101.22; 69.97, 69.73, 69.67 and 69.44; 62.73, 62.68 (2×) and 62.62; 37.80, 37.73 (2×) and 37.64; 32.99, 32.81, 31.23 and 30.98; 31.93 (4×); 30.04, 30.00 (2×) and 29.98; 29.73, 29.70 and 29.66 (6×); 29.37 (4×); 27.35, 27.24 and 27.18 (2×); 22.71 (4×); 15.68, 15.60, 13.85 and 13.57; 14.13 (4×).

(ae) Synthesis of ethyl (E/Z)-2-acetyl-4-methyltridec-2-enoate [Compound 31, Pro-Perfume According to Formula (IX)]

A mixture of ethyl acetoacetate (26.03 g, 0.2 mol), (±)-2-methylundecnal (36.86 g, 0.2 mol) and piperidine (68.12 mg, 0.8 mmol) was heated at 50° C. for 1 h. Vacuum (100 mbar) was applied, and the mixture stirred at 50° C. for 8 h, while distilling off a volatile fraction (2.95 g). The crude product (59.08 g) was obtained as the residue, a part of which (29.00 g) was dried under high vacuum (0.09 mbar) for 12 h to afford the title compound as a mixture of isomers (E/Z ca. 38:62). This pro-perfume compound releases 2-methylundecanal upon exposure to moisture.

$^{1}$H-NMR (Z-isomer): 6.59 (d, J=10.6, 1H), 4.30 (q, J=7.2, 2H), 2.60-2.48 (m, 1H), 2.31 (s, 3H), 1.45-1.15 (m, 16H), 1.33 (t, J=7.2, 3H), 1.07 (d, J=6.4, 3H), 0.88 (t, J=6.9, 3H).

$^{13}$C-NMR (Z-isomer): 195.22, 166.72, 153.43, 135.83, 61.17, 36.54, 34.95, 31.89, 29.61, 29.58, 29.52, 29.31, 27.41, 26.87, 22.68, 19.92, 14.20, 14.11.

$^{1}$H-NMR (E-isomer): 6.67 (d, J=11.0, 1H), 4.25 (q, J=7.1, 2H), 2.54-2.42 (m, 1H), 2.36 (s, 3H), 1.43-1.15 (m, 16H), 1.31 (t, J=7.1, 3H), 1.03 (d, J=6.4, 3H), 0.88 (t, J=6.9, 3H).

$^{13}$C-NMR (E-isomer): 201.27, 164.64, 153.66, 134.52, 61.13, 36.60, 34.09, 31.89, 31.34, 29.64, 29.59, 29.52, 29.31, 27.49, 22.68, 20.13, 14.15, 14.11.

(af) Synthesis of 2-phenylethyl 2-oxo-2-phenylacetate [Compound 32, Pro-Perfume According to Formula (X)]

At 0° C. a solution of N,N'-dicyclohexylcarbodiimide (DCC, 5.54 g, 27 mmol) in dichloromethane (30 mL) was added dropwise to a solution of DMAP (0.28 g, 0.3 mmol), 2-phenylethanol (5.00 g, 41 mmol) and 2-oxo-2-phenylacetic acid (benzoylformic acid, 3.43 g, 23 mmol) in dichloromethane (140 mL). After stirring for 10 min, the reaction mixture was left warming to room temperature. After 6 h, the reaction mixture was filtered through Celite®, extracted with diethyl ether (2×), washed with water (3×), an aqueous solution of HCl (10%, 3×) and a saturated aqueous solution of $NaHCO_3$. The organic phase was dried ($Na_2SO_4$), filtered and concentrated. Column chromatography ($SiO_2$, n-heptane/diethyl ether 8:2 to 7:3) afforded 5.52 g (94%) of the title compound. This pro-perfume compound releases 2-phenylacetaldehyde upon exposure to light.

$^{1}$H-NMR: 7.88-7.83 (m, 2H), 7.65-7.60 (m, 1H), 7.48-7.42 (m, 2H), 7.35-7.29 (m, 2H), 7.29-7.23 (m, 3H), 4.62 (t, J=7.1, 2H), 3.09 (t, J=7.1, 2H).

$^{13}$C-NMR: 186.28, 163.72, 136.95, 134.87, 132.33, 130.02, 129.01, 128.85, 128.69, 126.86, 66.40, 34.94.

(ag) Synthesis of (Z)-3-hexenyl 2-oxo-2-phenylacetate [Compound 33, Pro-Perfume According to Formula (X)]

A solution of benzoylformic acid (5.55 g, 37.0 mmol), DMAP (0.45 g, 3.7 mmol) and (Z)-3-hexenol (6.61 g, 50.0 mmol) in dichloromethane (86 mL) was cooled on an ice-bath before DCC (9.00 g, 43.6 mmol) in dichloromethane (40 mL) was added during 45 min. The reaction mixture was stirred for 10 min at 0° C., then at room temperature for 48 h. The precipitate was filtered off and the filtrate taken up in ether, washed with water, an aqueous solution of HCl (10%), a saturated solution of $NaHCO_3$ (3×) and water. The organic layer was dried ($Na_2SO_4$), concentrated and chromatographed ($SiO_2$, heptane/ether 7:3) to give 8.04 g (93%) of the title compound. This pro-perfume compound releases (Z)-3-hexenal upon exposure to light.

$^1$H-NMR (360 MHz): 8.04-7.98 (m, 2H), 7.69-7.62 (m, 1H), 7.55-7.47 (m, 2H), 5.61-5.51 (m, 1H), 5.41-5.31 (m, 1H), 4.39 (t, J=6.9, 2H), 2.58-2.49 (m, 2H), 2.12-2.01 (m, 2H), 0.95 (t, J=7.5, 3H).

$^{13}$C-NMR (90.6 MHz): 186.36, 163.87, 135.39, 134.90, 132.49, 130.07, 128.89, 122.87, 65.63, 26.64, 20.66, 14.15.

(ah) Synthesis of (E)-3,7-dimethylocta-2,6-dienyl 2-oxo-2-phenylacetate [Compound 34, Pro-Perfume According to Formula (X)]

A solution of ethyl 2-oxo-2-phenylacetate (17.6 g, 99 mmol), (E)-3,7-dimethylocta-2,6-dienol (18.5 g, 120 mmol) and $NaOCH_3$ (30% in methanol, 1.5 mL) in cyclohexane (170 mL) was heated under reflux for 72 h. After cooling to room temperature the reaction mixture was taken up in ether, washed with water (pH ca. 7), dried ($Na_2SO_4$), filtered and concentrated. Column chromatography ($SiO_2$, heptane/ether 8:2) afforded 14.5 g (52%) of the title compound. This pro-perfume compound releases (E)-3,7-dimethylocta-2,6-dienal upon exposure to light.

$^1$H-NMR (360 MHz): 8.04-7.97 (m, 2H), 7.69-7.62 (m, 1H), 7.55-7.46 (m, 2H), 5.52-5.54 (m, 1H), 5.13-5.04 (m, 1H), 4.91 (d, J=7.2, 2H), 2.20-2.03 (m, 4H), 1.78 (s, 3H), 1.67 (s, 3H), 1.60 (s, 3H).

$^{13}$C-NMR (90.6 MHz): 186.46, 163.90, 144.40, 134.85, 132.58, 132.03, 130.04, 128.87, 123.55, 117.07, 63.00, 39.56, 26.24, 25.68, 17.70, 16.63.

(ai) Synthesis of (Z)-dodec-4-en-1-yl 2-oxo-2-phenylacetate [Compound 35, Pro-Perfume According to Formula (X)]

A solution of benzoylformic acid (19.4 g, 129 mmol), DMAP (1.58 g, 12.9 mmol), (Z)-4-dodecenol (25.0 g, 136 mmol) in dichloromethane (200 mL) was cooled on an ice bath before a solution of DCC (29.3 g, 142 mmol) in dichloromethane (100 mL) was added dropwise during 30 min. The reaction mixture was stirred for 10 min at 0° C., then at room temperature for 4 h. The precipitate formed during reaction was filtered on sintered glass and rinsed with dichloromethane (50 mL). The filtrate was concentrated, taken up in diethyl ether (300 mL), washed with water (3×, 100 mL), an aqueous solution of HCl (10%, 3×100 mL), water (100 mL), a saturated aqueous solution of $NaHCO_3$ (3×100 mL). Each aqueous phase was reextracted with ether (200 mL). The combined organic phases were dried ($Na_2SO_4$), filtered through sintered glass and concentrated. An overhead fraction was removed by distillation in vacuo (0.1 mbar, 61° C.). The residue was filtered through sintered glass to give 37.4 g (74%) of the title compound. This pro-perfume compound releases (Z)-4-dodecenal upon exposure to light.

$^1$H-NMR (360 MHz): 8.04-7.98 (m, 2H), 7.79-7.62 (m, 1H), 7.55-7.47 (m, 2H), 5.49-5.29 (m, 2H), 4.39 (t, J=6.7, 2H), 2.18 (q, J=7.3, 2H), 2.01 (q, J=6.9, 2H), 1.89-1.79 (m, 2H), 1.38-1.17 (m, 10H), 0.87 (t, J=6.7, 3H).

$^{13}$C-NMR (90.6 MHz): 186.38, 163.95, 134.89, 132.51, 131.67, 130.02, 128.90, 127.56, 65.73, 31.86, 29.67, 29.27, 29.22, 28.43, 27.25, 23.41, 22.67, 14.12.

(aj) Synthesis of (±)-(2,4-dimethylcyclohex-3-en-1-yl)methyl 2-oxo-2-phenylacetate [Compound 36, Pro-Perfume According to Formula (X)]

A solution of benzoylformic acid (24.0 g, 160 mmol), DMAP (1.96 g, 16 mmol) and (±)-(2,4-dimethylcyclohex-3-en-1-yl)methanol (38.1 g, 272 mmol, cis/trans ca. 4:1) in dichloromethane (250 mL) was cooled on an ice bath before a solution of DCC (38.0 g, 184 mmol) in dichloromethane (100 mL) was added dropwise during 30 min. The reaction mixture was stirred for 10 min at 0° C., then at room temperature for 3 h. The precipitate formed during reaction was filtered through sintered glass and rinsed with dichloromethane (50 mL). The filtrate was concentrated and taken up in diethyl ether (500 mL), washed with water (3×, 100 mL), an aqueous solution of HCl (10%, 3×100 mL), water (100 mL), a saturated aqueous solution of $NaHCO_3$ (3×100 mL). Each aqueous phase was reextracted with ether (300 mL). The combined organic phases were dried ($Na_2SO_4$), filtered, concentrated and dried under vacuum (0.5 mbar, 2 h). Another filtration through sintered glass, removing an overhead fraction by distillation in vacuo (2×, 0.08 mbar, 35-38° C.) and filtration through sintered glass gave 37.5 g (82%) of the title compound as a mixture of cis/trans-isomers (ca. 4:1). This pro-perfume compound releases (±)-2,4-dimethylcyclohex-3-ene-1-carbaldehyde upon exposure to light.

$^1$H-NMR (400 MHz): 8.03-7.97 (m, 2H), 7.69-7.62 (m, 1H), 7.55-7.48 (m, 2H), 5.36-5.29 and 5.21-5.16 (m, 1H), 4.50-4.26 (m, 2H), 2.44-2.30 (m, 1H), 2.21-2.09 (m, 1H), 2.08-1.84 (m, 2H), 1.69-1.42 (m, 2H), 1.65 (s, 3H), 1.05 and 0.91 (d, J=6.9 and 7.2, 3H).

$^{13}$C-NMR (100.6 MHz, cis-isomer): 186.52, 164.17, 134.90, 133.06, 132.50, 129.97, 128.92, 126.50, 67.99, 35.92, 30.57, 29.21, 23.46, 21.25, 15.68.

$^{13}$C-NMR (100.6 MHz, trans-isomer): 186.48, 164.17, 134.90, 133.16, 132.50, 129.99, 128.92, 126.39, 68.84, 39.71, 31.99, 28.72, 24.72, 20.58, 15.68.

(ak) Synthesis of (1R,2S,5R)-2-isopropyl-5-methylcyclohexyl 2-oxo-2-phenylacetate [Compound 37, Pro-Perfume According to Formula (X)]

A solution of benzoylformic acid (2.01 g, 13.3 mmol), DMAP (1.62 g, 13.3 mmol) and (−)-menthol (2.08 g, 13.3 mmol) in dichloromethane (30 mL) was cooled on an ice-bath before DCC (2.75 g, 13.3 mmol) in dichloromethane (14 mL) was added during 30 min. The reaction mixture was stirred for 10 min at 0° C., then at room temperature for 21 h. The precipitate was filtered off and the filtrate taken up in ether, washed with water (3×), an aqueous solution of HCl (10%, 3×6 mL), water, a saturated solution of $NaHCO_3$ (3×) and water. The organic layer was concentrated and dried under high vacuum (0.2 mbar, 1 h). Repetitive column chromatography ($SiO_2$, heptane/acetone 8:2) gave 2.00 g (52%) of the title compound. This pro-perfume compound releases (−)-menthone upon exposure to light.

$^1$H-NMR (400 MHz): 8.01-7.96 (m, 2H), 7.69-7.62 (m, 1H), 7.55-7.48 (m, 2H), 5.01 (dt, J=10.9, 4.4, 1H), 2.22-2.14 (m, 1H), 2.01-1.91 (m, 1H), 1.78-1.68 (m, 2H), 1.65-1.47

(m, 2H), 1.19 (q, J=11.7, 1H), 1.19-1.05 (m, 1H), 0.98-0.83 (m, 1H), 0.96 (d, J=6.8, 3H), 0.91 (d, J=7.2, 3H), 0.85 (d, J=7.0, 3H).

$^{13}$C-NMR (100.6 MHz): 186.81, 163.90, 134.80, 132.57, 129.92, 128.90, 76.97, 46.83, 40.63, 34.07, 31.55, 26.17, 23.34, 21.97, 20.68, 16.16.

(al) Synthesis of dec-9-en-1-yl (E)-3-(2-hydroxyphenyl)acrylate [Compound 38, Pro-Perfume According to Formula (XI)]

A mixture of ethyl (E)-3-(2-hydroxyphenyl)acrylate (5.00 g, 26.0 mmol), dec-9-enol (6.10 g, 39.0 mmol) and tetraisopropoxytitanium (1.00 g, 3.5 mmol) was heated for 2 h at 150° C. in a Dean-Stark apparatus to remove ethanol. After cooling to room temperature, the mixture was taken up in diethyl ether and washed with a saturated aqueous solution of NaCl. The organic phase was dried ($Na_2SO_4$), filtered and concentrated. Bulb-to-bulb distillation (0.1 mbar, 100° C.) to remove the remaining volatiles afforded a residue, which was treated with n-heptane (3×). The heptane phases were decanted, concentrated and dried under vacuum to yield the crude compound. Column chromatography ($SiO_2$, n-heptane/diethyl ether 8:2 to 1:1) afforded 2.47 g (31%) of the title compound. This pro-perfume compound releases 2H-chromen-2-one and dec-9-enol upon exposure to light.

$^{1}$H-NMR (400 MHz): 8.07 (d, J=16.2, 1H), 7.46 (dd, J=7.7, 1.5, 1H), 7.27-7.19 (m, 1H), 7.08 (s, 1H), 6.94-6.84 (m, 2H), 6.67 (d, J=16.2, 1H), 5.87-5.75 (m, 1H), 5.03-4.90 (m, 2H), 4.23 (t, J=6.7, 2H), 2.08-2.00 (m, 2H), 1.76-1.66 (m, 2H), 1.46-1.23 (m, 11H).

$^{13}$C-NMR (100.6 MHz): 168.83, 155.60, 140.87, 139.19, 131.44, 129.22, 121.74, 120.60, 118.26, 116.47, 114.16, 64.98, 33.78, 29.36, 29.23, 29.04, 28.90, 28.71, 25.96.

(Am) Synthesis of Compounds 39-44 [Pro-Perfumes According to Formula (XII)]

An aqueous solution of KOH (10%, 75 mL) was cooled to 0° C. Hexanal (150 g, 1.5 mol) was added dropwise over 1 h, keeping the temperature of the reaction mixture below 5° C. and then stirred an additional 3 h. Diethyl ether (200 mL) was added to the cold reaction mixture, and the aqueous and organic phases of the reaction mixtures were separated. The aqueous phase was extracted with ether (200 mL) and the combined organic phases were extracted with water until the aqueous phase was neutral by pH paper. The ether phase was dried ($Na_2SO_4$), filtered and concentrated. Adipic acid (2 g) was added and the sample fractionally distilled under vacuum. Hexanal, liberated from the decomposing aldoxane, was removed as the distillation flask was heated to 95° C., then the hexanal aldol (2-butyl-3-hydroxyoctanal) was distilled (bp, 103-104° C., 2.6 Pa). It was obtained in 40% yield (59.2 g, 0.30 mol) and was collected in receiving flasks cooled with dry ice/acetone slurries to minimize dimerization. The freshly distilled aldol and the desired aldehyde $R^{16}$CHO (0.9-1.1 eq., Table 1) were weighed into a flask and stirred for at least 1 d at room temperature to allow formation of the corresponding pro-perfumes (±)-5-butyl-2-heptyl-6-pentyl-1,3-dioxan-4-ol (Compound 39), (±)-5-butyl-2-nonyl-6-pentyl-1,3-dioxan-4-ol (Compound 40), (±)-5-butyl-6-pentyl-2-undecyl-1,3-dioxan-4-ol (Compound 41), (±)-5-butyl-6-pentyl-2-(2-phenylpropyl)-1,3-dioxan-4-ol (Compound 42), (±)-2-benzyl-5-butyl-6-pentyl-1,3-dioxan-4-ol (Compound 43) and (±)-5-butyl-2-(4-(tert-butyl)phenethyl)-6-pentyl-1,3-dioxan-4-ol (Compound 44), respectively. GCMS analysis of the mixture (as the acetate derivatives) showed that the desired pro-perfume, as a mixture of stereoisomers, was the major component in the resulting materials. Characterizing MS fragments (of the acetate derivatives) are listed in Table 1 below and confirm formation of the desired compounds. Acetates for GC analysis were prepared by mixing the sample with the acetylating reagent at about a 1:4 volume ratio in a GC vial. The reagent was prepared by mixing acetic anhydride and pyridine (each 1 mL) and DMAP (50 mg). The fragment ions listed in Table 1 are the molecular ion ($M^+$), the $(M-1)^+$ ion, the $(M-R^{16})^+$ ion [according to formula (XII)], the $(M-59)^+$ ion (loss of acetate radical) and the $(M-60)^+$ ion (loss of acetic acid). Pro-perfumes prepared in this manner were used without further purification.

TABLE 1

MS characterization of pro-perfume compounds 39 to 44 according to formula (XII), and aldehydes used for their formation and released from them in use.

| Aldehyde ($R^{16}$CHO) | Molar ratio (aldol:aldehyde) | MS fragment ions, m/z (relative abundance) $M^+$ | $(M-1)^+$ | $(M-R^{16})^+$ | $(M-59)^+$ | $(M-60)^+$ |
|---|---|---|---|---|---|---|
| Octanal (Compound 39) | 1:1 | 370 (<1) | 369 (<1) | 271 (5) | 311 (1) | 310 (<1) |
| Decanal (Compound 40) | 1:1 | 398 (<1) | 397 (<1) | 271 (7) | 339 (1) | 338 (<1) |
| Dodecanal (Compound 41) | 1:1 | 426 (nd) | 425 (<1) | 271 (9) | 367 (<1) | 366 (<1) |
| 3-Phenylbutanal (Compound 42) | 1:0.9 | 390 (1) | 389 (<1) | 271 (1) | 331 (2) | 330 (2) |
| 2-Phenylacetaldehyde (Compound 43) | 1:1.1 | 362 (nd) | 361 (<1) | 271 (17) | 303 (1) | 302 (1) |
| 3-(4-tert-Butylphenyl)propanal (Compound 44) | 1:1 | 432 (<1) | 431 (<1) | 271 (<1) | 373 (1) | 372 (2) |

nd = not detected

The pro-perfume compounds 39-44 release the aldehydes listed in Table 1 upon exposure to moisture and/or to heat.

(an) Synthesis of (E)-3,7-dimethylocta-2,6-dien-1-yl palmitate [Compound 45, Pro-Perfume According to Formula (XIII)]

TEA (1.7 mL, 12 mmol) was rapidly added to a solution of (E)-3,7-dimethylocta-2,6-dien-1-ol (geraniol, 1.54 g 10 mmol) in dichloromethane (50 mL). The reaction mixture was cooled to 10-15° C. on an ice bath, before palmitoyl chloride (3.45 mL, 3.09 g, 11 mmol) was added dropwise during 15 min. The reaction mixture was left warming to room temperature and stirred overnight. The reaction mixture was poured into a saturated aqueous solution of $NaHCO_3$ (50 mL). The organic phase was decanted and the aqueous layer was re-extracted with dichloromethane (50 mL). The combined organic phases were washed with a saturated aqueous solution of NaCl (50 mL), dried ($Na_2SO_4$), filtered and concentrated. The product was taken up in warm heptane (5 mL) and left cooling to room temperature. After storing in the fridge overnight, the product was filtered and concentrated to afford 3.96 g (quant.) of the title compound. This pro-perfume compound releases (E)-3,7-dimethylocta-2,6-dien-1-ol (geraniol) upon exposure to moisture and enzymes (such as lipases).

$^1$H-NMR: 5.37-5.30 (m, 1H), 5.12-5.05 (m, 1H), 4.59 (d, J=7.1, 2H), 2.29 (t, J=7.5, 2H), 2.14-2.01 (m, 4H), 1.70 (s, 3H), 1.68 (s, 3H), 1.66-1.58 (m, 2H), 1.60 (s, 3H), 1.36-1.20 (m, 24H), 0.88 (t, J=6.9, 3H).

$^{13}$C-NMR: 173.95, 142.11, 131.81, 123.78, 118.44, 61.18, 39.55, 34.42, 31.94, 29.71 (2×), 29.69, 29.67 (2×), 29.62, 29.49, 29.38, 29.29, 29.17, 26.32, 25.69, 25.04, 22.71, 17.69, 16.47, 14.13.

(ao) Synthesis of (±)-3-methyl-5-phenylpentyl palmitate [Compound 46, Pro-Perfume According to Formula (XIII)]

A solution of palmitic acid (7.00 g, 27.3 mmol), DMAP (0.33 g, 2.7 mmol) and (±)-3-methyl-5-phenylpentan-1-ol (8.10 g, 45.4 mmol) in dichloromethane (60 mL) was cooled on an ice-bath before DCC (6.40 g, 31.0 mmol) in dichloromethane (40 mL) was added during 15 min. The reaction mixture was stirred for 10 min at 0° C., then at room temperature for 5 h. The precipitate was filtered off and the filtrate taken up in ether, washed with water (3×), an aqueous solution of HCl (10%, 3×6 mL) and a saturated solution of $NaHCO_3$ (3×). The organic layer was dried ($Na_2SO_4$), filtered and concentrated. Repetitive bulb-to-bulb distillation (0.2 mbar 100° C.) to remove volatiles gave 7.99 g (71%) of the title compound. This pro-perfume compound releases 3-methyl-5-phenylpentan-1-ol upon exposure to moisture and enzymes (such as lipases).

$^1$H-NMR (400 MHz): 7.31-7.23 (m, 2H), 7.21-7.13 (m, 3H), 4.18-4.04 (m, 2H), 2.72-2.52 (m, 2H), 2.27 (t, J=7.5, 2H), 1.77-1.54 (m, 5H), 1.54-1.41 (m, 2H), 1.37-1.18 (m, 24H), 0.97 (d, J=6.4, 3H), 0.88 (t, J=6.8, 3H).

$^{13}$C-NMR (100.6 MHz): 173.99, 142.63, 128.33, 128.31, 125.67, 62.60, 38.76, 35.42, 34.42, 33.28, 31.94, 29.71 (3×) 29.67 (2×), 29.63, 29.51, 29.50, 29.38, 29.29, 29.18, 25.02, 22.71, 19.42, 14.13.

(ap) Synthesis of 1-butoxy-3-((1E,4Z)-hepta-1,4-dien-1-yl)benzene [Compound 47, Pro-Perfume According to Formula (XIV)]

(a) 3-Butoxybenzaldehyde (5.35 g, 30.0 mmol) was added during 25 min with a syringe to an ice-cold Grignard reagent prepared from Mg turnings (0.95 g, 39.1 mmol) and (Z)-chlorohex-3-ene (4.63 g, 39.0 mmol) in THF (65 mL). The temperature was maintained at 3-5° C. during the introduction. After cooling to room temperature, the reaction mixture was poured into an aqueous solution of HCl (10%, 100 mL) and ice. Diethyl ether (200 mL) was added, and the organic phase was washed with a saturated aqueous solution of NaCl (2×). The aqueous phases were re-extracted with ether (100 mL). The combined organic layers were dried ($Na_2SO_4$) and concentrated to give 7.81 g (99%) of (Z)-1-(3-butoxyphenyl)hept-4-en-1-ol.

$^1$H-NMR: 7.27-7.20 (m, 1H), 6.93-6.86 (m, 2H), 6.84-6.77 (m, 1H), 5.44-5.31 (m, 2H), 4.68-4.61 (m, 1H), 3.96 (t, J=6.4, 2H), 2.19-1-98 (m, 4H), 1.90 (br. s, 1H), 1.90-1.70 (m, 4H), 1.55-1.42 (m, 2H), 0.98 (t, J=7.4, 3H), 0.95 (t, J=7.4, 3H).

$^{13}$C-NMR: 159.35, 146.39, 132.51, 129.41, 128.25, 118.02, 113.53, 111.97, 74.14, 67.65, 38.91, 31.37, 23.61, 20.55, 19.27, 14.32, 13.87.

(b) A solution of (Z)-1-(3-butoxyphenyl)hept-4-en-1-ol (7.29 g, 27.8 mmol) and p-toluenesulfonic acid monohydrate (0.29 g, 1.4 mmol) in toluene (100 mL) was heated under reflux in a Dean-Stark apparatus for 3 h. After cooling to room temperature, the reaction mixture was poured into a saturated aqueous solution of $NaHCO_3$ (100 mL). The aqueous phases were re-extracted with ether (100 mL). The combined organic layers were washed with a saturated solution of NaCl (50 mL), dried ($Na_2SO_4$) and concentrated. Column chromatography ($SiO_2$, n-heptane/ethyl acetate 99:1) afforded 5.13 g (72%) of the title compound. This pro-perfume compound releases 3-butoxybenzaldehyde and (Z)-hex-3-en-1-al upon exposure to air/oxygen.

$^1$H-NMR (600 MHz): 7.18 (t, J=7.9, 1H), 6.91 (d, J=7.7, 1H), 6.90-6.86 (m, 1H), 6.76-6.71 (m, 1H), 6.36 (d, J=15.8, 1H), 6.18 (dt, J=15.8, 6.6, 1H), 5.53-5.46 (m, 1H), 5.45-5.38 (m, 1H), 3.95 (t, J=6.6, 2H), 2.94 (t, J=6.7, 2H), 2.13-2.06 (m, 2H), 1.79-1.72 (m, 2H), 1.54-1.42 (m, 2H), 0.99 (t, J=7.5, 3H), 0.97 (t, J=7.3, 3H).

$^{13}$C-NMR (151.0 MHz): 159.36, 139.20, 133.03, 129.89, 129.37, 129.29, 125.99, 118.52, 113.13, 111.96, 67.59, 31.39, 30.60, 20.55, 19.28, 14.29, 13.87.

(aq) Synthesis of 1-(3-(2,6-dimethyloct-7-en-2-yloxy)prop-1-enyl)-4-methoxybenzene [Compound 48, Pro-Perfume According to Formula (XV)]

Following a literature procedure (I. Ambrogio, G. Fabrizi, S. Cacchi, S. T. Henriksen, R. Fristrup, D. Tanner, P.-O. Norrby, Organometallics, 2008, 27, 3187-3195), cinnamyl ethers were prepared by the Heck reaction between aryl halides and allyl ethers.

General procedure: an alcohol was slowly added to a mixture of NaH (60% in mineral oil) in dimethylformamide (DMF) under $N_2$. Using an addition funnel, allyl bromide was added at a rate that allowed the ensuing exotherm to maintain the temperature of the mixture at about 70° C. The mixture was stirred an additional 15 min and then water was added. The mixture was diluted with diethyl ether, and after washing with water, the organic phase was dried ($Na_2SO_4$), filtered and concentrated. After flash chromatography ($SiO_2$), sometimes followed by bulb-to-bulb distillation, the allyl ethers were obtained in yields of 29-90%.

The aryl halide was added to a mixture of the allyl ether, tetrabutylammonium acetate, palladium (II) acetate and DMF. The mixture was placed in a preheated 90° C. oil bath. The reaction progress was monitored by GC analysis and upon consumption of the aryl halide (0.5-2.0 h for aryl iodides and 16-24 h for aryl bromides), the reaction mixture was removed from the oil bath. Water and diethyl ether were added to the mixture and the resulting emulsion was filtered through a pad of Celite® prior to separating the phases. The ether phase was dried ($Na_2SO_4$), filtered and concentrated. Flash chromatography ($SiO_2$, hexane/$CH_2Cl_2$/ethyl acetate) yielded oils that were composed predominantly of the cinnamyl ethers.

Starting from 2,6-dimethyloct-7-en-2-ol (dihydromyrcenol) (5 g, 32 mmol), allyl bromide (19.35 g, 160 mmol), DMF (27 mL) and NaH (1.3 g, 32 mmol), 2 g (10.2 mmol, 40% yield) of 7-(allyloxy)-3,7-dimethyloct-1-ene was obtained after flash chromatography. Using this allyl ether (5.6 g, 28.5 mmol), 1-iodo-4-methoxybenzene (5 g, 21.4 mmol), tetrabutylammonium acetate (10.7 g, 35.6 mmol), $Pd(OAc)_2$ (128 mg, 570 μmol) and DMF (25 mL), 2.55 g (8.43 mmol, 39% yield) of an isomer mixture was obtained after flash chromatography ($SiO_2$, hexane/$CH_2Cl_2$/ethyl acetate 100/0/0 to 50/50/0 then to 99/0/1) containing 71% of the title compound (E/Z=12.8:1). This pro-perfume compound releases 4-methoxybenzaldehyde, 2,6-dimethyloct-7-en-2-yl formate and 2,6-dimethyloct-7-en-2-ol upon exposure to air/oxygen and to moisture.

$^1$H-NMR (400 MHz, E-isomer): 7.30 (d, J=8.8, 2H), 6.82 (d, J=8.8, 2H), 6.52 (d, J=15.9, 1H), 6.13 (dt, J=15.9, 6.0, 1H), 5.69 (ddd, J=17.3, 10.3, 7.6, 1H), 4.96 (ddd, J=17.3, 2.0, 1.2, 1H), 4.90 (ddd, J=10.3, 2.0, 0.8, 1H), 4.00 (dd, J=6.0, 1.4, 2H), 2.13 (m, 1H), 3.78 (s, 3H), 1.55-1.43 (m, 2H), 1.41-1.24 (m, 4H), 1.19 (s, 6H), 0.99 (d, J=6.9, 3H).

$^{13}$C-NMR: (100.6 MHz, E-isomer): 159.04, 144.79, 130.65, 129.93, 127.57, 125.42, 113.85, 112.42, 75.09, 62.47, 55.20, 40.33, 37.72, 37.18, 25.73, 25.72, 21.56, 20.22.

(ar) Synthesis of (E)-4-(3-((2,6,dimethyloct-7-en-2-yl)oxy)prop-1-en-1-yl)-2-methoxyphenol [Compound 49, Pro-Perfume According to Formula (XV)]

The title compound was prepared according to the general procedure described for the synthesis of Compound 48. Starting from 2,6-dimethyloct-7-en-2-ol (dihydromyrcenol), allyl bromide, NaH and DMF, 7-(allyloxy)-3,7-dimethyloct-1-ene was obtained. Using this allyl ether, 4-iodo-2-methoxyphenol, tetrabutylammonium acetate, $Pd(OAc)_2$ and DMF, the title compound was obtained after flash chromatography ($SiO_2$, hexane/ethyl acetate). This pro-perfume compound releases vanillin, 2,6-dimethyloct-7-en-2-yl formate and 2,6-dimethyloct-7-en-2-ol upon exposure to air/oxygen and to moisture.

$^1$H-NMR (600 MHz): 6.95-6.80 (m, 3H), 6.5 (d, J=15.8, 1H), 6.12 (dt, J=15.8, 6.0, 1H), 5.71 (s, 1H), 5.69 (ddd, J=17.4, 10. 4, 7.5, 1H), 4.96 (d, J=17.4, 1H), 4.91 (d, J=10.4, 1H), 4.01 (d, J=6.0, 2H), 2.13 (m, 1H), 3.87 (s, 3H), 1.54-1.43 (m, 2H), 1.41-1.24 (m, 4H), 1.20 (s, 6H), 0.99 (d, 6.7, 3H).

$^{13}$C-NMR (151.0 MHz): 146.55, 145.29, 144.80, 131.15, 129.70, 125.21, 120.29, 114.32, 112.43, 108.22, 75.20, 62.44, 55.80, 40.25, 37.72, 37.15, 25.72, 25.71, 21.56, 20.23.

(as) Synthesis of (E)-4-(3-(((Z)-hex-3-en-1-yl)oxy)prop-1-en-1-yl)-2-methoxyphenol [Compound 50, Pro-Perfume According to Formula (XV)]

The title compound was prepared according to the general procedure described for the synthesis of Compound 48. Starting from (Z)-hex-3-en-1-ol, allyl bromide, NaH and DMF, (Z)-1-(allyloxy)hex-3-ene was obtained. Using this allyl ether, 4-bromo-2-methoxyphenol, tetrabutylammonium acetate, $Pd(OAc)_2$ and DMF the title compound was obtained after flash chromatography ($SiO_2$, hexane/ethyl acetate). This pro-perfume compound releases vanillin, (Z)-hex-3-en-1-yl formate and (Z)-hex-3-en-1-ol upon exposure to air/oxygen and to moisture.

$^1$H-NMR (600 MHz): 6.93-6.83 (m, 3H), 6.52 (d, J=15.8, 1H), 6.14 (dt, J=15.8, 6.2, 1H), 5.74 (s, 1H), 5.52-5.44 (m, 1H), 5.40-5.32 (m, 1H), 4.13 (dd, J=6.3, 1.3, 2H), 3.88 (s, 3H), 3.47 (t, J=7.2, 2H), 2.37 (q, J=7.2, 2H), 2.07 (quint., J=7.5, 2H), 0.97 (t, J=7.5, 3H). $^{13}$C-NMR (151.0 MHz): 146.60, 145.53, 133.74, 132.37, 129.34, 124.81, 123.87, 120.37, 114.39, 108.26, 71.57, 69.97, 55.84, 27.88, 20.65, 14.29.

Example 2

Performance of Pro-Perfume Compositions According to the Present Invention in a Model Surface Cleaner Application Combinations of Structurally Different Pro-Perfumes of Different General Formulae Pro-perfumes according to the present invention were dissolved individually or pairwise in 2-propanol (0.2-0.4 mL). Then an aqueous solution of sodium lauryl ether sulfate (SLES 10%) was added to complete to 5 g, thus representing a simplified model surface cleaner formulation containing the pro-perfumes. In some cases, the solutions were slightly heated to improve dissolution. An aliquot of this solution (90 mg) was spread onto a glass plate (2.5×7.5 cm) and dried for 24 h. The amount of each pro-perfume originally weighed in was chosen to release a total of 0.45 mg of the corresponding perfume compound on the glass plate.

The glass plate was then placed in a homemade headspace cell (ca. 625 mL inner volume), and a continuous flow of air (ca. 200 mL/min) was aspirated through the sampling cell. The air flow was passed through activated charcoal and through a saturated aqueous solution of NaCl to ensure a constant humidity of 75%. The volatiles were then alternatively adsorbed onto a waste Tenax® cartridge for 15 min and onto a clean Tenax® cartridge for another 15 min during 3 h (180 min) to collect a total of 6 data points. The waste cartridges were discarded; the other cartridges were desorbed on a Markes TD 100-XR desorber (at 280° C. for 10 min) and the volatiles injected into an Agilent Technologies 7890A gas chromatograph equipped with a Supelco SPB1 capillary column (30 m, i.d. 0.25 mm, film 0.25 μm) and coupled to an Agilent 5975C inert MSD mass spectrometer. The volatiles were eluted with a flow of He at 0.9 mL/min using a temperature gradient moving from 40° C. (for 1 min), to 180° C. at 10° C./min and to 260° C. at 30° C./min. Headspace concentrations (in ng/L air) were obtained by external standard calibrations using different concentrations of the perfume compounds to be released in ethanol. Each calibration solution (0.2 μL) was injected onto a clean Tenax® cartridge, which was desorbed and analyzed under the same conditions. All measurements were carried out at least in duplicate.

The average headspace concentrations (mean values of the 6 data points) of perfume compounds released from the individual pro-perfumes and from the corresponding pro-perfume composition according to the present invention are listed in Table 2.

TABLE 2

Average headspace concentrations of perfume compounds released from an individual pro-perfume and from a composition of structurally different pro-perfumes according to the present invention on a glass plate after drying for 1 day.

| Compositions | Example for a pro-perfume according to formula | Avg. headspace concentration [ng/L] of perfume compound) released from the individual pro-perfume | Avg. headspace concentration [ng/L] of perfume compound) released from the pro-perfume composition | Increase of release from the pro-perfume composition vs. the individual pro-perfume |
|---|---|---|---|---|
| Compound 1 | (I) | 5.8 | 8.2 | +41% |
| Compound 24 | (VI) | 48.6 | 65.8 | +135% |
| Compound 1 | (I) | 5.8 | 10.0 | +72% |
| Compound 31 | (IX) | 29.4 | 61.3 | +209% |
| Compound 2a | (I) | 2.1 | 14.8 | +605% |
| Compound 24 | (VI) | 48.6 | 82.8 | +70% |
| Compound 2a | (I) | 2.1 | 3.0 | +43% |
| Compound 30 | (VIII) | 18.7 | 47.2 | +152% |
| Compound 4 | (I) | 1.8 | 2.0 | +11% |
| Compound 9 | (IV) | 8.7[2] | 11.9[2] | +37% |
| Compound 5 | (I) | 26.4 | 48.8 | +85% |
| Compound 9 | (IV) | 8.7[2] | 16.2[2] | +86% |
| Compound 5 | (I) | 26.4 | 51.1 | +94% |
| Compound 10 | (IV) | 6.6[3] | 8.1[3] | +23% |
| Compound 5 | (I) | 26.4 | 38.0 | +44% |
| Compound 24 | (VI) | 48.6 | 62.6 | +29% |
| Compound 7 | (I) | 10.9 | 114.5 | +950% |
| Compound 24 | (VI) | 48.6 | 21.9 | −55% |
| Compound 9 | (IV) | 8.7[2] | 5.3[2] | −39% |
| Compound 24 | (VI) | 48.6 | 79.0 | +63% |
| Compound 9 | (IV) | 8.7[2] | 9.8[2] | +23% |
| Compound 47 | (XIV) | 1.0[4] | 0.8[4] | −20%. |
| Compound 10 | (IV) | 6.6[3] | 4.1[3] | −38% |
| Compound 24 | (VI) | 48.6 | 69.3 | +43% |
| Compound 10 | (IV) | 6.6[3] | 7.2[3] | +9% |
| Compound 31 | (IX) | 29.4 | 35.3 | +20% |
| Compound 24 | (VI) | 48.6 | 35.4 | −27% |
| Compound 31 | (IX) | 29.4 | 387.1 | +1217% |
| Compound 24 | (VI) | 48.6 | 63.9 | +31% |
| Compound 47 | (XIV) | 1.0[4] | 0.8[4] | −20% |
| Compound 30 | (VIII) | 18.7 | 198.4 77.4[5] | +314% |
| Compound 31 | (IX) | 29.4 | 121.0[5] | +312% |

[1]the perfume compounds released from the different compounds are indicated in Example 1

[2]the release of 2-undecanone was followed

[3]the release of 4-(4-methoxyphenyl)butan-2-one was followed

[4] the release of (Z)-hex-3-en-1-al was followed

[5]both compounds release the same perfume compound (2-methylundecanal); the total measured value for the pro-perfume composition (198.4 ng/L) was thus (arbitrarily) attributed to the individual compounds in the same ratio corresponding to that measured for the individual compounds (ca. 39:61), therefore 0.39 × 198.4 ng/L = 77.4 ng/L and 0.61 × 198.4 ng/L = 121.0 ng/L The data in Table 2 show that pro-perfume compositions containing at least two structurally different pro-perfume compounds have a synergistic effect by releasing higher amounts of at least one of the perfume compounds. This effect can be considerable with an increase of up to more than 1000%. In most of the cases a positive effect was observed for both perfumes released from the two structurally different pro-perfumes in the composition. However, in some cases, a decrease of one of the perfume compounds was observed; in these cases the increase of perfume release from the other pro-perfume in the mixture was higher than that decrease, thus still resulting in an increased overall performance of the pro-perfume composition according to the invention. For example, in the composition of Compound 7 and Compound 24, a considerable decrease was observed in the amount of perfume compound released from Compound 24 (−55%), but an extraordinary increase in the amount of perfume compound released from Compound 7 (+950%). A similar effect was observed for the composition of Compound 24 (−27%) and Compound 31 (+1217%).

It is also quite noteworthy, that compositions comprising structurally different pro-perfumes (e.g. Compound 30 according to formula (VIII) and Compound 31 according to formula (IX)) releasing the same perfume compound by two different mechanisms generated considerably higher amounts of the corresponding perfume compound than one would have expected from the sum of the two individual compounds.

The data in Table 2 clearly demonstrate that a positive synergistic effect of perfume release is obtained from pro-perfume compositions containing at least two structurally different pro-perfume compounds according to the present invention, as compared to the amounts of perfume released from the individual pro-perfumes treated under the same conditions. This strong positive synergistic perfuming effect that can be obtained from pro-perfume compositions according to the present invention is quite surprising and unexpected from the teaching in the prior-art.

Comparative Example 2

Performance of Pro-Perfume Compositions According to the Present Invention in a Model Surface Cleaner Application

Combination of Structurally Equivalent Pro-Perfumes of the Same General Formula (I)

The present comparative experiment was carried out using the same conditions as described in Example 2 before for a composition of structurally equivalent pro-perfumes, both of formula (I), releasing different perfume compounds by the same release mechanism. The results are summarized in Table 3.

TABLE 3

Average headspace concentrations of perfume compounds released from an individual pro-perfume and from a composition of structurally equivalent pro-perfumes of the same general formula on a glass plate after drying for 1 day.

| Compositions | Example for a pro-perfume according to formula | Avg. headspace concentration [ng/L] of perfume compound)[(1)] released from the individual pro-perfume | Avg. headspace concentration [ng/L] of perfume compound)[(1)] released from the pro-perfume composition | Increase of release from the pro-perfume composition vs. the individual pro-perfume |
|---|---|---|---|---|
| Compound 1 | (I) | 5.8 | 3.9 | −33% |
| Compound 3 | (I) | 12.8 | 2.2 | −83% |

[(1)]the perfume compounds released from the different compounds are indicated in Example 1

The composition of structurally equivalent pro-perfumes, here both of the same general formula (I), released lower amounts of perfume compounds into the headspace than the respective individual pro-perfumes. No positive synergistic effect was observed in this case. It is thus advantageous to use compositions of structurally different types of pro-perfume compounds according to the invention.

Example 3

Performance of Pro-Perfume Compositions According to the Present Invention in an Enzyme-Containing Model Surface Cleaner Application

Combination of a Pro-Perfume of Formula (VIII) with a Pro-Perfume of Formula (XIII)

This Example was carried out as described before (Example 2) using an aqueous solution of SLES (10%) containing an alkaline lipase for detergents (DETE-2624, origin: Creative Enzymes, at 10 μg/mL) and by depositing 100 μL of the solution onto the glass plates. Table 4 summarizes the average headspace concentrations (mean values of the 6 data points) of perfume compounds released from the individual pro-perfumes and from the corresponding pro-perfume composition according to the present invention.

TABLE 4

Average headspace concentrations of perfume compounds released from Compound 45 and from Compound 45 in a composition with Compound 30 on a glass plate after drying for 1 day.

| Compositions | Example for a pro-perfume according to formula | Avg. headspace concentration of perfume compound [ng/L] released from the individual pro-perfume | Avg. headspace concentration of perfume compound [ng/L] released from the pro-perfume composition | Increase of release from the pro-perfume composition vs. the individual pro-perfume |
|---|---|---|---|---|
| Compound 30 | (VIII) | n.d. | n.d. | n.d. |
| Compound 45 | (XIII) | 22.9 | 26.9 | +17% |

n.d. = not determined

In the presence of enzymes, a pro-perfume composition according to the present invention containing at least one compound according to formula (XIII) released higher amounts of perfume compounds as the individual pro-perfume according to formula (XIII) in the absence of another pro-perfume.

Example 4

Performance of Pro-Perfume Compositions According to the Present Invention in a Fabric Softener Application

Combination of a Pro-Perfume of Formula (I) with a Pro-Perfume of Formula (IV)

Preparation of a liquid fabric softener: A liquid fabric softener was prepared by mixing a TEA-esterquat (methyl bis[ethyl(tallowate)]-2-hydroxyethyl ammonium methyl sulfate, Stepantex® VL 90A), 12.3 wt %, 10% aqueous calcium chloride, 0.4 wt %, 1,2-benzisothiazolin-3-one (Proxel® GXL), 0.04 wt % and deionized water, 87.2 wt %. The liquid fabric softener was prepared by placing the water and 1,2-benzisothiazolin-3-one in a reactor and heating the mixture under stirring to 65° C. Then methyl bis[ethyl (tallowate)]-2-hydroxyethyl ammonium methyl sulfate, heated at 65° C., was added. After stirring for 15 min, $CaCl_2$ was added, and the mixture was left cooling to room temperature.

Compounds 9 to 18, as pro-perfumes according to formula (IV), (11.3 mg each) were each weighed into a vial together with Compound 1, as pro-perfume according to formula (I), (11.3 mg), and dissolved in acetone (70 mg). The synthesis of the different pro-perfumes is described in Example 1. Liquid fabric softener (4.5 g) was added to the vial and the mixture shaken by hand to mix. Reference samples were prepared in the same manner using equivalent molar amounts of the perfumery ingredients expected to be released. Fabric softener samples containing individual Compounds 1 and 9 to 18 (11.3 mg) were prepared in the same manner.

Liquid Fabric Softener Application:

The fabric softener samples were rinsed with deionized water into a 3 L beaker and the beaker was filled to a total volume of 1.5 L. Three, 5 g cotton swatches (ca. 12.5×12.5 cm, weight 270 g/m$^2$; item 403 from Testfabrics, West Pittston, PA) were added to the beaker and agitated by hand for 3 min. After an additional 2 min of standing, the swatches were removed, and excess water squeezed out by hand. The swatches were hung to dry overnight (15-16 h) at room temperature. Two of the swatches then were subjected to dynamic headspace analysis.

Headspace Analysis from Fabric Softener Application:

Each analyzed swatch was placed inside a thermostated (30° C.) headspace sampling cell (about 160 mL volume). Using an air-sampling pump, a constant flow of air (200 mL/min) was drawn through the sampling cell and then through a poly(2,6-diphenyl-p-phenylene oxide (Tenax© TA, 100 mg) cartridge. Prior to entering the sample cell, the air was drawn through a plug of active charcoal and then through a saturated NaCl solution to maintain a constant relative humidity of 75%. Headspace samples were collected for 30 min. The cartridges were thermally desorbed with a Perkin Elmer TurboMatrix 650 thermal desorber coupled to an Agilent 6890 gas chromatograph equipped with an Agilent 5975C mass spectrometer and a Varian VF-1 ms capillary column (30 m, i.d. 0.25 mm, film 0.25 μm). The desorber parameters were: valve temperature 250° C., transfer line 250° C., purge time 1 min, desorption temperature 240° C., desorption time 5 min, desorption flow 20 mL/min, trap −30° C. to 250° C. at 40° C./sec, trap hold time 4 min, outlet split 48 mL/min, column flow 1 mL/min. The GO oven temperature profile was 52° C. (1 min) to 210° C. at 20° C./min then ramped to 250° C. (2 min). When analyzing for (Z)-hex-3-en-1-ol, the initial oven temperature was 40° C. (2 min). Peak areas obtained for the respective analytes (SIM mode) were measured and the average values are reported in Table 5.

TABLE 5

Dynamic headspace data (integrated peak areas) of perfumery raw materials obtained from line-dried cotton treated with fabric softener containing mixtures of a pro-perfume according to formula (IV) and a pro-perfume according to formula (1) (HaloScent ® D) (pro-perfume mixture), the respective unmodified perfumery raw materials (reference mixture), a pro-perfume according to formula (IV) alone and HaloScent ® D alone (average often measurements).

| | Perfumery raw materials released | | |
|---|---|---|---|
| | 2-undecanone | 2-phenylethyl formate | delta-damascene |
| Compound 1 and Compound 9 | $3.42 \times 10^6$ | $3.19 \times 10^6$ | $3.39 \times 10^6$ |
| reference mixture | $1.70 \times 10^5$ | $8.08 \times 10^4$ | $6.80 \times 10^4$ |
| factor increase over reference | 20.1 | 39.4 | 49.8 |
| Compound 9 | $3.85 \times 10^6$ | $3.42 \times 10^6$ | — |
| Compound 1 | — | — | $1.99 \times 10^6$ |
| | 4-(4-methoxyphenyl) butan-2-one | 2-phenylethyl formate | delta-damascene |
| Compound 1 and Compound 10 | $2.12 \times 10^6$ | $2.24 \times 10^6$ | $3.63 \times 10^6$ |
| reference mixture | $7.91 \times 10^4$ | $5.50 \times 10^4$ | $1.38 \times 10^4$ |
| factor increase over reference | 26.8 | 40.7 | 263 |
| Compound 10 | $1.89 \times 10^6$ | $2.35 \times 10^6$ | — |
| Compound 1 | — | — | $1.99 \times 10^6$ |
| | 4-phenylbutan-2-one | 2-phenylethyl formate | delta-damascene |
| Compound 1 and Compound 11 | $1.09 \times 10^6$ | $1.93 \times 10^6$ | $2.62 \times 10^6$ |
| reference mixture | $3.83 \times 10^4$ | $6.54 \times 10^4$ | $8.04 \times 10^4$ |
| factor increase over reference | 28.5 | 29.5 | 32.5 |
| Compound 11 | $1.75 \times 10^6$ | $2.86 \times 10^6$ | — |
| Compound 1 | — | — | $1.99 \times 10^6$ |
| | 2-undecanone | hex-3-en-1-yl formate | delta-damascene |
| Compound 1 with Compound 12 | $9.05 \times 10^6$ | $6.56 \times 10^5$ | $3.65 \times 10^6$ |
| reference mixture | $2.54 \times 10^5$ | $5.52 \times 10^4$ | $1.47 \times 10^5$ |
| factor increase over reference | 35.6 | 119 | 24.8 |
| Compound 12 | $2.91 \times 10^6$ | $4.27 \times 10^5$ | — |
| Compound 1 | — | — | $1.99 \times 10^6$ |

TABLE 5-continued

Dynamic headspace data (integrated peak areas) of perfumery raw materials obtained from line-dried cotton treated with fabric softener containing mixtures of a pro-perfume according to formula (IV) and a pro-perfume according to formula (1) (HaloScent ® D) (pro-perfume mixture), the respective unmodified perfumery raw materials (reference mixture), a pro-perfume according to formula (IV) alone and HaloScent ® D alone (average often measurements).

| | 2-undecanone | 2-phenoxyethyl formate | delta-damascene |
|---|---|---|---|
| Compound 1 and Compound 13 | $3.83 \times 10^6$ | $2.36 \times 10^6$ | $3.06 \times 10^6$ |
| reference mixture | $1.26 \times 10^5$ | $3.99 \times 10^4$ | $5.75 \times 10^4$ |
| factor increase over reference | 30.4 | 59.1 | 53.2 |
| Compound 13 | $1.26 \times 10^6$ | $2.09 \times 10^6$ | — |
| Compound 1 | — | — | $1.99 \times 10^6$ |

| | 2-undecanone | 3-octyl formate | delta-damascene |
|---|---|---|---|
| Compound 1 and Compound 14 | $2.73 \times 10^6$ | $5.53 \times 10^6$ | $1.71 \times 10^6$ |
| reference mixture | $8.83 \times 10^4$ | $3.25 \times 10^4$ | $4.45 \times 10^4$ |
| factor increase over reference | 30.9 | 170 | 38.4 |
| Compound 14 | $3.64 \times 10^6$ | $7.72 \times 10^5$ | — |
| Compound 1 | — | — | $1.99 \times 10^6$ |

| | 1-(4-methoxyphenyl)ethan-1-one | 2-phenylethyl formate | delta-damascene |
|---|---|---|---|
| Compound 1 and Compound 15 | $2.23 \times 10^6$ | $1.63 \times 10^6$ | $2.77 \times 10^6$ |
| reference mixture | $2.01 \times 10^5$ | $3.92 \times 10^4$ | $4.50 \times 10^4$ |
| factor increase over reference | 11.0 | 41.5 | 61.5 |
| Compound 15 | $1.42 \times 10^6$ | $1.04 \times 10^6$ | — |
| Compound 1 | — | — | $1.99 \times 10^6$ |

| | 1-(p-tolyl)ethan-1-one | 2-phenylethyl formate | delta-damascene |
|---|---|---|---|
| Compound 1 and Compound 16 | $2.30 \times 10^6$ | $2.17 \times 10^6$ | $2.75 \times 10^6$ |
| reference mixture | $7.58 \times 10^4$ | $5.62 \times 10^4$ | $7.50 \times 10^4$ |
| factor increase over reference | 30.3 | 38.6 | 36.6 |
| Compound 16 | $2.62 \times 10^6$ | $2.52 \times 10^6$ | — |
| Compound 1 | — | — | $1.99 \times 10^6$ |

| | 1-(naphthalen-2-yl)ethan-1-one | 2-phenylethyl formate | delta-damascene |
|---|---|---|---|
| Compound 1 and Compound 17 | $1.01 \times 10^6$ | $1.89 \times 10^6$ | $4.55 \times 10^6$ |
| reference mixture | $3.85 \times 10^5$ | $3.28 \times 10^4$ | $7.41 \times 10^4$ |
| factor increase over reference | 2.6 | 57.6 | 61.4 |
| Compound 17 | $1.34 \times 10^6$ | $3.31 \times 10^6$ | — |
| Compound 1 | — | — | $1.99 \times 10^6$ |

| | eugenol | methyl benzoate | delta-damascene |
|---|---|---|---|
| Compound 1 and Compound 18 | $1.49 \times 10^6$ | $1.50 \times 10^6$ | $2.31 \times 10^6$ |
| reference mixture | $1.31 \times 10^5$ | $1.11 \times 10^4$ | $3.58 \times 10^4$ |
| factor increase over reference | 11.3 | 135 | 64.5 |
| Compound 18 | $9.23 \times 10^5$ | $8.04 \times 10^5$ | — |
| Compound 1 | — | — | $1.99 \times 10^6$ |

The data shown in Table 5 demonstrate that higher amounts of individual perfumery raw materials could be detected upon release from perfuming compositions comprising two pro-perfumes after a fabric softener application compared to a reference mixture comprising the individual perfumery raw materials. This demonstrates the advantageous slow-release effect of pro-perfumes compared to individual volatile perfumery raw materials.

Moreover, the data demonstrate that higher amounts of at least one perfumery raw material could be detected upon release from the mixture of pro-perfumes compared to use of the respective pro-perfumes alone (i.e. not in combination). In many cases, even higher amounts for all perfumery raw materials could be detected upon release from the mixture of pro-perfumes compared to use of the respective pro-perfumes alone (e.g. Compounds 12, 13, 15, and 18).

Hence, the data show not only that the use of pro-perfumes is more effective compared to the use of individual perfumery raw materials, but also that the combination of pro-perfumes is more effective compared to the use of single pro-perfumes (not in combination with other pro-perfumes).

Example 5

Performance of Pro-Perfume Compositions According to the Present Invention in a Fabric Softener Application Combination of a Pro-Perfume of Formula (I) or a Pro-Perfume of Formula (IV) with a Pro-Perfume of Formula (XIII)

Headspace Analysis from Fabric Softener Application: A lipase-containing, liquid laundry detergent was prepared by mixing 1 g of lipase (Addclean LP L, Enzyme Innovation, Chino, CA) into 99 g of Tide Free and Gentle. Ten grams (10 g) of the lipase-containing detergent was diluted into 1 L of deionized water in a large beaker. Twelve, 5-g cotton swatches (ca. 12.5×12.5 cm, weight 270 g/m2, item 403 from Testfabrics, West Pittston, PA) were added to the beaker and agitated by hand for a few minutes and then allowed to soak in the detergent solution for a total of 15 min. The swatches were removed together and excess liquid squeezed out by hand. In a second beaker, the swatches were placed in 1 L of deionized water, separated by hand and allowed to soak for 2 min. The swatches then were removed individually and the excess liquid squeezed out by hand.

Four, fabric softener samples were prepared as described above containing Compound 45 (11.3 mg), as a pro-perfume according to formula (XIII) and another pro-perfume (11.3 mg) according to formula (I) (Compound 1) or according to formula (IV) (Compound 9), each pro-perfume individually (11.3 mg) and a reference sample containing equivalent molar amounts of the perfumery ingredients expected to be released. Each fabric softener sample was rinsed with deionized water into a 3 L beaker and the beaker was filled to a total volume of 1.5 L. Three of the wet, prewashed, 5-g cotton swatches were added to the beaker and agitated by hand for 3 min. After an additional 2 min of standing, the swatches were removed and excess water squeezed out by hand. The swatches were hung to dry overnight (15-16 h) at room temperature. The swatches then were subjected to dynamic headspace analysis as described above. Peak areas obtained for the respective analytes (SIM mode) were measured and the average values reported in Table 6.

TABLE 6

Dynamic headspace data (integrated peak areas) of perfumery raw materials obtained from line-dried cotton treated with a lipase-containing detergent followed by a fabric softener containing mixtures of Compound 45 and another pro-perfume according to the invention (pro-perfume mixture), the respective unmodified perfumery raw materials (reference mixture), Compound 45 and the other pro-perfume alone.

| | GC peak areas of perfumery raw materials | | |
|---|---|---|---|
| | 2-undecanone | 2-phenylethyl formate | geraniol |
| Compound 9 and Compound 45 | $1.27 \times 10^7$ | $4.40 \times 10^7$ | $2.31 \times 10^6$ |
| reference mixture | $1.15 \times 10^5$ | $2.82 \times 10^5$ | $1.50 \times 10^5$ |
| factor increase over reference | 110 | 156 | 15.4 |
| Compound 9 | $8.48 \times 10^6$ | $2.72 \times 10^7$ | — |
| Compound 45 | — | — | $1.63 \times 10^6$ |
| | delta-damascone | — | geraniol |
| Compound 1 and Compound 45 | $2.59 \times 10^6$ | — | $1.06 \times 10^6$ |
| reference mixture | $6.40 \times 10^4$ | — | $1.90 \times 10^5$ |
| factor increase over reference | 40.5 | — | 5.6 |
| Compound 1 | $1.06 \times 10^6$ | — | — |
| Compound 45 | — | — | $1.46 \times 10^6$ |

The headspace data show the pro-perfume mixtures released higher levels of perfumery volatiles compared to the respective reference samples demonstrating the desired slow-release effect of the pro-perfume molecules when used as a mixture.

Example 6

Performance of Pro-Perfume Compositions According to the Present Invention in a Fabric Softener Application Combination of a Pro-Perfume of Formula (IV) with a Pro-Perfume of Formula (X)

Headspace Analysis from Fabric Softener Application:

The pro-perfumes to be compared (either individually or as a mixture) were added to a liquid fabric softener formulation composed as described in Example 4 in order to release a total of 0.5 weight-% of the perfume.

Compound 9 (29.0 mg), as a pro-perfume according to formula (IV), and Compound 32 (31.9 mg), as a pro-perfume according to formula (X), were added to the fabric softener formulation (3.0 g) and stirred with a magnetic stirrbar.

In a flask, the fabric softener formulation with the pro-perfumes (70 mg) was diluted with demineralized cold tap water (23 g). The sample was vigorously shaken (10×). Then one cotton sheet (EMPA cotton test cloth Nr. 221, origin: Eidgenössische Materialprüfanstalt), pre-washed with an unperfumed detergent powder and cut to ca. 15×15 cm sheets, ca. 5.1 g) was added and agitated manually for 3 min, left standing for 2 min, then wrung out by hand, and weighed (ca. 10.0 g) to obtain a constant quantity of residual water. The cotton sheets were line-dried for 1 day before being analyzed.

Reference samples were prepared in the same manner, using equivalent amounts of the perfumery raw materials expected to be released.

For the measurements, the sheets were put into a headspace sampling cell (ca. 165 mL inner volume), which was placed in a xenon lamp (CO.FO.ME.GRA Solarbox 1500). The headspace cell was thermostatted at 25° C. and exposed to a constant air flow of ca. 200 mL/min. The air was filtered through active charcoal and aspirated through a saturated solution of NaCl (to ensure a constant humidity of the air of ca. 75%). The system was equilibrated during 10 min while adsorbing the volatiles on a waste Tenax® cartridge (filled with 100 mg of Tenax© TA adsorbent resin), then 5 min on a clean Tenax© cartridge (first data point). Then the xenon lamp was switched on to provide 3.1 mW/cm2 of UVA light (ca. 45000 lux) to the cotton surface, and the volatiles were adsorbed for 5 min onto a waste Tenax®, then 5× for 5 min onto clean Tenax® cartridges (data points 2-6). Then the volatiles were adsorbed onto a waste Tenax® cartridge for 5 min and onto a clean Tenax® cartridge for 5 min (3×, data points 7-9). Finally the volatiles were adsorbed onto a waste Tenax© cartridge for 25 min and onto a clean Tenax© cartridge for 5 min (data point 10). Waste Tenax® cartridges were discarded; clean Tenax© cartridges were desorbed on a Perkin Elmer TurboMatrix ATD thermodesorber connected to an Agilent Technologies 7890A GC System equipped with a FID. The volatiles were eluted with He on a HP-5 capillary column (30 m×0.32 μm, film 0.25 μm) using a temperature gradient from 60° C. to 200° C. at 15° C./min. Headspace concentrations (in ng/L) were obtained by external standard calibration, by injecting solutions of known amounts of volatiles onto clean Tenax® cartridges and desorbing them as described before. All data are average values of at least two measurements. Headspace concentrations obtained after sampling for 75 min ($9^{th}$ datapoint) are summarized in Table 7.

TABLE 7

Dynamic headspace data concentrations of perfumery raw materials obtained from line-dried cotton treated with a fabric softener containing mixtures of a pro-perfume of formula (IV) and a pro-perfume of formula (X), the respective unmodified perfumery raw materials (reference), the pro-perfume of formula (IV) alone and the pro-perfume of formula (X) alone.

| | Dynamic headspace concentrations of perfumery raw materials in ng/L | | |
|---|---|---|---|
| | 2-undecanone | 2-phenylethyl formate | 2-phenyl-acetaldehyde |
| Compound 9 and Compound 32 | 128 | 134 | 210 |
| reference | ca. 1 | 16 | 4 |
| factor increase over reference | 128 | 8 | 53 |
| Compound 9 | 113 | 127 | — |
| Compound 32 | — | — | 178 |

The headspace data show the pro-perfume mixtures released higher levels of perfumery volatiles compared to the respective reference samples demonstrating the desired slow-release effect of the pro-perfume molecules when used as a mixture.

Moreover, the data demonstrate that higher amounts of perfumery raw materials could be detected upon release from the mixture of pro-perfumes compared to use of the respective pro-perfumes alone (i.e. not in combination). Using a mixture of pro-perfumes is thus advantageous over using the individual pro-perfumes.

Example 7

Preparation of a Perfuming Composition (Perfume Oil)

A non-limiting example of a typical perfume oil is prepared by admixing the following ingredients:

| Ingredients | weight-% |
|---|---|
| Ethyl 2-methylbutanoate | 0.16 |
| Dipropylene glycol | 5.39 |
| Hexyl acetate | 0.37 |
| Limonene | 1.67 |
| 2,6-Dimethyl-7-octen-2-ol | 0.94 |
| 2-Phenylethanol | 2.15 |
| 3,7-Dimethyl-1,6-octadien-3-ol | 0.73 |
| (2RS,4SR/4RS)-4-Methyl-2-(2-methyl-1-propen-1-yl)tetrahydro-2H-pyran | 0.30 |
| Ethyl 2-methyl-1,3-dioxolane-2-acetate | 0.32 |
| Benzyl acetate | 2.46 |
| Allyl heptanoate | 0.38 |
| alpha-Terpineol | 0.88 |
| 3,7-Dimethyl-6-octen-1-ol | 0.55 |
| 4-Methoxybenzaldehyde | 1.00 |
| (E)-4-Methyl-3-decen-5-ol | 0.37 |

-continued

| Ingredients | weight-% |
|---|---|
| [cis/trans-4-(2-Propanyl)cyclohexyl]methanol | 0.47 |
| 1-Methoxy-4-[(1E)-1-propen-1-yl]benzene | 0.15 |
| (1RS,2RS/2SR)-2-(2-Methyl-2-propanyl) cyclohexyl acetate | 1.95 |
| 1,1-Dimethyl-2-phenylethyl acetate | 0.95 |
| Tricyclo[5.2.1,0$^{2,}$~]dec-3/4-en-8-yl acetate | 3.34 |
| Allyl 3-cyclohexylpropanoate | 0.26 |
| 3-(4-Isopropylphenyl)-2-methylpropanal | 8.18 |
| (3E)-3-Methyl-4-(2,6,6-trimethyl-2-cyclohexen-1-yl)-3-buten-2-one and (1E)-1-(2,6,6-trimethyl-2-cyclohexen-1-yl)-1-penten-3-one | 1.13 |
| 2-Phenoxyethyl 2-methylpropanoate | 5.38 |
| Tricyclo[5.2.1.0(2,6)]dec-3/4-en-8-yl propanoate | 2.32 |
| 5-Heptyldihydro-2(3H)-furanone | 2.30 |
| 2/3-Methylbutyl salicylate | 1.42 |
| (3Z)-3-Hexen-1-yl salicylate | 0.31 |
| 1-(2,3,8,8-Tetramethyl-1,3,4,5,6,7-hexahydronaphthalen-2-yl)ethanone | 16.03 |
| Hexyl 2-hydroxybenzoate | 5.04 |
| (2E)-2-Benzylideneoctanal | 21.22 |
| (−)-(3aR,5aS,9aS,9bR)-3a,6,6,9a-Tetramethyldodecahydronaphtho[2,1-b]furan | 0.27 |
| 1-Oxa-12/13-cyclohexadecen-2-one | 4.78 |
| Oxacyclohexadecan-2-one | 3.82 |
| Benzyl 2-hydroxybenzoate | 3.01 |
| | Total: 100 |

Example 8

Preparation of Liquid Fabric Softener Formulations Comprising a Pro-Perfume Composition According to the Present Invention Typical liquid fabric softener formulations comprising at least two of the invention's pro-perfumes as listed in Table 8 are prepared similarly to those described in Example 4. A typical perfumery composition used as a perfume oil is described in Example 7.

TABLE 8

Liquid fabric softener formulations A-I comprising the invention's pro-perfume compositions, (values are in weight-%).

| Ingredients | A | B | C | D | E | F | G | H | I |
|---|---|---|---|---|---|---|---|---|---|
| Cationic surfactant (TEA-Esterquat) [(1)] | 12.1 | 12.1 | 12.1 | 12.1 | 16.2 | 16.2 | 16.2 | 16.2 | 16.2 |
| Calcium chloride (10% aq.) | 0.4 | 0.4 | 0.4 | 0.4 | 0.6 | 0.6 | 0.6 | 0.6 | 0.6 |
| 1,2-Benzisothiazolin-3-one [(2)] | 0.04 | 0.04 | 0.04 | 0.04 | — | — | — | — | — |
| Perfume oil | 1.8 | 1.9 | 1.8 | 1.6 | 0.8 | 0.6 | 1.0 | 1.8 | 1.4 |
| Pro-perfume Compound 1 | 0.05 | 0.05 | | | | | | | |
| Pro-perfume Compound 2 [(3)] | 0.05 | | | 0.1 | | | | | 0.05 |
| Pro-perfume Compound 4 | | | | | | | | | 0.05 |
| Pro-perfume Compound 5 | | | 0.1 | | | | | | |
| Pro-perfume Compound 8 | | | | | 0.2 | | | | |
| Pro-perfume Compound 10 | | | | | 0.15 | | | | |
| Pro-perfume Compound 20 | | | | | | 0.1 | | | |
| Pro-perfume Compound 25 | | | | | | | 0.3 | | |
| Pro-perfume Compound 27 | | | | | | 0.25 | | | |
| Pro-perfume Compound 29 | 0.1 | | 0.1 | | 0.05 | | 0.2 | | |
| Pro-perfume Compound 30 | | | | | | 0.1 | | 0.1 | 0.1 |
| Pro-perfume Compound 31 | | 0.05 | | | | 0.05 | | 0.1 | |
| Pro-perfume Compound 32 | | | | 0.2 | | | | | |
| Pro-perfume Compound 38 | | | | 0.1 | | | | | |
| Deionized water | | | | | complete to 100 | | | | |

(1) e.g. Stepantex ® VL 90A; origin: Stepan (2) Proxel ® GXL; origin: Arch (3) mixture of Compounds 2a/2b ca. 45:55

Example 9

Preparation of Liquid Detergent Formulations Comprising a Pro-Perfume Composition According to the Present Invention Typical liquid detergent formulations comprising at least two of the invention's pro-perfumes are listed in Table 9. The perfume oil and the pro-perfumes are added under gentle shaking to the unperfumed aqueous liquid detergent formulation.

TABLE 9

Liquid detergent formulations A-I comprising the invention's pro-perfume compositions, (values are in weight-%).

| Ingredients | A | B | C | D | E | F | G | H | I |
|---|---|---|---|---|---|---|---|---|---|
| Sodium $C_{14-17}$ Alkyl Sec Sulfonate [1] | 6.9 | 6.9 | 6.9 | 6.9 | 6.9 | 6.9 | 6.9 | 6.9 | 6.9 |
| Fatty acids, $C_{12-18}$ and $C_{18-}$ unsaturated [2] | 7.4 | 7.4 | 7.4 | 7.4 | 7.4 | 7.4 | 7.4 | 7.4 | 7.4 |
| $C_{12/14}$ fatty alcohol polyglycol ether with 7 mol EO [3] | 16.8 | 16.8 | 16.8 | 16.8 | 16.8 | 16.8 | 16.8 | 16.8 | 16.8 |
| Triethanolamine | 7.4 | 7.4 | 7.4 | 7.4 | 7.4 | 7.4 | 7.4 | 7.4 | 7.4 |
| Propylene glycol | 10.9 | 10.9 | 10.9 | 10.9 | 10.9 | 10.9 | 10.9 | 10.9 | 10.9 |
| Citric acid | 6.4 | 6.4 | 6.4 | 6.4 | 6.4 | 6.4 | 6.4 | 6.4 | 6.4 |
| Potassium hydroxide | 9.4 | 9.4 | 9.4 | 9.4 | 9.4 | 9.4 | 9.4 | 9.4 | 9.4 |
| Protease | 0.2 | 0.2 | 0.2 | 0.2 | 0.2 | 0.2 | 0.2 | 0.2 | 0.2 |
| Amylase | 0.2 | 0.2 | 0.2 | 0.2 | 0.2 | 0.2 | 0.2 | 0.2 | 0.2 |
| Mannanase | 0.2 | 0.2 | 0.2 | 0.2 | 0.2 | 0.2 | 0.2 | 0.2 | 0.2 |
| Acrylates/Steareth-20 methacrylate structuring crosspolymer [4] | 5.9 | 5.9 | 5.9 | 5.9 | 5.9 | 5.9 | 5.9 | 5.9 | 5.9 |
| Perfume oil | 0.5 | 0.7 | 0.4 | 0.7 | 0.7 | 0.8 | 0.8 | 0.6 | 0.7 |
| Pro-perfume Compound 1 | 0.2 | | | | | | 0.1 | | |
| Pro-perfume Compound 4 | | | | | | 0.05 | | | |
| Pro-perfume Compound 7 | | 0.1 | | | | | 0.08 | | |
| Pro-perfume Compound 8 | | | 0.25 | | | | | 0.25 | 0.1 |
| Pro-perfume Compound 11 | 0.2 | | | | | | | 0.15 | |
| Pro-perfume Compound 19 | | 0.15 | | | | | | | |
| Pro-perfume Compound 22 | | | | 0.1 | | | | | |
| Pro-perfume Compound 24 | | | | | | | 0.02 | | |
| Pro-perfume Compound 28 | | | | | 0.2 | | | | |
| Pro-perfume Compound 29 | | | | | 0.1 | 1.5 | | | 0.1 |
| Pro-perfume Compound 35 | | | 0.15 | | | | | | |
| Pro-perfume Compound 38 | | 0.1 | | | | | | | |
| Pro-perfume Compound 45 | 0.1 | | | 0.2 | | | | | 0.1 |
| Deionized water | | | | complete to 100 | | | | | |

[1] Hostapur ® SAS 60; origin: Clariant
[2] Edenor ® K 12-18; origin: Cognis
[3] Genapol ® LA 070; origin: Clariant
[4] Aculyn ® 88; origin: Dow Chemicals

Example 10

Preparation of all-Purpose Cleaner Formulations Comprising a Pro-Perfume Composition According to the Present Invention Typical all-purpose cleaner formulations comprising at least two of the invention's pro-perfumes are listed in Table 10. The perfume oil and the pro-perfumes are added under gentle shaking to the unperfumed aqueous all-purpose cleaner formulation.

TABLE 10

All-purpose cleaner formulations A-I comprising the invention's pro-perfume compositions, (values are in weight-%).

| Ingredients | A | B | C | D | E | F | G | H | I |
|---|---|---|---|---|---|---|---|---|---|
| Ethoxylated alcohol ($C_9$-$C_{11}$, 8 EO) [1] | 19.8 | 19.8 | 19.8 | 19.8 | 19.8 | 19.8 | 19.8 | 19.8 | 19.8 |
| Sodium dodecyl benzene sulfonate [2] | 15.8 | 15.8 | 15.8 | 15.8 | 15.8 | 15.8 | 15.8 | 15.8 | 15.8 |
| Sodiumcumene sulfonate [3] | 7.9 | 7.9 | 7.9 | 7.9 | 7.9 | 7.9 | 7.9 | 7.9 | 7.9 |
| Methyl chloro isothiazolinone/methyl isothiazolinone 3.3:1 [4] | 0.8 | 0.8 | 0.8 | 0.8 | 0.8 | 0.8 | 0.8 | 0.8 | 0.8 |

TABLE 10-continued

All-purpose cleaner formulations A-I comprising the invention's pro-perfume compositions, (values are in weight-%).

| Ingredients | A | B | C | D | E | F | G | H | I |
|---|---|---|---|---|---|---|---|---|---|
| Perfume oil | 0.7 | 0.5 | 0.8 | 0.8 | 0.8 | 0.4 | 0.5 | 0.8 | 0.7 |
| Pro-perfume Compound 1 | 0.15 | | | | | | | 0.1 | |
| Pro-perfume Compound 2(5) | | 0.1 | | 0.15 | | | | | |
| Pro-perfume Compound 5 | | | | | | 0.15 | 0.05 | | |
| Pro-perfume Compound 10 | | | | | 0.15 | | | | 0.1 |
| Pro-perfume Compound 16 | | | | | | | 0.1 | | |
| Pro-perfume Compound 20 | | | 0.05 | | | | | | 0.1 |
| Pro-perfume Compound 24 | | 0.2 | | | | 0.1 | | | |
| Pro-perfume Compound 29 | 0.15 | | 0.05 | | | | | | |
| Pro-perfume Compound 31 | | | 0.1 | | | | 0.15 | 0.1 | |
| Pro-perfume Compound 37 | | | | | | 0.15 | | | |
| Pro-perfume Compound 38 | | | | 0.05 | | | | | |
| Pro-perfume Compound 47 | | | | | | | | | 0.1 |
| Pro-perfume Compound 49 | | | | | 0.05 | | | | |
| Deionized water | | | | | complete to 100 | | | | |

(1) Neodol ® 91-8; origin: Shell Chemicals
(2) Biosoft ® D-40; origin: Stepan
(3) Stepanate ® SCS; origin: Stepan
(4) Kathon ® CG; origin: Dow Chemicals
(5) mixture of Compounds 2a/2b ca. 45:55

Example 11

Preparation of Transparent Isotropic Shampoos Comprising a Pro-Perfume Composition According to the Present Invention Typical shampoo formulations comprising at least two of the invention's pro-perfumes are listed in Table 11. They are prepared by dispersing Polyquaternium-10 in water. The remaining ingredients of Phase A are mixed separately by addition of one after the other while mixing well after each adjunction. This pre-mix is added to the Polyquaternium-0 dispersion and mixed for another 5 m. Then, the premixed Phase B and the premixed Phase C are added (Monomuls® 90L-12 was heated to melt in Texapon® NSO IS) while agitating. Phase 0 and Phase E are added while agitating. The pH is adjusted with citric acid solution to 5.5-6.0 leading to an unperfumed transparent isotropic shampoo formula.

TABLE 11

Transparent isotropic shampoo formulations A-H comprising the invention's pro-perfume compositions, (values are in weight-%).

| Phase | Ingredients | A | B | C | D | E | F | G | H |
|---|---|---|---|---|---|---|---|---|---|
| A | Deionized water | 43.4 | 43.4 | 43.4 | 43.4 | 43.4 | 43.4 | 43.4 | 43.4 |
| | Polyquaternium-10 (1) | 0.3 | 0.3 | 0.3 | 0.3 | 0.3 | 0.3 | 0.3 | 0.3 |
| | Glycerin 85% (2) | 1.0 | 1.0 | 1.0 | 1.0 | 1.0 | 1.0 | 1.0 | 1.0 |
| | DMDM Hydantoin (3) | 0.2 | 0.2 | 0.2 | 0.2 | 0.2 | 0.2 | 0.2 | 0.2 |
| B | Sodium laureth sulfate (4) | 27.3 | 27.3 | 27.3 | 27.3 | 27.3 | 27.3 | 27.3 | 27.3 |
| | Cocamidopropyl betaine (5) | 3.1 | 3.1 | 3.1 | 3.1 | 3.1 | 3.1 | 3.1 | 3.1 |
| | Disodium cocoamphodiacetate (6) | 3.9 | 3.9 | 3.9 | 3.9 | 3.9 | 3.9 | 3.9 | 3.9 |
| | Ethoxy (20) stearyl alcohol (7) | 1.0 | 1.0 | 1.0 | 1.0 | 1.0 | 1.0 | 1.0 | 1.0 |
| C | Sodium laureth sulfate (4) | 3.1 | 3.1 | 3.1 | 3.1 | 3.1 | 3.1 | 3.1 | 3.1 |
| | Glyceryl laureate (8) | 0.2 | 0.2 | 0.2 | 0.2 | 0.2 | 0.2 | 0.2 | 0.2 |
| D | Deionized water | 1.0 | 1.0 | 1.0 | 1.0 | 1.0 | 1.0 | 1.0 | 1.0 |
| | Sodium methylparaben (9) | 0.1 | 0.1 | 0.1 | 0.1 | 0.1 | 0.1 | 0.1 | 0.1 |
| E | Sodium chloride (10% aqueous solution) | 14.6 | 14.6 | 14.6 | 14.6 | 14.6 | 14.6 | 14.6 | 14.6 |
| | Citric acid (10% aqueous solution till pH 5.5-6.0) | q.s. | q.s. | q.s. | q.s. | q.s. | q.s. | q.s. | q.s. |
| F | Perfume oil | 0.5 | 0.8 | 0.2 | 0.6 | 0.6 | 0.7 | 0.7 | 0.5 |
| | Pro-perfume Compound 3 | 0.15 | | | | | 0.1 | | 0.15 |
| | Pro-perfume Compound 4 | | 0.05 | | | | | 0.05 | |
| | Pro-perfume Compound 9 | 0.1 | | | | | | 0.05 | |
| | Pro-perfume Compound 20 | | | | 0.15 | | | | 0.1 |
| | Pro-perfume Compound 22 | | | 0.2 | | | 0.1 | | |
| | Pro-perfume Compound 26 | | | 0.3 | 0.15 | 0.1 | | | |

TABLE 11-continued

| Transparent isotropic shampoo formulations A-H comprising the invention's pro-perfume compositions, (values are in weight-%). | | | | | | | | | |
|---|---|---|---|---|---|---|---|---|---|
| Phase | Ingredients | A | B | C | D | E | F | G | H |
| | Pro-perfume Compound 29 | 0.15 | 0.05 | | | 0.2 | | | |
| | Pro-perfume Compound 40 | | | 0.2 | | | | 0.1 | 0.15 |

(1) Ucare ® Polymer JR-400; origin: Noveon
(2) Origin: Brenntag Schweizerhall AG
(3) Glydant ®; origin: Lonza
(4) Texapon ® NSO IS; origin: Cognis
(5) Tego ® Betain F 50; origin: Evonik
(6) Amphotensid GB 2009; origin: Zschimmer & Schwarz
(7) Brij ® S20; origin: Croda
(8) Monomuls ® 90 L-12; origin: Gruenau GmbH
(9) Nipagin Monosodium; origin: NIPA The perfumed shampoo is obtained by adding under gentle shaking a perfume oil and at least two of the pro-perfume compounds according to the present invention (Phase F) into the unperfumed shampoo formulation (Phases A-E).

Example 12

Preparation of Pearly Shampoos Comprising a Pro-Perfume Composition According to the Present Invention Typical pearly shampoo formulations comprising at least two of the invention's pro-perfumes are listed in Table 12.

They are prepared by dispersing Tetrasodium EDTA, Guar Hydroxypropyltrimonium chloride and Polyquaternium-10 in water. NaOH (10% aqueous solution, Phase B) is added once Phase A was homogeneous. Then, the premixed Phase C is added, and the mixture heated to 75° C. Phase D ingredients are added and mixed until the mixture was homogeneous. The mixture is cooled. At 45° C., Phase E ingredients are added while mixing. The final viscosity is adjusted with NaCl (25% aqueous solution) and a pH of 5.5-6.0 is adjusted with NaOH (10% aqueous solution).

TABLE 12

| Pearly shampoo formulations A-H comprising the invention's pro-perfume compositions, (values are in weight-%). | | | | | | | | | |
|---|---|---|---|---|---|---|---|---|---|
| Phase | Ingredients | A | B | C | D | E | F | G | H |
| A | Deionized water | 45.52 | 45.52 | 45.52 | 45.52 | 45.52 | 45.52 | 45.52 | 45.52 |
| | Tetrasodium EDTA (1) | 0.05 | 0.05 | 0.05 | 0.05 | 0.05 | 0.05 | 0.05 | 0.05 |
| | Guar hydroxypropyl-trimonium chloride (2) | 0.05 | 0.05 | 0.05 | 0.05 | 0.05 | 0.05 | 0.05 | 0.05 |
| | Polyquaternium-10 (3) | 0.07 | 0.07 | 0.07 | 0.07 | 0.07 | 0.07 | 0.07 | 0.07 |
| B | NaOH (10% aqueous solution) | 0.3 | 0.3 | 0.3 | 0.3 | 0.3 | 0.3 | 0.3 | 0.3 |
| C | Ammonium lauryl sulfate (4) | 33.7 | 33.7 | 33.7 | 33.7 | 33.7 | 33.7 | 33.7 | 33.7 |
| | Ammonium laureth sulfate (5) | 9.16 | 9.16 | 9.16 | 9.16 | 9.16 | 9.16 | 9.16 | 9.16 |
| | Cocamidopropyl betaine (6) | 2.0 | 2.0 | 2.0 | 2.0 | 2.0 | 2.0 | 2.0 | 2.0 |
| | Dimethicone (&) C12-13 Pareth-4 (&) $C_{12-13}$ pareth-23 (&) salicylic acid (7) | 2.5 | 2.5 | 2.5 | 2.5 | 2.5 | 2.5 | 2.5 | 2.5 |
| D | Cetyl alcohol (8) | 1.2 | 1.2 | 1.2 | 1.2 | 1.2 | 1.2 | 1.2 | 1.2 |
| | Cocamide MEA (9) | 1.5 | 1.5 | 1.5 | 1.5 | 1.5 | 1.5 | 1.5 | 1.5 |
| | Glycol distearate (10) | 2.0 | 2.0 | 2.0 | 2.0 | 2.0 | 2.0 | 2.0 | 2.0 |
| E | Methylchloroisothiazolinone & methylisothiazolinone (11) | 0.1 | 0.1 | 0.1 | 0.1 | 0.1 | 0.1 | 0.1 | 0.1 |
| | D-Panthenol 75% (12) | 0.1 | 0.1 | 0.1 | 0.1 | 0.1 | 0.1 | 0.1 | 0.1 |
| | Deionized water | 0.3 | 0.3 | 0.3 | 0.3 | 0.3 | 0.3 | 0.3 | 0.3 |
| F | Sodium chloride (25% aqueous solution) | 0.6 | 0.6 | 0.6 | 0.6 | 0.6 | 0.6 | 0.6 | 0.6 |
| G | Perfume oil | 0.6 | 0.7 | 0.55 | 0.5 | 0.6 | 0.6 | 0.3 | 0.4 |
| | Pro-perfume Compound 5 | | | 0.05 | | | | 0.05 | |
| | Pro-perfume Compound 6 | | | | 0.1 | 0.1 | | | |
| | Pro-perfume Compound 15 | 0.15 | | | 0.15 | | 0.1 | | |
| | Pro-perfume Compound 18 | | | | 0.05 | | | 0.2 | |
| | Pro-perfume Compound 19 | | | | | 0.1 | 0.1 | | |
| | Pro-perfume Compound 21 | | | 0.15 | | | | | |
| | Pro-perfume Compound 28 | | 0.1 | | | | | | 0.3 |

TABLE 12-continued

| Pearly shampoo formulations A-H comprising the invention's pro-perfume compositions, (values are in weight-%). | | | | | | | | | |
|---|---|---|---|---|---|---|---|---|---|
| Phase | Ingredients | A | B | C | D | E | F | G | H |
| | Pro-perfume Compound 31 | | 0.05 | 0.1 | | | | | 0.05 |
| | Pro-perfume Compound 44 | | | | 0.1 | | | 0.15 | 0.1 |
| | Pro-perfume Compound 49 | 0.1 | | | | | 0.05 | 0.15 | |

(1) EDETA ® B Powder; origin: BASF
(2) Jaguar ® C14 S; origin: Rhodia
(3) Ucare ® Polymer JR-400; origin: Noveon
(4) Sulfetal ® LA B-E; origin: Zschimmer & Schwarz
(5) Zetesol ® LA; origin: Zschimmer & Schwarz
(6) Tego ® Betain F 50; origin: Evonik
(7) Xiameter ® MEM-1691; origin: Dow Corning
(8) Lanette ® 16; origin: BASF
(9) Comperlan ® 100; origin: Cognis
(10) Cutina ® AGS; origin: Cognis
(11) Kathon ® CG; origin: Rohm & Haas
(12) D-Panthenol; origin: Roche The perfumed shampoo is obtained by adding under gentle shaking a perfume oil and at least two of the pro-perfume compounds according to the present invention (Phase G) into the unperfumed shampoo formulation (Phases A-F).

Example 13

Preparation of Rinse-Off Hair Conditioners Comprising a Pro-Perfume Composition According to the Present Invention Typical rinse-off hair conditioner formulations comprising at least two of the invention's pro-perfumes are listed in Table 13. The ingredients of Phase A are mixed until an uniform mixture was obtained. Tylose® is allowed to completely dissolve. Then the mixture is heated to 70-75° C. The ingredients of Phase B are combined and melted at 70-75° C. Then the ingredients of Phase B are added to Phase A with good agitation and the mixing is continued until that the mixture has a temperature of 60° C. Then, the ingredients of Phase C are added while agitating and keeping mixing until the mixture cooled to 40° C. The pH is adjusted with a citric acid solution to 3.5-4.0.

TABLE 13

| Rinse-off hair conditioner formulations A-H comprising the invention's pro-perfume compositions, (values are in weight-%). | | | | | | | | | |
|---|---|---|---|---|---|---|---|---|---|
| Phase | Ingredients | A | B | C | D | E | F | G | H |
| A | Deionized water | 80.8 | 80.8 | 80.8 | 80.8 | 80.8 | 80.8 | 80.8 | 80.8 |
| | Behentrimonium chloride (1) | 2.5 | 2.5 | 2.5 | 2.5 | 2.5 | 2.5 | 2.5 | 2.5 |
| | Hydroxyethylcellulose (2) | 1.5 | 1.5 | 1.5 | 1.5 | 1.5 | 1.5 | 1.5 | 1.5 |
| B | Cetearyl alcohol (3) | 4.0 | 4.0 | 4.0 | 4.0 | 4.0 | 4.0 | 4.0 | 4.0 |
| | Glyceryl stearate (and) PEG-100 stearate (4) | 2.0 | 2.0 | 2.0 | 2.0 | 2.0 | 2.0 | 2.0 | 2.0 |
| | Behentrimonium metho-sulfate (and) cetyl alcohol (and) butylene glycol (5) | 4.0 | 4.0 | 4.0 | 4.0 | 4.0 | 4.0 | 4.0 | 4.0 |
| | Ethoxy (20) stearyl alcohol (6) | 1.0 | 1.0 | 1.0 | 1.0 | 1.0 | 1.0 | 1.0 | 1.0 |
| C | Amodimethicone (and) Trideceth-12 (and) Cetrimonium chloride (7) | 3.0 | 3.0 | 3.0 | 3.0 | 3.0 | 3.0 | 3.0 | 3.0 |
| | Chlorhexidine digluconate (20% aqueous solution) (8) | 0.2 | 0.2 | 0.2 | 0.2 | 0.2 | 0.2 | 0.2 | 0.2 |
| D | Citric acid (10% aqueous solution till pH 3.5-4.0) | q.s. | q.s. | q.s. | q.s. | q.s. | q.s. | q.s. | q.s. |
| E | Perfume oil | 0.85 | 0.85 | 0.85 | 0.85 | 0.85 | 0.85 | 0.85 | 0.85 |
| | Pro-perfume Compound 1 | 0.05 | | | | | 0.05 | | |
| | Pro-perfume Compound 4 | 0.05 | | | | | | | |
| | Pro-perfume Compound 7 | | 0.05 | | 0.1 | | | | 0.05 |
| | Pro-perfume Compound 9 | 0.05 | | 0.05 | | 0.1 | | 0.1 | 0.1 |

TABLE 13-continued

Rinse-off hair conditioner formulations A-H comprising the invention's pro-perfume compositions, (values are in weight-%).

| Phase | Ingredients | A | B | C | D | E | F | G | H |
|---|---|---|---|---|---|---|---|---|---|
| | Pro-perfume Compound 20 | | | 0.05 | | | | 0.05 | |
| | Pro-perfume Compound 23 | | | 0.05 | 0.05 | | | | |
| | Pro-perfume Compound 43 | | | | | | 0.1 | | |
| | Pro-perfume Compound 48 | | 0.1 | | | 0.05 | | | |

(1) Genamin ® KDMP; origin: Clariant
(2) Tylose ® H10 Y G4; origin: Shin Etsu
(3) Lanette ® O; origin: BASF
(4) Arlacel ® 165; origin: Croda
(5) Incroquat ® Behenyl TMS-50-PA- (MH); origin: Croda
(6) Brij ® S20; origin: Croda
(7) Xiameter ® MEM-949; origin: Dow Corning
(8) Origin: Alfa Aesar The perfumed rinse-off hair conditioner is obtained by adding under gentle shaking a perfume oil and at least two of the pro-perfume compounds according to the present invention (Phase E) into the unperfumed conditioner formulation (Phases A-D).

Example 14

Preparation of Structured Shower Gel Formulations Comprising a Pro-Perfume Composition According to the Present Invention Typical structured shower gel formulations comprising at least two of the invention's pro-perfumes are listed in Table 14. The perfume oil and the pro-perfumes are added under gentle shaking to the unperfumed aqueous shower gel formulation.

TABLE 14

Structured shower gel formulations A-I comprising the invention's pro-perfume compositions, (values are in weight-%).

| Ingredients | A | B | C | D | E | F | G | H | I |
|---|---|---|---|---|---|---|---|---|---|
| Tetrasodium EDTA (1) | 0.05 | 0.05 | 0.05 | 0.05 | 0.05 | 0.05 | 0.05 | 0.05 | 0.05 |
| Acrylates co-polymer (2) | 5.9 | 5.9 | 5.9 | 5.9 | 5.9 | 5.9 | 5.9 | 5.9 | 5.9 |
| Sodium $C_{12-15}$ pareth sulfate (3) | 34.7 | 34.7 | 34.7 | 34.7 | 34.7 | 34.7 | 34.7 | 34.7 | 34.7 |
| Sodium hydroxide (20% aqueous solution) | 1.0 | 1.0 | 1.0 | 1.0 | 1.0 | 1.0 | 1.0 | 1.0 | 1.0 |
| Cocamidopropyl betaine (4) | 7.9 | 7.9 | 7.9 | 7.9 | 7.9 | 7.9 | 7.9 | 7.9 | 7.9 |
| Methylchloroisothiazolinone and methylisothiazolinone (5) | 0.1 | 0.1 | 0.1 | 0.1 | 0.1 | 0.1 | 0.1 | 0.1 | 0.1 |
| Citric acid (40% aqueous solution) | 0.5 | 0.5 | 0.5 | 0.5 | 0.5 | 0.5 | 0.5 | 0.5 | 0.5 |
| Perfume oil | 1.5 | 1.5 | 1.0 | 1.3 | 0.8 | 1.2 | 1.0 | 1.5 | 1.5 |
| Pro-perfume Compound 2(6) | 0.05 | 0.05 | | | 0.05 | 0.1 | | | |
| Pro-perfume Compound 3 | | | 0.1 | 0.1 | | | | | |
| Pro-perfume Compound 4 | | | | 0.05 | | | | | |
| Pro-perfume Compound 10 | 0.1 | | 0.2 | | | | 0.15 | | |
| Pro-perfume Compound 27 | | | | | 0.3 | 0.1 | | | |
| Pro-perfume Compound 29 | | | | | 0.1 | | | 0.05 | 0.05 |
| Pro-perfume Compound 31 | | 0.05 | | 0.05 | | 0.1 | | | 0.1 |
| Pro-perfume Compound 39 | | 0.05 | | | | | | 0.1 | |
| Pro-perfume Compound 48 | | | 0.2 | | 0.1 | | 0.15 | | |
| Deionized water | complete to 100 | | | | | | | | |

(1) EDETA B powder; origin: BASF
(2) Carbopol Aqua SF-1 polymer; origin: Noveon
(3) Zetesol AO 328 U; origin: Zschimmer & Schwarz
(4) Tego Betain F 50; origin: Goldschmidt
(5) Kathon ® CG; origin: Rohm & Haas
(6)mixture of Compounds 2a/2b ca. 45:55

Example 15

Preparation of Milky Shower Gel Formulations Comprising a Pro-Perfume Composition According to the Present Invention Typical milky shower gel formulations comprising at least two of the invention's pro-perfumes are listed in Table 15. The perfume oil and the pro-perfumes are added under gentle shaking to the unperfumed aqueous shower gel formulation.

TABLE 15

Milky shower gel formulations A-H comprising the invention's pro-perfume compositions, (values are in weight-%).

| Ingredients | A | B | C | D | E | F | G | H |
|---|---|---|---|---|---|---|---|---|
| Tetrasodium EDTA [1] | 0.05 | 0.05 | 0.05 | 0.05 | 0.05 | 0.05 | 0.05 | 0.05 |
| Sodium benzoate | 0.50 | 0.50 | 0.50 | 0.50 | 0.50 | 0.50 | 0.50 | 0.50 |
| Glycerin (86% aqueous solution) | 3.50 | 3.50 | 3.50 | 3.50 | 3.50 | 3.50 | 3.50 | 3.50 |
| Sodium laureth sulfate [2] | 26.70 | 26.70 | 26.70 | 26.70 | 26.70 | 26.70 | 26.70 | 26.70 |
| Polyquaternium-7 [3] | 1.00 | 1.00 | 1.00 | 1.00 | 1.00 | 1.00 | 1.00 | 1.00 |
| Coco-betaine [4] | 5.90 | 5.90 | 5.90 | 5.90 | 5.90 | 5.90 | 5.90 | 5.90 |
| PEG-120 Methyl glucose trioleate [5] | 1.00 | 1.00 | 1.00 | 1.00 | 1.00 | 1.00 | 1.00 | 1.00 |
| Citric acid (40% aqueous solution) | 1.00 | 1.00 | 1.00 | 1.00 | 1.00 | 1.00 | 1.00 | 1.00 |
| Glycol distearate & laureth-4 & cocamidopropyl betaine [6] | 2.90 | 2.90 | 2.90 | 2.90 | 2.90 | 2.90 | 2.90 | 2.90 |
| Sodium chloride (20% aqueous solution) | 4.90 | 4.90 | 4.90 | 4.90 | 4.90 | 4.90 | 4.90 | 4.90 |
| PEG-40 hydrogenated castor oil [7] | 1.00 | 1.00 | 1.00 | 1.00 | 1.00 | 1.00 | 1.00 | 1.00 |
| Perfume oil | 1.5 | 1.0 | 1.2 | 1.2 | 1.5 | 0.5 | 1.0 | 1.0 |
| Pro-perfume Compound 1 | | | 0.1 | | | 0.1 | | 0.05 |
| Pro-perfume Compound 5 | | 0.1 | | | 0.05 | | 0.05 | |
| Pro-perfume Compound 6 | | | | | | 0.1 | | |
| Pro-perfume Compound 11 | 0.1 | | | 0.1 | | 0.2 | | |
| Pro-perfume Compound 22 | | | 0.1 | | | | | 0.05 |
| Pro-perfume Compound 30 | | 0.1 | | | 0.1 | | 0.1 | 0.1 |
| Pro-perfume Compound 38 | | 0.05 | | | | | | |
| Pro-perfume Compound 42 | | | | 0.1 | | | | 0.05 |
| Pro-perfume Compound 47 | 0.05 | | | 0.05 | | | 0.1 | |
| Deionized water | complete to 100 | | | | | | | |

[1] EDETA ® B powder; origin: BASF
[2] Texapon ® NSO IS; origin: Cognis
[3] Merquat ® 550; origin: Lubrizol
[4] Dehyton ® AB-30; origin: Cognis
[5] Glucamate ® LT; origin: Lubrizol
[6] Euperlan ® PK 3000 AM; origin: Cognis
[7] Cremophor ® RH 40; origin: BASF

Example 16

Preparation of Anhydrous Antiperspirant Spray Formulations Comprising a Pro-Perfume Composition According to the Present Invention Typical unperfumed anhydrous antiperspirant spray formulations comprising at least two of the invention's pro-perfumes are listed in Table 16. Anhydrous antiperspirant spray formulations are prepared by using a high speed stirrer. Silica and Quaternium-18-hectorite are added to the mixture of isopropyl myristate and cyclomethicone. Once completely swollen, aluminium chlorohydrate is added portion-wise under stirring until the mixture becomes homogeneous and without lumps. Then a perfume oil and the pro-perfumes are added.

TABLE 16

Anhydrous antiperspirant spray formulations A-H comprising the invention's pro-perfume compositions, (values are in weight-%).

| Ingredients | A | B | C | D | E | F | G | H |
|---|---|---|---|---|---|---|---|---|
| Cyclomethicone [1] | 53.0 | 53.0 | 53.0 | 53.0 | 53.0 | 53.0 | 53.0 | 53.0 |
| Isopropyl myristate | 9.0 | 9.0 | 9.0 | 9.0 | 9.0 | 9.0 | 9.0 | 9.0 |
| Silica [2] | 1.0 | 1.0 | 1.0 | 1.0 | 1.0 | 1.0 | 1.0 | 1.0 |

TABLE 16-continued

Anhydrous antiperspirant spray formulations A-H comprising the invention's pro-perfume compositions, (values are in weight-%).

| Ingredients | A | B | C | D | E | F | G | H |
|---|---|---|---|---|---|---|---|---|
| Quaternium-18-hectorite [(3)] | 3.3 | 3.3 | 3.3 | 3.3 | 3.3 | 3.3 | 3.3 | 3.3 |
| Aluminium chlorohydrate [(4)] | 32.7 | 32.7 | 32.7 | 32.7 | 32.7 | 32.7 | 32.7 | 32.7 |
| Perfume oil | 0.85 | 0.85 | 0.85 | 0.85 | 0.85 | 0.85 | 0.85 | 0.85 |
| Pro-perfume Compound 1 | 0.05 | | 0.05 | | 0.01 | | | |
| Pro-perfume Compound 5 | 0.05 | | | | | | 0.1 | |
| Pro-perfume Compound 7 | | | | 0.1 | | | | |
| Pro-perfume Compound 10 | | 0.1 | | | 0.05 | | | |
| Pro-perfume Compound 18 | | | | 0.05 | 0.02 | | | |
| Pro-perfume Compound 21 | | 0.05 | | | | 0.05 | | 0.1 |
| Pro-perfume Compound 29 | | | 0.1 | | | 0.05 | 0.05 | |
| Pro-perfume Compound 46 | 0.05 | | | | 0.07 | 0.05 | | 0.05 |

(1) Dow Corning ® 345 Fluid; origin: Dow Corning (2) Aerosil ® 200; origin: Evonik (3) Bentone ® 38; origin: Elementis Specialities (4) Micro Dry Ultrafine; origin: Reheis

Example 17

Preparation of Deodorant Spray Emulsion Formulations Comprising a Pro-Perfume Composition According to the Present Invention Typical deodorant spray emulsion formulations comprising at least two of the invention's pro-perfumes are listed in Table 17. Deodorant spray emulsion formulations are prepared by mixing and dissolving all the ingredients according to the sequence of Table 17. Aerosol cans are filled, and the propellant is crimped and added. Aerosol filling: 40% active solution 60% propane/butane (2.5 bar).

TABLE 17

Deodorant spray emulsion formulations A-H comprising the invention's pro-perfume compositions, (values are in weight-%).

| Ingredients | A | B | C | D | E | F | G | H |
|---|---|---|---|---|---|---|---|---|
| Ethanol (95%) | 89.25 | 89.25 | 89.25 | 89.25 | 89.25 | 89.25 | 89.25 | 89.25 |
| Triclosan [(1)] | 0.25 | 0.25 | 0.25 | 0.25 | 0.25 | 0.25 | 0.25 | 0.25 |
| Isopropyl myristate | 9.00 | 9.00 | 9.00 | 9.00 | 9.00 | 9.00 | 9.00 | 9.00 |
| Perfume oil | 1.35 | 1.35 | 1.35 | 1.35 | 1.35 | 1.35 | 1.35 | 1.35 |
| Pro-perfume Compound 2[(2)] | 0.08 | | | | 0.05 | | | |
| Pro-perfume Compound 4 | | 0.02 | | | | 0.01 | | |
| Pro-perfume Compound 6 | | | 0.03 | | | 0.04 | | |
| Pro-perfume Compound 9 | | 0.08 | | 0.08 | | | 0.08 | |
| Pro-perfume Compound 27 | | | | 0.03 | 0.05 | | | |
| Pro-perfume Compound 30 | | | 0.12 | | 0.05 | | 0.07 | 0.06 |
| Pro-perfume Compound 31 | 0.06 | | | 0.03 | | | | 0.09 |
| Pro-perfume Compound 45 | | 0.05 | | | | 0.10 | | |

(1) Irgasan ® DP 300; origin: BASF (2) mixture of Compounds 2a/2b ca. 45:55

Example 18

Preparation of Deodorant Stick Formulations Comprising a Pro-Perfume Composition According to the Present Invention Typical deodorant stick formulations comprising at least two of the invention's pro-perfumes are listed in Table 18. Deodorant stick formulations are obtained by weighing all the components of Part A and heating to 70-75° C. Ceteareth-25 is added once the other Part A ingredients are mixed and heated. When the Ceteareth-25 is dissolved, stearic acid is added. Part B is prepared by dissolving Triclosan in 1,2-propylene glycol. Evaporated water is compensated. Then, slowly, under mixing, Part B is poured into Part A. A perfume oil and the pro-perfumes (Phase C) are added under gentle shaking. To stock, a plastic bag is put into the bucket to be sealed after cooling. Moulds were filled at about 70° C.

TABLE 18

Deodorant stick formulations A-F comprising the invention's pro-perfume compositions, (values are in weight-%).

| Phase | Ingredients | A | B | C | D | E | F |
|---|---|---|---|---|---|---|---|
| A | Stearic acid | 5.00 | 5.00 | 5.00 | 5.00 | 5.00 | 5.00 |
| | 1,2-Propylene glycol | 41.45 | 41.45 | 41.45 | 41.45 | 41.45 | 41.45 |
| | Sodium hydroxide (20% aqueous solution) | 4.20 | 4.20 | 4.20 | 4.20 | 4.20 | 4.20 |
| | Water | 30.00 | 30.00 | 30.00 | 30.00 | 30.00 | 30.00 |
| | Tetrasodium EDTA (1) | 0.10 | 0.10 | 0.10 | 0.10 | 0.10 | 0.10 |
| | Ceteareth-25 (2) | 1.50 | 1.50 | 1.50 | 1.50 | 1.50 | 1.50 |
| | PPG-3 Myristyl ether (3) | 1.50 | 1.50 | 1.50 | 1.50 | 1.50 | 1.50 |
| B | 1,2-Propylene glycol | 15.00 | 15.00 | 15.00 | 15.00 | 15.00 | 15.00 |
| | Triclosan (4) | 0.25 | 0.25 | 0.25 | 0.25 | 0.25 | 0.25 |
| C | Perfume oil | 0.85 | 0.85 | 0.85 | 0.85 | 0.85 | 0.85 |
| | Pro-perfume Compound 3 | | 0.02 | | | 0.07 | |
| | Pro-perfume Compound 8 | 0.07 | | 0.02 | 0.09 | | |
| | Pro-perfume Compound 11 | | 0.03 | | | | 0.05 |
| | Pro-perfume Compound 20 | | | 0.02 | | | |
| | Pro-perfume Compound 24 | 0.08 | | | 0.03 | | 0.04 |
| | Pro-perfume Compound 28 | | | | 0.03 | | |
| | Pro-perfume Compound 29 | | | 0.11 | | 0.08 | |
| | Pro-perfume Compound 45 | | 0.01 | | | | 0.06 |

(1) Edeta ® B Power; origin: BASF
(2) Cremophor ® A25; origin: BASF
(3) Tegosoft ® APM; origin: Evonik
(4) Irgasan ® DP 300; origin: BASF Example 19

Preparation of Deodorant Roll-on Formulations Comprising a Pro-Perfume Composition According to the Present Invention Typical deodorant roll-on formulations comprising at least two of the invention's pro-perfumes are listed in Table 19. Part A is prepared by sprinkling little-by-little the hydroxyethylcellulose into the water, whilst rapidly stirring with a turbine until the hydroxyethylcellulose is entirely swollen giving a limpid gel. Part B is slowly poured into Part A, whilst continuing stirring until the entire mixture is homogeneous. Then Parts C and D are added under gentle shaking.

TABLE 19

Deodorant roll-on formulations A-F comprising the invention's pro-perfume compositions, (values are in weight-%).

| Phase | Ingredients | A | B | C | D | E | F |
|---|---|---|---|---|---|---|---|
| A | Water | 50.00 | 50.00 | 50.00 | 50.00 | 50.00 | 50.00 |
| | Hydroxyethylcellulose (1) | 0.70 | 0.70 | 0.70 | 0.70 | 0.70 | 0.70 |

TABLE 19-continued

Deodorant roll-on formulations A-F comprising the invention's pro-perfume compositions, (values are in weight-%).

| Phase | Ingredients | A | B | C | D | E | F |
|---|---|---|---|---|---|---|---|
| B | Ethanol (95%) | 40.00 | 40.00 | 40.00 | 40.00 | 40.00 | 40.00 |
| | 1,2-Propylene glycol | 5.00 | 5.00 | 5.00 | 5.00 | 5.00 | 5.00 |
| | Triclosan (2) | 0.30 | 0.30 | 0.30 | 0.30 | 0.30 | 0.30 |
| C | PEG-40 hydrogenated castor oil (3) | 3.00 | 3.00 | 3.00 | 3.00 | 3.00 | 3.00 |
| D | Perfume oil | 0.85 | 0.85 | 0.85 | 0.85 | 0.85 | 0.85 |
| | Pro-perfume Compound 1 | | | | 0.02 | | 0.03 |
| | Pro-perfume Compound 4 | | 0.02 | | 0.02 | | |
| | Pro-perfume Compound 8 | | | | 0.01 | | |
| | Pro-perfume Compound 14 | | | 0.06 | | | |
| | Pro-perfume Compound 17 | 0.05 | | | | | |
| | Pro-perfume Compound 19 | | 0.02 | | | 0.06 | |
| | Pro-perfume Compound 25 | | | | 0.03 | | |
| | Pro-perfume Compound 29 | | 0.09 | | | | |
| | Pro-perfume Compound 31 | | | | 0.02 | 0.09 | |
| | Pro-perfume Compound 38 | | | 0.04 | | | 0.06 |
| | Pro-perfume Compound 43 | | | 0.05 | | | |
| | Pro-perfume Compound 46 | 0.05 | | | 0.05 | | |
| | Pro-perfume Compound 47 | 0.05 | | | | | 0.06 |

(1) Natrosol ® 250 H; origin: Ashland
(2) Irgasan ® DP 300; origin: BASF
(3) Cremophor ® RH 40; origin: BASF

Example 20

Preparation of Day Cream Base O/W Emulsions Comprising a Pro-Perfume Composition According to the Present Invention Typical day cream base O/W emulsions comprising at least two of the invention's pro-perfumes are listed in Table 20. Day cream base O/W emulsions are prepared by heating Phases A and B separately to 70-75° C. Phase A is added to Phase B, then vacuum is applied. The mixture is stirred and cooled to 55° C. for 15 min. After cooling to room temperature, phenoxyethanol (and) piroctone olamine (Part C) are added when a temperature of 45° C. is reached. The mixture is stirred for 5 min before sodium carbomer (Part D) and a perfume oil and pro-perfumes (Part E) are added. The mixture is stirred for 3 min, then the stirring was stopped for 15 min. When the temperature of the mixture reaches 30° C., the stirring is resumed for another 15 min until the cream becomes homogeneous, glossy and without lumps. If necessary the pH is adjusted to 6.70-7.20 with Glydant, Phenonip or Nipaguard PO5 or to 6.30-7.00 with Nikkoguard.

TABLE 20

Day cream base O/W emulsion formulations A-E comprising the invention's pro-perfume compositions, (values are in weight-%).

| Phase | Ingredients | A | B | C | D | E |
|---|---|---|---|---|---|---|
| A | Steareth-2 (and) PEG-8 Distearate(1) | 5.0 | 5.0 | 5.0 | 5.0 | 5.0 |
| | Cetyl alcohol | 0.5 | 0.5 | 0.5 | 0.5 | 0.5 |
| | Ceteth-20 (AND) glyceryl stearate (and) PEG-6 stearate (and) Steareth-20 (2) | 4.0 | 4.0 | 4.0 | 4.0 | 4.0 |
| | Squalan (3) | 1.0 | 1.0 | 1.0 | 1.0 | 1.0 |
| | Paraffin oil (4) | 2.0 | 2.0 | 2.0 | 2.0 | 2.0 |
| | Petrolatum (5) | 5.5 | 5.5 | 5.5 | 5.5 | 5.5 |
| B | Deionized water | 75.9 | 75.9 | 75.9 | 75.9 | 75.9 |
| | Propylene glycol | 5.0 | 5.0 | 5.0 | 5.0 | 5.0 |
| C | Phenoxyethanol (AND) Piroctone olamine (6) | 0.6 | 0.6 | 0.6 | 0.6 | 0.6 |
| D | Sodium carbomer (7) | 0.2 | 0.2 | 0.2 | 0.2 | 0.2 |
| E | Perfume oil | 0.15 | 0.15 | 0.15 | 0.15 | 0.15 |
| | Pro-perfume Compound 1 | 0.04 | 0.06 | 0.01 | | |
| | Pro-perfume Compound 10 | 0.04 | | 0.06 | | 0.10 |
| | Pro-perfume Compound 24 | 0.07 | | | | |
| | Pro-perfume Compound 27 | | | | | 0.03 |
| | Pro-perfume Compound 29 | | 0.09 | | 0.05 | |
| | Pro-perfume Compound 31 | | | | 0.05 | 0.02 |
| | Pro-perfume Compound 45 | | | 0.08 | 0.05 | |

(1)Arlacel ® 985; origin: Croda
(2) Tefose ® 2561; origin: Gattefossé
(3) Biolip P 90; origin: Gattefossé
(4) Mineral oil 30-40 CPS
(5) Petroleum jelly
(6) Nipaguard ® PO 5; origin: Clariant
(7) PNC 400

The invention claimed is:

1. A perfuming composition comprising at least two pro-perfume compounds comprising a first pro-perfume compound and a second pro-perfume compound, wherein the at least two pro-perfume compounds are selected from the group consisting of a pro-perfume compound releasing a perfume compound upon exposure to light, a pro-perfume compound releasing a perfume compound upon exposure to air/oxygen, a pro-perfume compound releasing a perfume compound upon exposure to heat, a pro-perfume compound releasing a perfume compound upon exposure to moisture and a pro-perfume compound releasing a perfume compound upon exposure to enzymes, wherein the first pro-perfume compound is a compound of formula:

a)

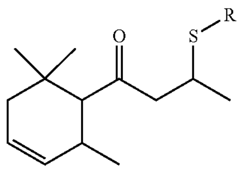

b)

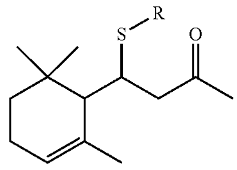

c)

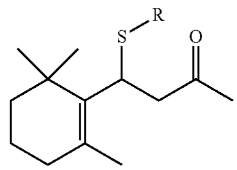

d)

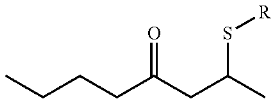

wherein R represents a $C_1$-$C_{20}$ alkyl or alkenyl group, or wherein the first pro-perfume compound is a linear polysiloxane co-polymer comprising at least one repeating unit of formula (III)

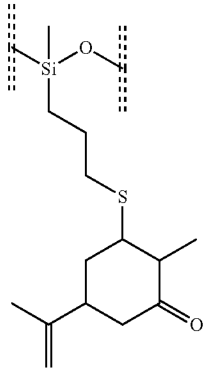

wherein the double hatched lines indicate the bonding to another repeating unit; and wherein the second pro-perfume compound is a compound of formula (IV)

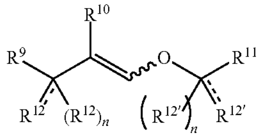

wherein $R^9$ represents a $C_{1-15}$ alkyl, $C_{2-15}$ alkenyl, $C_{3-15}$ cycloalkyl or $C_{5-15}$ cycloalkenyl group, each optionally substituted with one or more of a $C_{1-15}$ alkyl, $C_{1-15}$ alkoxy, $C_{3-15}$ cycloalkyl, $C_{5-15}$ cycloalkenyl, $C_{6-10}$ aryl and/or $C_{6-10}$ aryloxy group, each optionally substituted with one or more of a $C_{1-8}$ alkyl, $C_{1-8}$ alkoxy, hydroxy, carboxylic acid and/or $C_{1-4}$ carboxylic ester group;

$R^{10}$ represents a hydrogen atom, a $C_{1-15}$ alkyl group or a $OR^{10'}$ wherein $R^{10'}$ represents a $C_{1-12}$ alkyl group, a $C_{3-12}$ alkenyl group, a phenethyl group or a benzyl group;

$R^9$ and $R^{10}$, when taken together, form a $C_{5-15}$ cycloalkyl, $C_{5-15}$ cycloalkenyl, $C_{4-14}$ heterocycloalkyl or $C_{4-14}$ heterocycloalkenyl group, each optionally substituted with one or more of a $C_{1-15}$ alkyl, $C_{1-15}$ alkoxy, $C_{3-15}$ cycloalkyl, $C_{5-15}$ cycloalkenyl or $C_{6-10}$ aryl group, each optionally substituted with one or more of a $C_{1-8}$ alkyl, $C_{1-8}$ alkoxy, carboxylic acid and/or $C_{1-4}$ carboxylic ester group, wherein the heteroatom represents one or more of an oxygen;

$R^{11}$ represents a hydrogen, a $C_{1-15}$ alkyl, $C_{2-15}$ alkenyl, $C_{3-15}$ cycloalkyl, $C_{5-15}$ cycloalkenyl or $C_{6-10}$ aryloxy group, each optionally substituted with one or more a $C_{1-15}$ alkyl, $C_{1-15}$ alkoxy, $C_{3-15}$ cycloalkyl, $C_{5-15}$ cycloalkenyl, $C_{6-10}$ aryl and/or $C_{6-10}$ aryloxy group, each optionally substituted with one or more of a $C_{1-8}$ alkyl, $C_{1-8}$ alkoxy, carboxylic acid and/or $C_{1-4}$ carboxylic ester group; and $R^{12}$, each independently, represent a hydrogen or a $C_{1-5}$ alkyl group; and $R^{11}$ and $R^{12'}$, when taken together, form a $C_{3-15}$ cycloalkyl, $C_{5-15}$ cycloalkenyl or $C_{6-10}$ aryl group, each optionally substituted with one or more of a $C_{1-15}$ alkyl, $C_{2-10}$ alkenyl, $C_{1-15}$ alkoxy, $C_{3-15}$ cycloalkyl, $C_{5-15}$ cycloalkenyl, $C_{6-10}$ aryl and/or $C_{6-10}$ aryloxy group, each optionally substituted with one or more of a $C_{1-8}$ alkyl, $C_{1-8}$ alkoxy, carboxylic acid and/or $C_{1-4}$ carboxylic ester group;

$R^9$ and $R^{12}$, when taken together, form a $C_{3-15}$ cycloalkyl, $C_{5-15}$ cycloalkenyl group or $C_{6-10}$ aryl group, each optionally substituted with one or more of a $C_{1-15}$ alkyl, $C_{2-10}$ alkenyl, $C_{1-15}$ alkoxy, $C_{3-15}$ cycloalkyl, $C_{5-15}$ cycloalkenyl, $C_{6-10}$ aryl and/or $C_{6-10}$ aryloxy group, each optionally substituted with one or more of a $C_{1-8}$ alkyl, $C_{1-8}$ alkoxy, carboxylic acid and/or $C_{1-4}$ carboxylic ester group; and the dotted line represent a single bond when n is 1 or the dotted line represent a double bond when n is 0 provided that the dotted line is a double bond when $R^9$ and $R^{12}$ and/or $R^{11}$ and $R^{12'}$ are taken together to form $C_{6-10}$ aryl.

2. The perfuming composition according to claim 1, wherein the second pro-perfume compound of formula (IV) is selected from the group consisting of (2-((2-methylundec-1-en-1-yl)oxy)ethyl)benzene, 1-methoxy-4-(3-methyl-4-phenethoxybut-3-en-1-yl)benzene, (3-methyl-4-phenethoxybut-3-en-1-yl)benzene, 1-(((Z)-hex-3-en-1-yl)oxy)-2-methylundec-1-ene, (2-((2-methylundec-1-en-1-yl)oxy)ethoxy)benzene, 2-methyl-1-(octan-3-yloxy)undec-1-ene, 1-methoxy-4-(1-phenethoxyprop-1-en-2-yl)benzene, 1-methyl-4-(1-phenethoxyprop-1-en-2-yl)benzene, 2-(1-phenethoxyprop-1-en-2-yl)naphthalene, (2-phenethoxyvinyl)benzene, 2-(1-((3,7-dimethyloct-6-en-1-yl)oxy)prop-1-en-2-yl)naphthalene, 1-(4-(((Z)-hex-3-en-1-yl)oxy)-3-methylbut-3-en-1-yl)-4-methoxybenzene, (2-((2-pentylcyclopentylidene)methoxy)ethyl)benzene, (2-((2-heptylcyclopentylidene)methoxy)ethyl)benzene, (2-((2-methyl-4-(2,6,6-trimethylcyclohex-1-en-1-yl)but-1-en-1-yl)oxy)ethyl)benzene, 1-methoxy-4-(2-methyl-3-phenethoxyallyl)benzene, (2-((2-isopropyl-5-methylcyclohexylidene)methoxy)ethyl)benzene, 1-isopropyl-4-methyl-2-((2-pentylcyclopentylidene)methoxy)benzene, 2-methoxy-1-((2-methoxy-2-phenylvinyl)oxy)-4-propylbenzene, 2-ethoxy-1-((2-methoxy-2-phenylvinyl)oxy)-4-methylbenzene, 2-ethoxy-1-((2-ethoxy-2-phenylvinyl)oxy)-4-methylbenzene, 3-methoxy-4-((2-methoxy-2-phenylvinyl)oxy)benzaldehyde, 1-isopropyl-2-((2-methoxy-2-phenylvinyl)oxy)-4-methylbenzene, 4-allyl-2-methoxy-1-((2-methoxy-2-phenylvinyl)oxy)benzene, (1E,5E)-9-(phenethoxymethylene)cyclododeca-1,5-diene, 1-((2,6-dimethyloct-7-en-2-yl)oxy)-2-methylundec-1-ene, (3-methyl-4-(octyloxy)but-3-en-1-yl)benzene, 4-(4-((2-phenylprop-1-en-1-yl)oxy)phenyl)butan-2-one, 4-allyl-2-methoxy-1-((2-methylundec-1-en-1-yl)oxy)benzene, 1-((2-ethyl-4,4-dimethylcyclohexylidene)methoxy)-2-methoxy-4-propylbenzene, 2-methoxy-1-((2-pentylcyclopentylidene)methoxy)-4-propylbenzene, 4-allyl-2-methoxy-1-((4-(tert-pentyl)cyclohexylidene)methoxy)benzene, methyl 2-((2-methoxy-2-phenylvinyl)oxy) benzoate, methyl 3-methoxy-4-((2-methoxy-2-phenylvinyl)oxy) benzoate, 2-ethoxy-1-((2-methoxy-2-phenylvinyl)oxy)-4-(methoxymethyl)benzene, (Z)-hex-3-en-1-yl 2-((2-methoxy-2-phenylvinyl)oxy) benzoate, 1-((2-butoxy-2-phenylvinyl)oxy)-2-methoxy-4-propylbenzene, 2-methoxy-1-((2-methoxy-2-(4-methoxyphenyl) vinyl)oxy)-4-propylbenzene, 4-((2-(hexyloxy)-2-phenylvinyl)oxy)-3-methoxybenzaldehyde, methyl 4-((2-(hexyloxy)-2-phenylvinyl)oxy)-3-methoxybenzoate and (Z)-hex-3-en-1-yl 2-((2-(((Z)-hex-3-en-1-yl)oxy)-2-phenylvinyl)oxy) benzoate.

3. A perfumed consumer product comprising the perfuming composition according to claim 1.

4. The perfumed consumer product according to claim 3, wherein the perfumed consumer product is a perfume, a fabric care product, a body-care product, a cosmetic preparation, a skin-care product, an air care product or a home care product, a fine perfume, a splash or eau de perfume, a cologne, a shave or after-shave lotion, a liquid or solid detergent, a fabric softener, a fabric refresher, an ironing water, a paper, a bleach, a carpet cleaners, curtain-care products, a shampoo, a coloring preparation, a color care product, a hair shaping product, a dental care product, a disinfectant, an intimate care product, a hair spray, a hair conditioning product, a vanishing cream, a deodorant or antiperspirant, hair remover, tanning or sun product, nail products, skin cleansing, a makeup, a perfumed soap, shower or bath mousse, oil or gel, or a foot/hand care products, a hygiene product, an air freshener, a "ready to use" powdered air freshener, a mold remover, furnisher care, wipe, a dish detergent or hard-surface detergent, a leather care product, or a car care product.

5. A method of using a perfuming composition as defined in claim 1, the method comprising using the perfuming composition for improving, enhancing, conferring, and/or modifying the fragrance impression and/or fragrance intensity of a consumer product.

6. A method for improving, enhancing, conferring, and/or modifying the fragrance impression and/or fragrance intensity of a consumer product, the method comprising the step of adding the perfuming composition as defined in claim 1 to a consumer product.

* * * * *